(12) United States Patent
Shen et al.

(10) Patent No.: US 10,287,269 B2
(45) Date of Patent: May 14, 2019

(54) PYRAZOLYL PYRIMIDINONE COMPOUNDS AS PDE2 INHIBITORS

(71) Applicant: Merck Sharp & Dohme Corp., Rahway, NJ (US)

(72) Inventors: Dong-Ming Shen, Edison, NJ (US); Jonathan E. Wilson, South Orange, NJ (US); Meng Yang, Westfield, NJ (US); Dann Parker, Cranford, NJ (US); Zack Zhiqiang Guo, Morganville, NJ (US); Alejandro Crespo, Westfield, NJ (US); Deping Wang, Furlong, PA (US); Troy McCracken, Berkeley Heights, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/559,284

(22) PCT Filed: Mar. 21, 2016

(86) PCT No.: PCT/US2016/023344
§ 371 (c)(1),
(2) Date: Sep. 18, 2017

(87) PCT Pub. No.: WO2016/154081
PCT Pub. Date: Sep. 29, 2016

(65) Prior Publication Data
US 2018/0057480 A1    Mar. 1, 2018

Related U.S. Application Data

(60) Provisional application No. 62/138,429, filed on Mar. 26, 2015.

(51) Int. Cl.
*C07D 403/04* (2006.01)
*C07D 401/14* (2006.01)
*C07D 405/14* (2006.01)

(52) U.S. Cl.
CPC ......... *C07D 403/04* (2013.01); *C07D 401/14* (2013.01); *C07D 405/14* (2013.01)

(58) Field of Classification Search
CPC .................................................. C07D 403/04
See application file for complete search history.

(56) References Cited

U.S. PATENT DOCUMENTS

| | | |
|---|---|---|
| 4,849,424 A | 7/1989 | Ikeda et al. |
| 5,582,019 A | 12/1996 | Hanna et al. |
| 5,852,019 A * | 12/1998 | Ejima .................. C07D 403/04 514/252.02 |
| 6,573,263 B2 | 6/2003 | Niewohner et al. |
| 7,144,913 B2 | 12/2006 | Wang et al. |
| 7,419,969 B2 | 9/2008 | Naidu et al. |
| 8,598,155 B2 | 12/2013 | Helal et al. |
| 8,680,116 B2 | 3/2014 | DeLeon et al. |
| 2007/0135457 A1 | 6/2007 | Beyer et al. |
| 2007/0281917 A1 | 12/2007 | Naidu et al. |
| 2009/0253677 A1 | 10/2009 | Beaulieu et al. |
| 2010/0273754 A1 | 10/2010 | Li |
| 2012/0214791 A1 | 8/2012 | Helal et al. |

FOREIGN PATENT DOCUMENTS

| | | |
|---|---|---|
| EP | 1097706 A1 | 5/2001 |
| EP | 1097707 A1 | 5/2001 |
| WO | WO2003035076 | 5/2003 |
| WO | WO2003035077 A1 | 5/2003 |
| WO | WO2005061497 | 12/2003 |
| WO | WO2005041957 | 10/2004 |
| WO | WO2004096128 | 11/2004 |
| WO | WO2006024640 | 3/2006 |
| WO | WO200672615 | 7/2006 |

(Continued)

OTHER PUBLICATIONS

Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.

(Continued)

*Primary Examiner* — Paul V Ward
(74) *Attorney, Agent, or Firm* — Sylvia A. Ayler; John C. Todaro

(57) ABSTRACT

The present invention is directed to pyrimidine carboxamide compounds of formula I which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

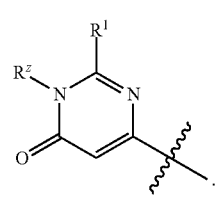

19 Claims, No Drawings

(56) References Cited

FOREIGN PATENT DOCUMENTS

| WO | WO2007058646 | 5/2007 |
|----|----|----|
| WO | WO2009016498 | 2/2009 |
| WO | WO2009117540 | 9/2009 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012151567 | 11/2012 |
| WO | WO2012154880 | 11/2012 |
| WO | WO2012168817 | 12/2012 |
| WO | WO201300924 | 1/2013 |
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014139983 | 9/2014 |
| WO | WO2015012328 | 1/2015 |

OTHER PUBLICATIONS

Boyd et al., 2-Substituted-4,5-Dihydroxypyrimidine-6-Carboxamide Antiviral Targeted Libraries, J. Comb. Chem, 2009, 1100-1104, 11.

Brandon et al., Potential CNS Applications for, Annual Reports in Medicinal Chemistry, 2007, 3-11, 42.

Bubb et al., Inhibition of Phosphodiesterase 2 Augments cGMP and, Circulation, 2014, 496-507, 268.

Card et al., Structural Basis for the Activity of Drugs that Inhibit Phosphodiesterases, Structure, 2004, 2233-2247, 12.

Cote et al., Comparative Involvement of Cyclic Nucleotide, Endocrinology, 1999, 3594-3601, 140.

Demaria et al., Highlights of the Year in JACC 2013, j. aMER. cOLL. cARD, 2014, 570-602, 63, (6).

Dickinson et al., Activation of cGMP-stimulated phosphodiesterase by nitroprusside limits, Biochem J., 1997, 371-377, 323.

Ding et al, Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.

Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.

Ducrot et al, CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.

Duran et al., The NO cascade, eNOS Location, and Microvascular Permeability, Cardiovascular Research, 2010, 254-261, 87.

Favot et al., VEGF-Induced HUVEC Migration and Proliferation, Schattauer GmbH Stuttgart, 2003, 3443-343, 90.

Gergega et al., Systematic Effect of Benzo-Annelation on Oxo-Hydroxy Tautomerism of Heterocyclic, J. Phys. Chem A., 2007, 4934-4943, 111.

Giuliano et al., Correction to Tautomerism in 4-Hydroxypyrimidine, S-Methyl-2-thiouracil, and 2-Thiouracil, The Journal of Physical Chemistry A, 2011, 8178-8179, 115.

Giuliano et al., Tautomerism in 4-Hydroxypyrimidine, S-Methyl-2-thiouracil, and 2-Thiouracil, J. Phys. Chem. A, 2010, 12725-12730, 114.

Haynes et al., Erythro-9-(2-Hydroxy-3-Nonyl) Adenine Inhibits Cyclic-3',5' Guanosine Monophosphate—Stimulated Phosphodiesterase to Reverse Hypoxic Pulmonary Vasoconstriction in the Perfused Rat Lung, The J. of Pharmacology, 1996, 752-757, 276.

Herring et al., NO-cGMP Pathway Increases the Hyperpolarisation-Activated Current ,I, and Heart Rate During Adrenergic Stimulation, Cardiovascular Research, 2001, 446-453, 52.

Hiramoto et al., Role of Phosphodiesterase 2 in Growth and Invasion of HUman Maligant Melanoma, Cellular Signaling, 2014, 1807-1817, 26.

Huang et al., A Fluroescence Polarization Assay for Cyclic Nucleotide Phosphodiesterases, J. of Biomolecular Screening, 2002, pp. 215-222, 7.

Jorgensen et al., Selective Inhibitors of PDE2, PDE9, and PDE10: Modulators of Activity of the Central Nervous System, Annual Reports in Medicinal Chemistry, 2013, pp. 37-55, 48.

Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.

Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.

Lieberman et al., Effectiveness of Antipsychotic Drugs in Patients with Chronic Schizophrenia, New England J. of Medicine, Sep. 22, 2005, pp. 1209-1223, 353, US.

Lopez et al., Solution and solid state (CPMAS) NMR Studies of the Tautomerism of Six-Membered Heterocyclic Compounds Related to 2-Pyridones, Spectroscopy, 2000, pp. 121-126, 14.

Masood et al., Anxiolytic Effects of Phosphodiesterase-2 Inhibitors Associated with Increased cGMP Signaling, J. of Pharmacology, 2009, 690-699, 331.

Masood et al., Reversal of Oxidative Stress-Induced Anxiety by Inhibition of Phosphodiesterase-2 in Mice, J. of Pharmacology and Experimental Therapeutics, 2008, 369-379, 326.

Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.

Morita et al., Characterization of Phosphodiesterase 2A in Human Malignant Melanoma PMP Cells, Oncology Reports, 2013, 1275-1284, 29.

Netherton et al., Vascular Endothelial Cell Cyclic Nucleotide phosphodiesterases and Regulated Cell Migration: IMplications in Angiogenesis, Molecular Pharmacology, 2005, 263-272, 67.

P. C. Tfelt-Hansen et al., One Hundred Years of Migraine Research: Major Clinical and, Headache, 2011, 752-778, 51.

Pace et al., Dihydroxypyrimidine-4-Carboxamides As Novel Poten and Selective HIV Integrase Inhibitors, J. Med Chem., 2007, 2225-2239, 50.

Petrocchi et al., From dihydroxypyrimidine carboxylic acids to carboxamide, Bioorganic & Medicinal Chemistry Letters, 2007, 350-353, 17.

Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.

Plummer et al., Discovery of potent selective bioavailable phosphodiesterase, Bioorganic & Medicinal Chemistry Letters, 2013, 3443-3447, 23.

Pubchem-CID-69915039, Dec. 1, 2012 (Dec. 1, 2012), Entire Document, Especially p. 3, FIG.

Reierson et al., Repeated antidepressant therapy increases cyclic GMP signaling, Neurosci Letter, 2009, 149-153, 466 (3).

Rivet-Bastide et al., cGMP-stimulated Cyclic Nucleotide Phosphodiesterase Regulates the Basal, J. Clin. Invest, 1997, 2710-2718, 99.

Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.

Sanchez et al., Gas-Phase Tautomeric Equilibrium of 4-Hydroxypyrimidine, J. Am. Chem Soc., 2007, 6287-6290, 129.

Savai et al., Targeting Cancer with Phosphodiesterase Inhibitors, Expert Opinion, 2010, 117-131, 19.

Surapisitchat et al., Differential Regulation of Endothelial Cell Permeability by cGMP via Phosphodiesterases 2 and 3, Circulation Research, 2007, 811-818, 101.

(56) References Cited

OTHER PUBLICATIONS

Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.

* cited by examiner

PYRAZOLYL PYRIMIDINONE COMPOUNDS AS PDE2 INHIBITORS

CROSS REFERENCE TO RELATED APPLICATIONS

This application is the National Stage of International Application No. PCT/US2016/023344 filed on Mar. 21, 2016, which claims the benefit under U.S. Provisional application 62/138,429, filed Mar. 26, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001)); platelet aggregation (R. J. Haslam, et Al., Biochem. J., 323, 371 (1997); female sexual arousal disorder (C. P. Wayman, et al., EP Patent Publications EP10977707 and EP1097706; osteoarthritis pain (M. Plummer et, al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et al., J. Pharm. Exp. Ther., 276, 752 (1996)). See also 2-Substituted-4,5-dihydroxypyrimidine-6-carboxamide Antiviral Targeted Libraries, Vincent Boyd et al., Journal of Combinatorial Chemistry (2009), 11(6), 1100-1104; From Dihydroxypyrimidine Carboxylic Acids to Carboxamide HIV-1 Integrase Inhibitors: SAR Around the Amide Moiety, Alessia Petrocchi et al., Bioorganic & Medicinal Chemistry Letters (2007), 17(2), 350-353; Dihydroxypyrimidine-4-carboxamides as Novel Potent and Selective HIV Integrase Inhibitors, Paola Pare et al., Journal of Medicinal Chemistry (2007), 50(9), 2225-2239; US2007135457, WO2012151567, US20090253677, US20070281917, WO2004096128, WO2003035077, WO2003035076, WO2007058646, WO2009117540, and U.S. Pat. No. 7,419, 969.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7):1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Left., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263, 8,598,155, and 8,680,116; WO2015012328; WO2014139983; WO2014019979; WO2014010732; WO2013000924; WO2012114222; WO2006072615; WO2005063723; M. Plummer et al., Bioorg Med Chem Left 23(11), 3438, 2013; and M. Plummer et al., Bioorg Med Chem Left 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al, *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating PDE2 conditions, diseases or disorders associated with PDE2 such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to pyrazole pyrimidinone compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to pyrazole pyrimidinone compounds of formula I:

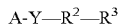

or a pharmaceutically acceptable salt or solvate thereof, wherein:
A is a pyrimidinone optionally substituted with 1 to 2 groups of $R^1$;
Y is pyrazolyl optionally substituted with 1 to 2 groups of $R^b$;
$R^1$ is selected from the group consisting of hydrogen, $C_{1-6}$alkyl, $C_{3-10}$cycloalkyl, and $(CH_2)_nC_{6-10}$aryl, said alkyl and aryl optionally substituted with one to three groups of $R^a$;
$R^2$ is selected from the group consisting of —C(=O)—, and $CR^xR^y$,
$R^x$ and $R^y$ are independently selected from the group consisting of H, $(CH_2)_nOR$, $C_{1-6}$alkyl, $C(O)OR$ and $N(R)_2$, said alkyl optionally substituted with one to three groups of $R^a$;
or $R^x$ and $R^y$ can combine with the carbon atom to which they are attached to form a group selected from —O—, $C_{2-6}$ alkenyl, $C_{3-6}$ cycloalkyl and $C_{3-6}$ heterocyclyl;
R represents H, or $C_{1-6}$alkyl,
$R^3$ is $C_{4-10}$heterocyclyl or $C_{6-10}$ aryl, said heterocyclyl and aryl optionally substituted with one to three groups of $R^a$;
or $R^2$ and $R^3$ can combine to form a $C_{3-10}$ heterocyclyl, said heterocyclyl optionally substituted with one to three groups of $R^a$;
$R^a$ is selected from the group consisting of H, halo, CN, $C_{1-6}$alkyl, $(CH_2)_nOR$, $(O)_pC_{1-4}$haloalkyl, $C(O)OR$, —$O(CH_2)_nN(R)_2$, $(CHR)_nN(R)_2$, $NO_2$, $SCF_3$, $S(O)_sCF_3$, $S(O)_sR$, $SF_5$, $C_{3-10}$cycloalkyl, $C_{5-10}$heterocyclyl, and $C_{6-10}$aryl, said alkyl, cycloalkyl, heterocyclyl and awl optionally substituted with one to three groups of $R^b$;
$R^b$ is selected from the group consisting of H, halo, $C_{1-6}$alkyl, $(CH_2)_nOR$, and $(O)_pC_{1-4}$haloalkyl;
n represents 0, 1, 2, 3, or 4;
s represents 0, 1, or 2; and
p represents 0 or 1.

An embodiment of the invention of formula I is realized when the pyrimidinone A is represented by structural formula A1:

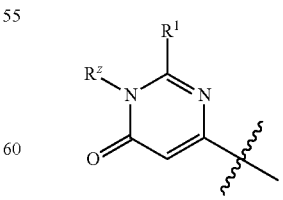

wherein $R^1$ is as originally described and $R^z$ represents H, or $C_{1-6}$alkyl.

An embodiment of the invention of formula I is realized when $R^z$ in A1 is hydrogen.

An embodiment of the invention of formula I is realized when $R^z$ in A1 is $C_{1-6}$alkyl Another embodiment of the invention of formula I is realized when Y is pyrazolyl represented by the group consisting of:

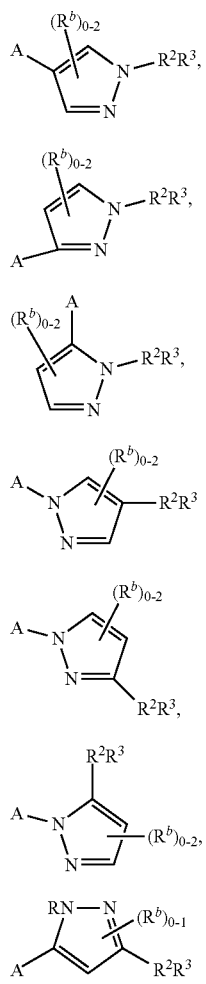

wherein R, $R^2$ and $R^3$ are as originally described and $R^b$ is hydrogen or $C_{1-6}$alkyl.

An aspect of this subembodiment of the invention of formula I is realized when Y is (a), (b), (c), (d), (e), (f), or (g) and the number of $R^b$ is 0-1. Another aspect of this subembodiment of the invention of formula I is realized when Y is (a). Another aspect of this subembodiment of the invention of formula I is realized when Y is (b). Another aspect of this subembodiment of the invention of formula I is realized when Y is (c). Another aspect of this subembodiment of the invention of formula I is realized when Y is (d). Another aspect of this subembodiment of the invention of formula I is realized when Y is (e). Another aspect of this subembodiment of the invention of formula I is realized when Y is (f). Another aspect of this subembodiment of the invention of formula I is realized when Y is (g).

Another embodiment of the invention is realized when $R^1$ is optionally substituted $C_{1-6}$alkyl. An aspect of this embodiment of the invention is realized when $R^1$ is optionally substituted methyl, ethyl, isopropyl, propyl, butyl, isobutyl, pentyl and the like. Still another aspect of this embodiment of the invention is realized when $R^1$ is methyl.

Still another embodiment of the invention is realized when $R^1$ is $C_{3-10}$ cycloalkyl. An aspect of this embodiment of the invention is realized when $R^1$ is cyclopropyl, cyclobutyl, cyclopentyl, cyclohexyl and the like.

Yet another embodiment of the invention is realized when $R^1$ is $(CH_2)_nC_{6-10}$ aryl. An aspect of this embodiment of the invention is realized when the aryl of $R^1$ is optionally substituted phenyl.

Still another embodiment of this aspect of the invention is realized when $R^2$ is —C(=O)—.

Another embodiment of this aspect of the invention is realized when $R^2$ is $CR^xR^y$. Another embodiment of the invention is realized when one of $R^x$ and $R^y$ is hydrogen and the other is selected from the group consisting of $(CH_2)_nOR$, $C_{1-6}$alkyl, C(O)OR and $N(R)_2$, said alkyl optionally substituted with one to three groups of $R^a$. Another embodiment of the invention is realized when $R^x$ and $R^y$ are independently selected from selected from the group consisting of H, methyl, ethyl, propyl, isopropyl, butyl, isobutyl, pentyl, $(CH_2)_nOH$, C(O)OR, $NHCH_3$, $NH_2$, $NHCH_2CH_3$, $OCH_3$, $O(CH_2)_nCH_3$, said methyl, ethyl, propyl, isopropyl, butyl, isobutyl, and pentyl optionally substituted with 1 to 3 groups of OH.

Still another embodiment of the invention is realized when $R^x$ and $R^y$ together with the carbon atom to which they are attached combined to form a group selected from —C(=O)—, $C_{3-6}$ cycloalkyl and $C_{3-6}$ heterocyclyl. An aspect of this aspect of the invention is realized when $R^x$ and $R^y$ together with the carbon atom to which they are attached form —C(=O). Another aspect of this aspect of the invention is realized when $R^x$ and $R^y$ together with the carbon atom to which they are attached form $C_{3-6}$ cycloalkyl, selected from the group consisting of cyclopropyl, cyclobutyl, cyclopentyl and the like. Another aspect of this aspect of the invention is realized when $R^x$ and $R^y$ together with the carbon atom to which they are attached form $C_{3-6}$ heterocyclyl such as tetrahydrofuranyl.

Another embodiment of the invention is realized when $R^2$ is $CR^xR^y$ which is selected from the group consisting of H, $CH(CH_2)_nCH_3$, $CHCH(CH_3)_2$, $CH_2$, —C(=O)—, $CH(CH_2)_nOH$, $C(CH_3)(OH)$, $CHC(O)OCH_3$, $CH(NHCH_3)$, $CH(CH_2)_n(OCH_3)$, cyclobutyl, tetrahydrofuranyl. An aspect of this embodiment of the invention is realized when $R^2$ is $CH_2$, $CH(CH_2)_nCH_3$, or $CHCH_3$. Still another aspect of this embodiment of the invention is realized when $R^2$ is $CHCH_3$.

Still another embodiment of the invention is realized when $R^3$ is optionally substituted $C_{4-10}$heterocyclyl. An aspect of this embodiment of the invention is realized when the heterocyclyl of $R^3$ is selected from the group consisting of optionally substituted dihydroisochromenyl, dihydrobenzofuranyl, pyridyl, tetrahydrofuranyl, tetrahydropyranyl, and piperidinyl. A subembodiment of this aspect of the invention is realized when the heterocyclyl of $R^3$ is optionally substituted dihydroisochromenyl. Another subembodiment of this aspect of the invention is realized when the heterocyclyl of $R^3$ is optionally substituted dihydrobenzofuranyl. Another subembodiment of this aspect of the invention is realized when the heterocyclyl of $R^3$ is optionally substituted pyridyl. Still another subembodiment of this aspect of the invention is realized when the heterocyclyl of $R^3$ is optionally substituted tetrahydrofuranyl. Yet another subembodiment of this aspect of the invention is realized when the heterocyclyl of $R^3$ is optionally substituted tetrahydropyranyl. Still another subembodiment of this aspect of the invention is realized when the heterocyclyl of $R^3$ is optionally substituted piperidinyl.

Yet another embodiment of the invention is realized when $R^3$ is optionally substituted $C_{6-10}$ aryl. An aspect of this embodiment of the invention is realized when the aryl of $R^3$ is optionally substituted phenyl.

Still another embodiment of the invention is realized when $R^2$ and $R^3$ combine to form a $C_{3-10}$ heterocyclyl, said heterocyclyl optionally substituted with one to three groups of $R^a$. An aspect of this embodiment of the invention is realized when $R^2$ and $R^3$ combine to form tetrahydrofuranyl or tetrahydrobenzfuranyl.

Another embodiment of the invention of formula I is realized when $R^a$ is selected from H, OH, halo, $(CH_2)_nCH_3$, $CH(CH_3)_2$, $C(CH_3)_3$, $C(O)OCH_3$, $(CH_2)_nOCH_3$, $OC(CH_3)_2$, $CH_2F$, $CHF_2$, $(CH_2)_nCF_3$, $OCHF_2$, $OCF_3$, $SCH_3$, $SCF_3$, $SF_5$, $SOCF_3$, $SO_2CF_3$, $SO_2CH_3$, $CH_2NH_2$, $(CH_2)_nN(CH_3)_2$, $NO_2$, CN, cyclobutyl, cyclopropyl, phenyl, naphthyl, pyrimidinyl, pyridyl, said groups where appropriate, optionally substituted with one to three groups of $R^b$.

Another embodiment of the invention of formula I is realized when $R^a$ is selected from OH, halo, $(CH_2)_nCH_3$, $CH(CH_3)_2$, $C(CH_3)_3$, $(CH_2)_nOCH_3$, $OC(CH_3)_2$, $CH_2F$, $CF_3$, $OCHF_2$, $OCF_3$, $SCH_3$, $SCF_3$, $SF_5$, $SOCF_3$, $SO_2CF_3$, $SO_2CH_3$, $CH_2NH_2$, $(CH_2)_nN(CH_3)_2$, $NO_2$, CN, cyclobutyl, cyclopropyl, and phenyl, said groups, where appropriate, optionally substituted with one to three groups of $R^b$.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of $R^a$ is 0-1, 0-2, or 0-3.

Still another embodiment of the invention is realized when it is represented by structural formula Ia:

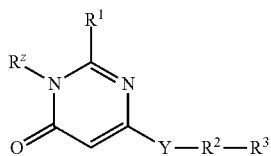

Ia or a pharmaceutically acceptable salt or solvate thereof. An aspect of this invention is realized when Y is selected from the group consisting of

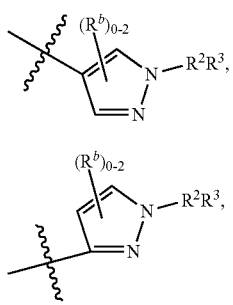

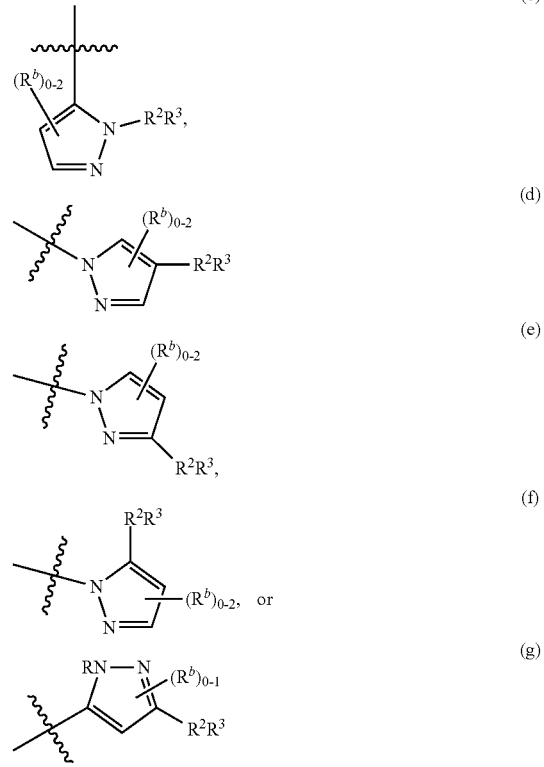

The number of $R^b$ in (a), (b), (c), (d), (e), (f), and (g) is 0 or $R^b$ is not present, $R^z$ is hydrogen, $R^1$ is selected from the group consisting of optionally substituted $C_{1-6}$alkyl cyclopropyl, cyclobutyl, and phenyl and $R^2$ is $CR^xR^y$. Still another aspect of this invention of formula Ia is realized when $R^x$ and $R^y$ of $CR^xR^y$ are independently selected from selected from the group consisting of H, methyl, ethyl, propyl, isopropyl, butyl, isobutyl, pentyl, $(CH_2)_nOH$, $C(O)OR$, $NHCH_3$, $NH_2$, $NHCH_2CH_3$, $OCH_3$, $O(CH_2)_nCH_3$, said methyl, ethyl, propyl, isopropyl, butyl, isobutyl, and pentyl optionally substituted with 1 to 3 groups of OH. Yet another embodiment of this aspect of the invention of formula Ia is realized when $R^x$ and $R^y$ of $CR^xR^y$ together with the carbon atom to which they are attached combined to form a group selected from —C(=O)—, $C_{2-6}$ alkenyl, $C_{3-6}$ cycloalkyl and $C_{3-6}$ heterocyclyl. An embodiment of this aspect of the invention of formula Ia is realized when $R^x$ and $R^y$ together with the carbon atom to which they are attached form —C(=O), cyclopropyl, cyclobutyl, cyclopentyl, or tetrahydrofuranyl.

Still another embodiment of the aspect of the invention of formula Ia is realized when one of $R^x$ and $R^y$ is hydrogen and the other is selected from the group consisting of methyl, ethyl, propyl, isopropyl, butyl, isobutyl, pentyl, $(CH_2)_nOH$, $C(O)OR$, $NHCH_3$, $NH_2$, $NHCH_2CH_3$, $OCH_3$, $O(CH_2)_nCH_3$, said methyl, ethyl, propyl, isopropyl, butyl, isobutyl, and pentyl optionally substituted with 1 to 3 groups of OH.

Another embodiment of the invention of formula Ia is realized when $R^3$ is optionally substituted dihydroisochromenyl, dihydrobenzofuranyl, dihydroisobenzofuranyl, pyridyl, tetrahydrofuranyl, tetrahydropyranyl, piperidinyl, napthyl, and phenyl. Yet another aspect of the invention of formula Ia is realized when $R^3$ is optionally substituted phenyl. Still another aspect of the invention of formula Ia is realized when $R^3$ is substituted phenyl.

Another aspect of the invention of formula Ia is realized when Y is (a), (b), (c), (d), (e), (f), or (g), the number of $R^b$ is 0-1, or 0, $R^z$ is hydrogen, $R^1$ is selected from the group consisting of optionally substituted $C_{1-6}$ alkyl, cyclopropyl, cyclobutyl, and phenyl, $R^2$ is $CH(CH_2)_nCH_3$, $CHCH(CH_3)_2$, $CH_2$, —C(O)—, $CH(CH_2)_nOH$, $C(CH_3)(OH)$, $CHC(O)OCH_3$, $CH(NHCH_3)$, $CH(CH_2)_n(OCH_3)$, cyclobutyl, tetrahydrofuranyl and $R^3$ is optionally substituted phenyl.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formula I.

Examples of compounds of the invention can be found throughout the specification.

The invention also encompasses pharmaceutical compositions containing a compound of formula I, and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. Co alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

It should be appreciated by any one skilled in the art that the compounds of this invention can exist in several tautomeric forms as shown below:

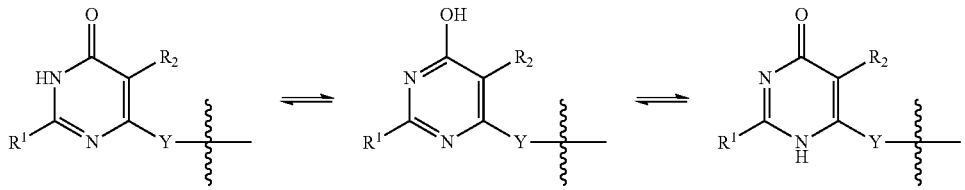

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and Ia and they are intended to represent all possible tautomeric forms for these compounds without regard to what actually is the predominant tautomeric form in existence for a particular compound.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I and Ia. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I and Ia can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br3=pyridine hydrobromide perbromide
r.t./RT=room temperature
rac. racemic
T3P=2,4,6-Tripropyl-1,3,5,2,4,6-trioxatriphosphinane 2,4,6-trioxide
TBAF=tetrabutylammonium fluoride
TFA=trifluoroacetic acid
TfO=trifluoromethanesulfonate=triflate
THF=tetrahydrofuran
TLC=thin layer chromatography
TMSCl=trimethylsilyl chloride The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

Treating" or "treatment of" a disease state includes: 1 inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "'selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEi's (Aricept (donepezil)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or antianxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

GENERAL

Starting materials used were obtained from commercial sources or prepared in other examples, unless otherwise noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 □M NH₄HCO₃), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

Scheme 1.

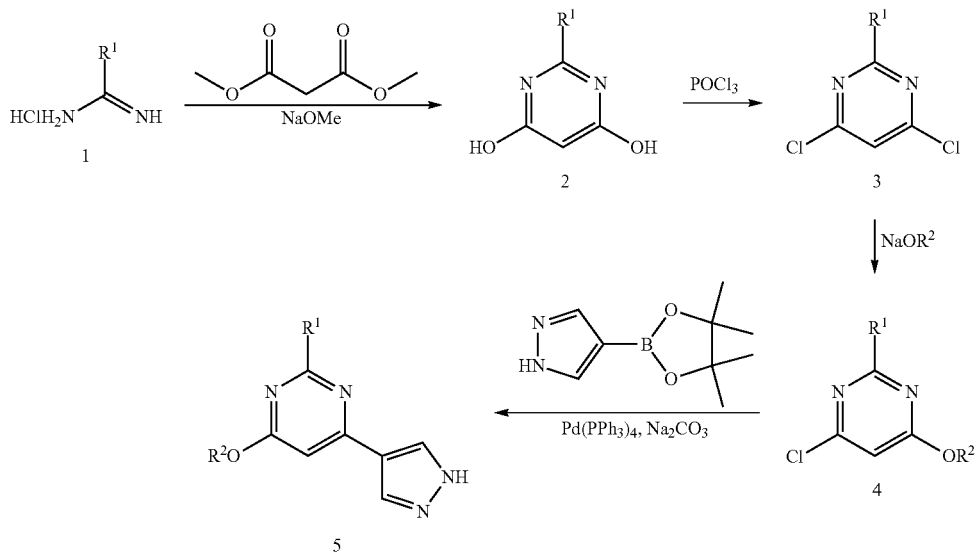

Scheme 1 illustrates the procedures for the syntheses of pyrimidine pyrazoles such as 5 beginning with amidines such as 1. Amidine 1 is converted to pyrimidine diol 2 using dimethyl malonate. Diol 2 is converted to dichloropyrimidine 3 with phosphorus oxychloride. Nucleophilic displacement on 3 with a sodium alkoxide provides intermediate 4 which can be converted to intermediate 5 via a Suzuki coupling with a pyrazole boronate ester.

Scheme 2.

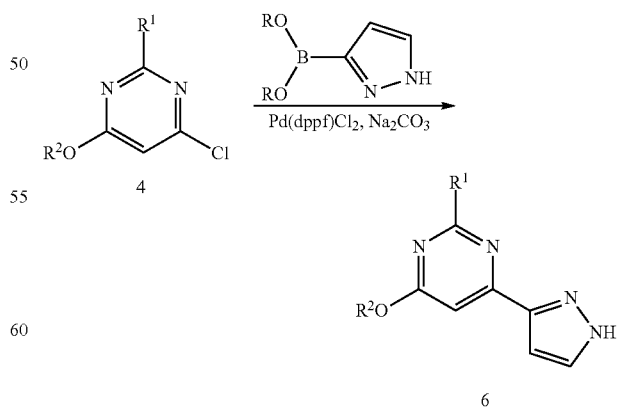

Scheme 2 illustrates a procedure for the synthesis of pyrimidine pyrazoles such as 6 from chloropyrimidines such as 6 via a Suzuki cross-coupling reaction.

Scheme 3.

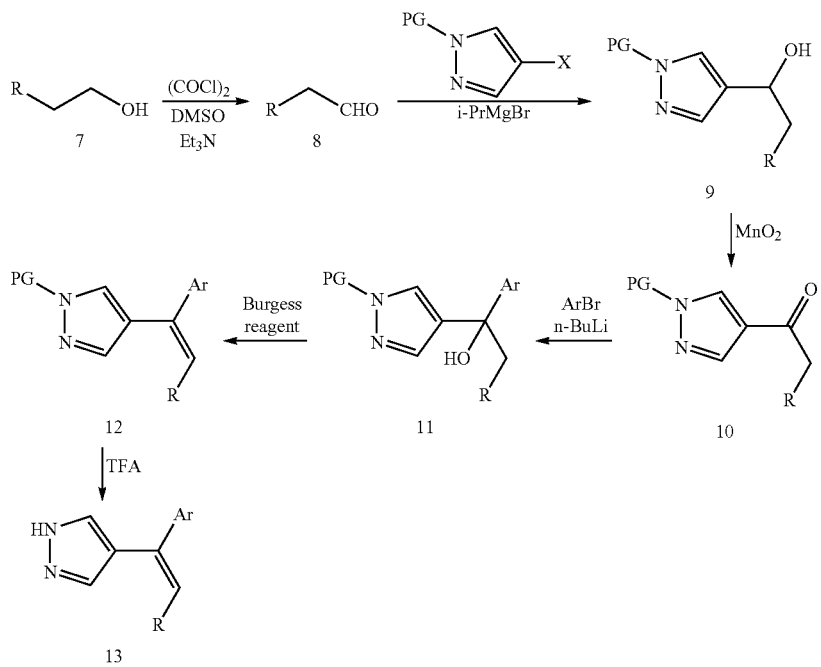

Scheme 3 illustrates a synthetic sequence for the preparation of alkenylpyrazoles such as 13. Alcohol 7 is oxidized to aldehyde 8 using a Swern oxidation reaction. Addition of a Grignard reagent RMgBr to the aldehyde 8 affords the pyrazole alcohol 9. Intermediate 9 is transformed to ketone 10 via an oxidation reaction using $MnO_2$. Addition of an aryllithium reagent to 10 furnishes tertiary alcohol 11, which can be converted to 13 through dehydration with Burgess reagent and subsequent deprotection of 12.

Scheme 4.

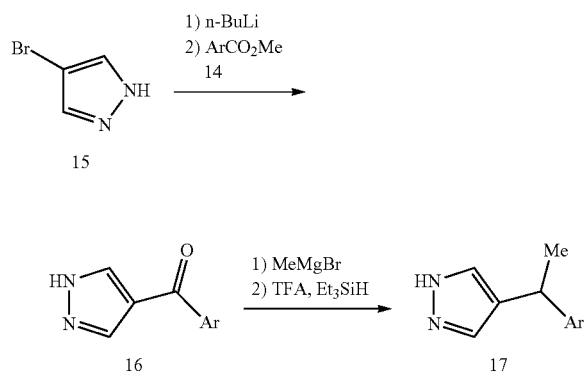

Scheme 4 illustrates a synthetic sequence for the preparation of 4-substituted pyrazoles such as 17 from 4-bromopyrazole and methyl benzoates such as 16. Ketone 16 is obtained from addition of a 4-lithiopyrazole to methylbenzoate 14. Addition of a Grignard reagent to 16, followed by reduction with TFA and triethylsilane furnishes 17.

Scheme 5.

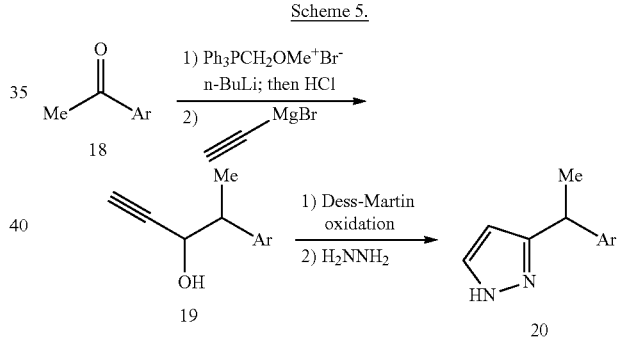

Scheme 5 illustrates a synthetic sequence for the preparation of 3-substituted pyrazoles such as 20 from acetophenones such as 18. Compounds such as 18 can be converted to propargylic alcohol intermediate 19 in three steps. First, the acetophenone is converted to a vinyl ether and then hydrolyzed under acidic conditions to provide an aldehyde intermediate (not shown). Addition of ethynyl magnesium bromide to the aldehyde affords 19. Alkynes such as 19 can then be oxidized to an alkynyl ketone (not shown) which can be converted to the pyrazole 20 through a condensation reaction with hydrazine.

Scheme 6.

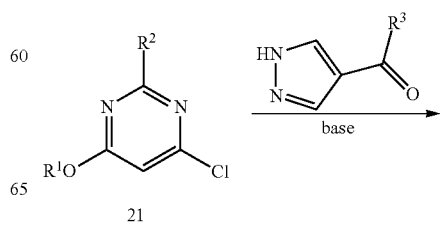

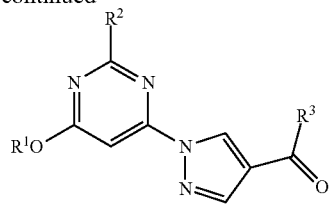

Scheme 6 illustrates a synthetic procedure for the preparation of pyrazolylpyrimidine alkyl ketones such as 22. An $S_NAr$ reaction of 21 with a pyrazolylketone provides intermediate 22.

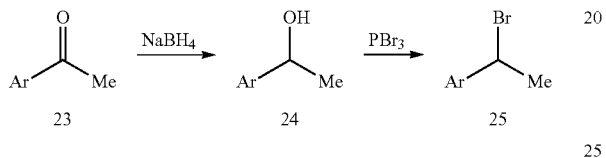

Scheme 7 illustrates a synthetic sequence for the preparation of benzyl bromides such as 25 from acetophenones such as 23. Reduction of 23 with $NaBH_4$ followed by treatment with $PBr_3$ affords the bromide 25.

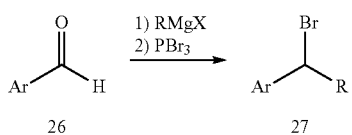

Scheme 8 illustrates a synthetic sequence for the synthesis of benzylic bromides such as 27 from benzaldehyde derivatives such as 26. Grignard addition of alkyl magnesium halides to 26 followed by treatment with a brominating reagent such as phosphorous tribromide delivers bromide 27.

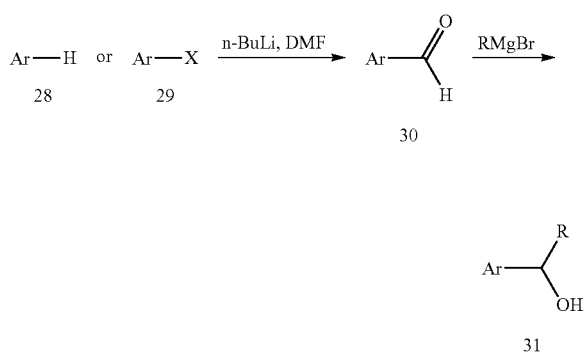

Scheme 9 illustrates a synthetic sequence for the preparation of alcohols such as 31 from arenes such as 28 or 29 or from aldehydes such as 30. The aldehyde 30 is obtained by reaction of n-butyllithium with the aryl hydrocarbon 28 or aryl halide 29 followed by quenching with DMF. Aldehyde 30 is then converted to secondary alcohol 31 via a nucleophilic addition using a Grignard reagent (RMgBr).

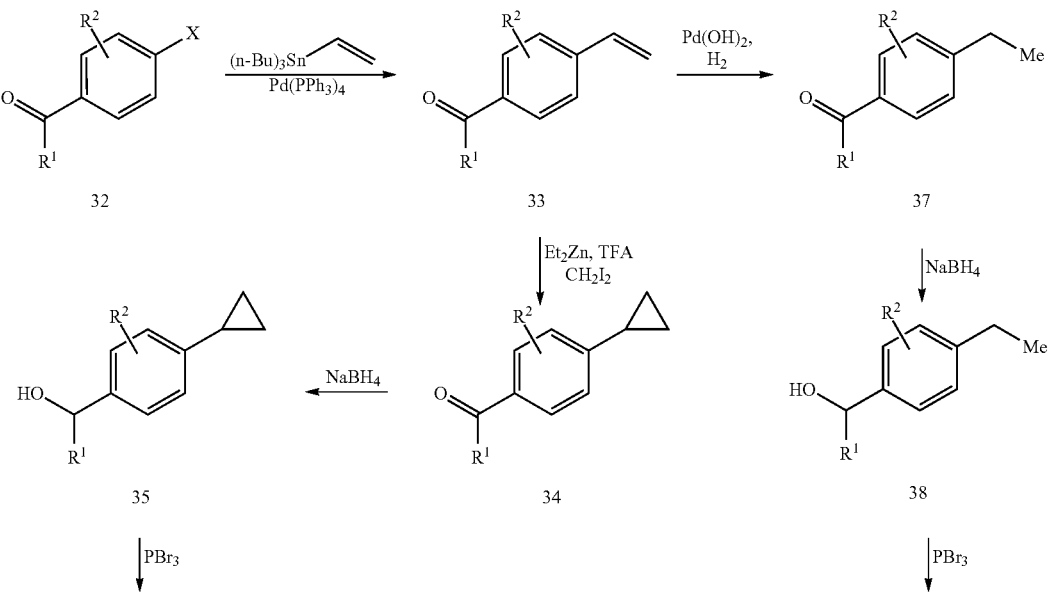

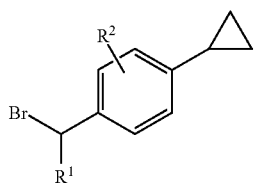

31

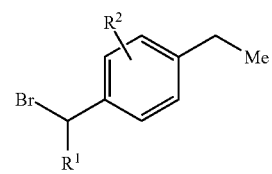

32

Scheme 10 illustrates a synthetic sequence for the preparation of benzylbromides such as 36 and 39 from alkyl ketones such as 32. The aryl halide 32 is converted to olefin 33 via a Stille coupling with a vinyl stannane. Cyclopropanation of olefin 33 using Et$_2$Zn and CH$_2$I$_2$ affords the cyclopropyl acetophenone 34. Alternatively 33 may reduced with Pd(OH)$_2$ and hydrogen to furnish ethyl derivative 37. Both 34 and 37 can be converted to the corresponding benzyl bromides 36 or 39 via reduction with NaBH$_4$ followed by treatment with a brominating reagent such as phosphorous tribromide.

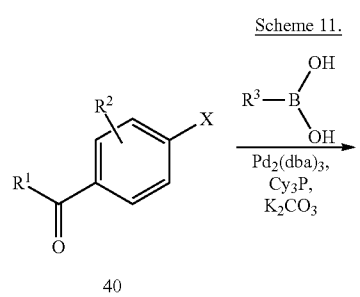

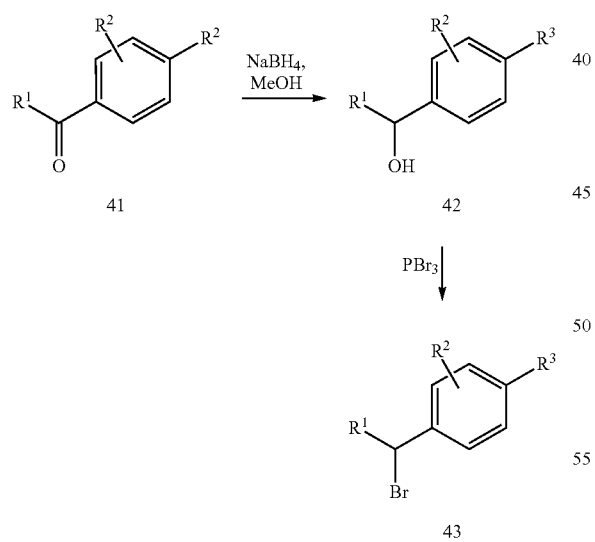

Scheme 11 illustrates a synthetic sequence for the preparation of benzylbromides such as 43 from haloalkyl ketones such as 40. The aryl halide 40 is converted to aryl alkyl ketone 41 using a Suzuki coupling. Ketone 41 is reduced by NaBH$_4$ in MeOH to give secondary alcohol 42 which is converted to benzyl bromide 43 using a brominating reagent such as PBr$_3$.

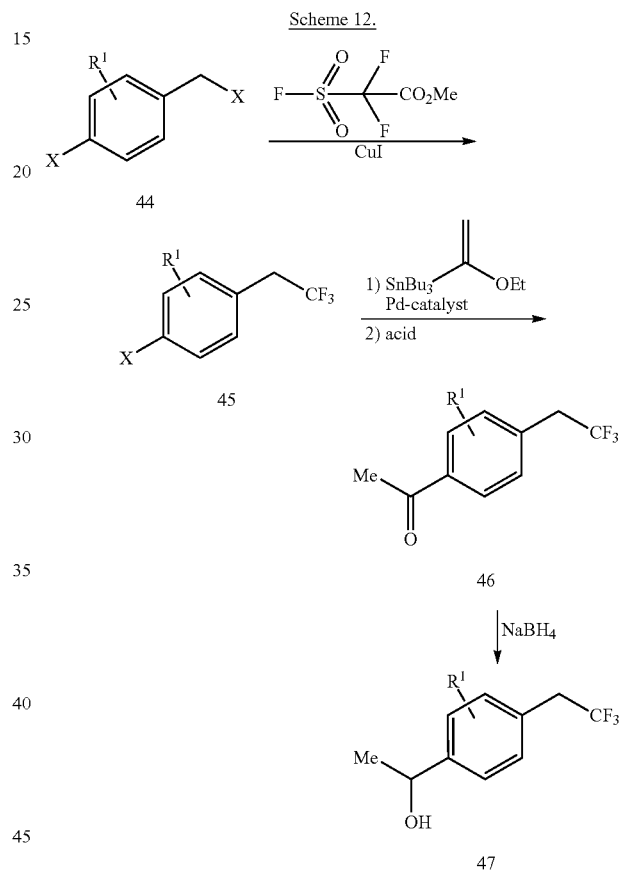

Scheme 12 illustrates a synthetic sequence for the preparation of 1-phenylethanols such as 47 from benzyl halides such as 44. Benzyl halide 44 is converted to trifluoroethylbenzene 45 in the presence of CuI and methyl 2,2-difluoro-2-(fluorosulfonyl)acetate. Aryl halide 45 is converted to acetophenone 46 using a Stille coupling followed by hydrolysis. Then acetophenone 46 is reduced by NaBH$_4$ to give 1-phenylethanol derivatives 47.

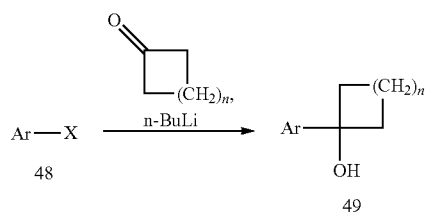

Scheme 13 illustrates a synthetic sequence for the syntheses of tertiary alcohols such as 49 from aryl halide such as 48 via lithiation of 48 with n-butyllithium followed by quenching with a cyclic ketone.

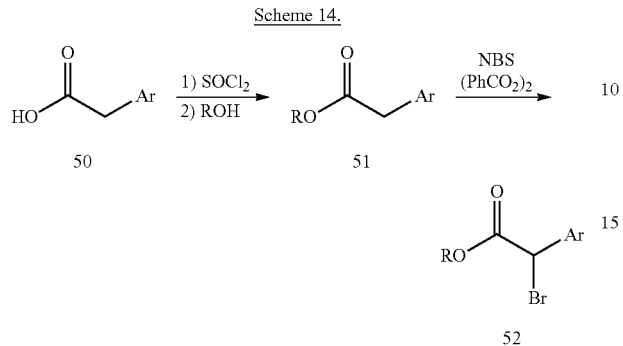

Scheme 14 illustrates a synthetic sequence for the syntheses of α-bromo esters such as 52 from arylacetic acid derivatives such as 50. Compound 50 is converted to an acyl chloride, which is converted to ester 51 by addition of an alcohol. Ester 51 is converted to α-bromo ester 52 via a free radical reaction using N-bromosuccinimide and benzoylperoxide.

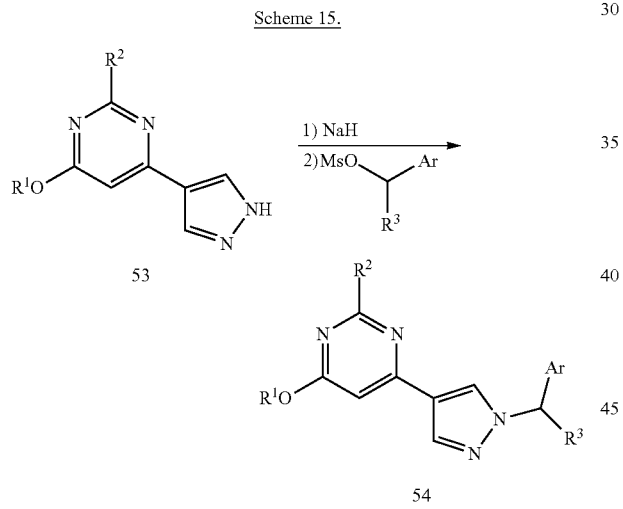

Scheme 15 illustrates a synthetic procedure for the N-alkylation of pyrazoles such as 53 using sodium hydride in the presence of a mesylate to provide compounds such as 54.

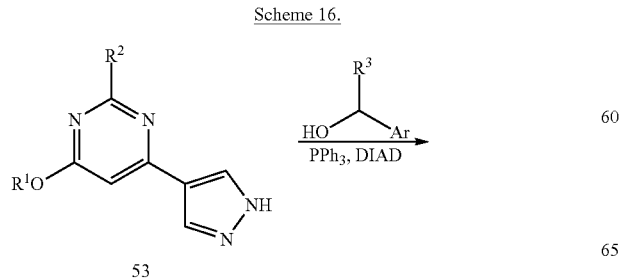

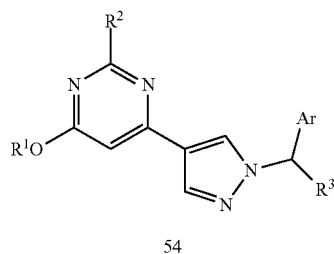

Scheme 16 illustrates a synthetic procedure for the N-alkylation of pyrazoles such as 53 using benzylic alcohols under Mitsunobu conditions to provide compounds such as 54.

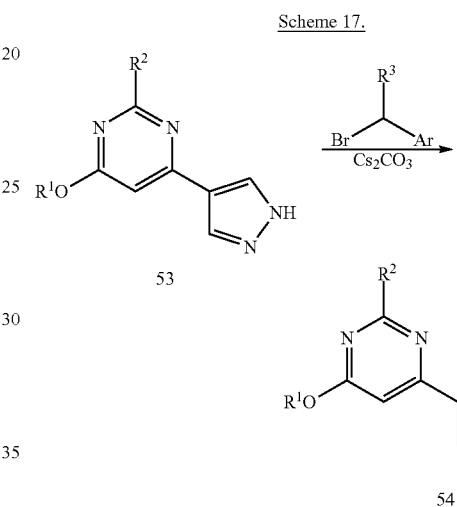

Scheme 17 illustrates a synthetic procedure for the N-alkylation of pyrazoles such as 53 using benzylic bromides and a base such as cesium carbonate to provide compounds such as 54.

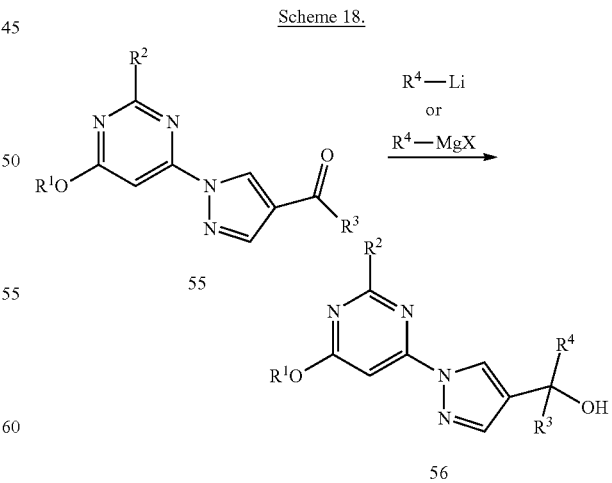

Scheme 18 illustrates a synthetic procedure for the preparation of tertiary alcohols such as 56 from ketones such as 55 via the addition of an organometallic reagent such as a Grignard reagent or organolithium compound.

Scheme 19.

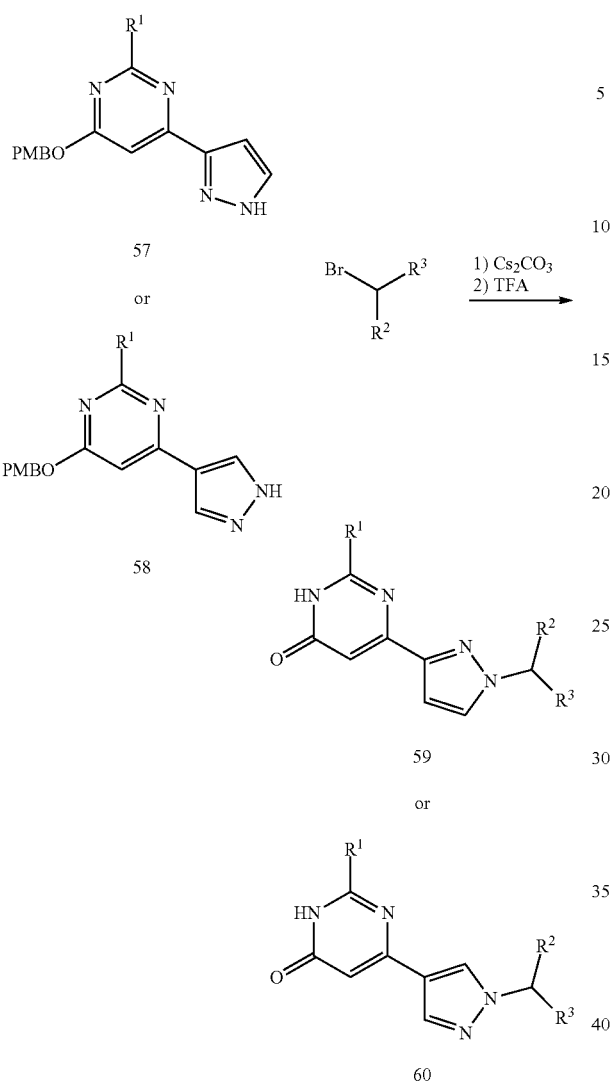

Scheme 19 illustrates a synthetic sequence for the preparation of substituted pyrazoles such as 59 and 60 from alkylation of NH pyrazoles such as 57 and 58 with alkyl bromides.

Scheme 20.

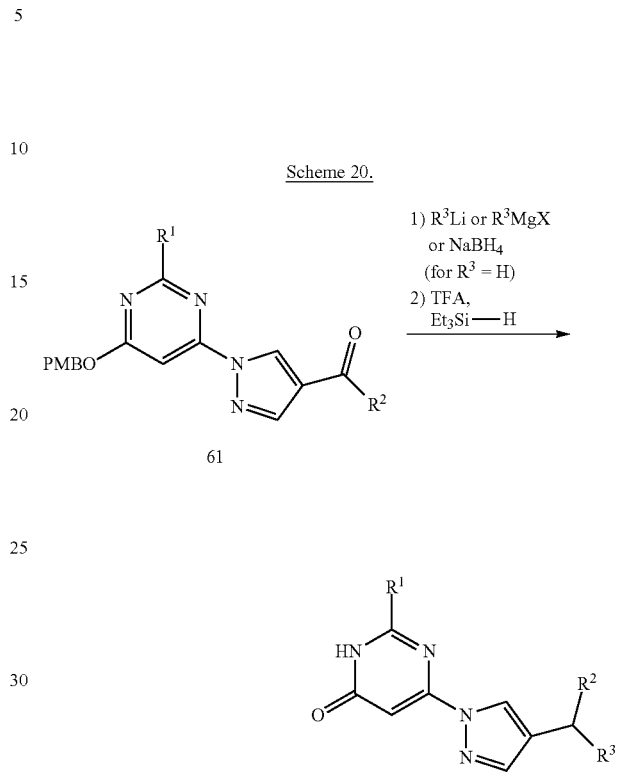

Scheme 20 illustrates a synthetic sequence for the preparation of pyrazolyl pyrimidinone derivatives such as 62 from the addition of nucleophiles to keto-pyrazolylpyrimidones such as 61 followed by ionic reduction with a combination of TFA and triethylsilane.

Scheme 21.

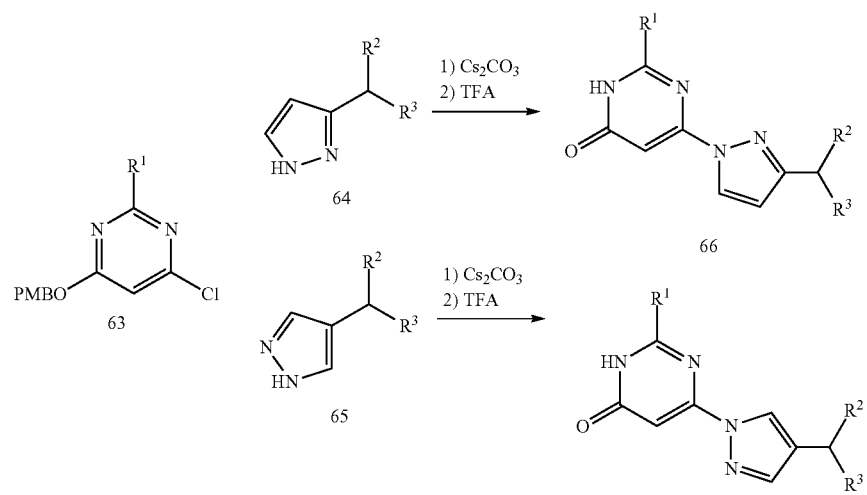

Scheme 21 illustrates a synthetic sequence for the preparation of pyrazolylpyrimidinone derivatives such as 66 and 67 from an $S_NAr$ reaction of N—H pyrazoles such as 64 and 65 with chloropyrimidones such as 63.

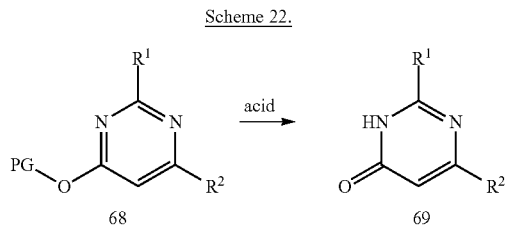

Scheme 22 illustrates a synthetic procedure for the preparation of pyrimidinone derivatives such as 69 by the removal of acid-labile protecting groups (PG) from pyrimidines such as 68.

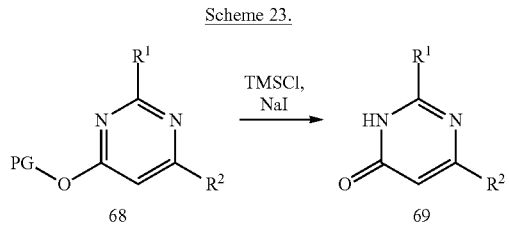

Scheme 23 illustrates a synthetic procedure for the preparation of pyrimidinone derivatives such as 69 by the removal of alkyl-protecting groups (PG) from pyrimidines such as 68 with trimethylsilylchloride and sodium iodide.

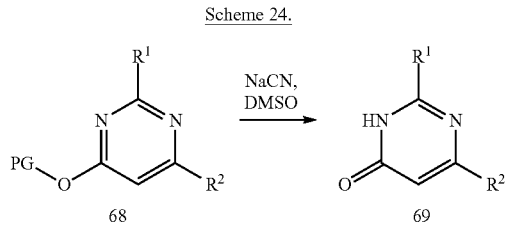

Scheme 24 illustrates a synthetic procedure for the preparation of pyrimidinone derivatives such as 69 by the removal of alkyl-protecting groups (PG) from pyrimidines such as 68 with sodium cyanide.

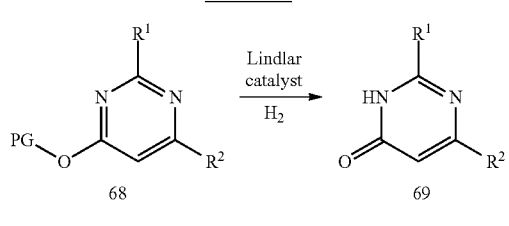

Scheme 25 illustrates a synthetic procedure for the preparation of pyrimidinone derivatives such as 69 by the removal of protecting groups (PG) from pyrimidines such as 68 with hydrogen and a palladium catalyst.

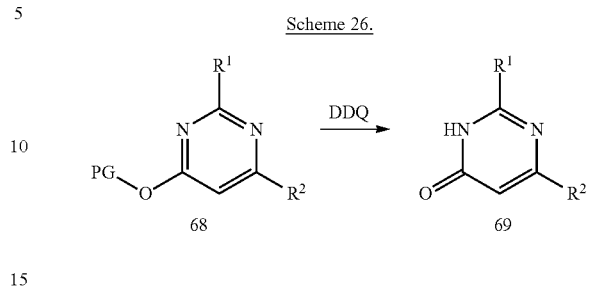

Scheme 26 illustrates a synthetic procedure for the preparation of pyrimidinone derivatives such as 69 by the removal of protecting groups (PG) from pyrimidines such as 68 with an oxidant such as dichlordicyanoquinone.

Scheme 27.

Scheme 27 illustrates a synthetic procedure for the preparation of pyrimidinone derivatives such as 71 by the removal of protecting groups (PG) from pyrimidines such as 70 with iron(III) chloride.

Scheme 28.

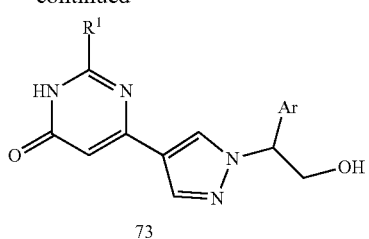

73

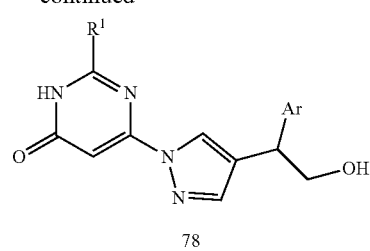

78

Scheme 28 illustrates a synthetic procedure for the preparation of pyrimidinone derivatives via reduction of esters such as 72 to alcohols such as 73.

Scheme 30 illustrates a synthetic sequence for the preparation of pyrimidinone derivatives such as 78 starting with pyrazolylketones such as 76. Addition of an organometallic reagent such as an aryllithium followed by acid-mediated elimination provides olefinic intermediate 77. A hydroboration/oxidation sequence on 77 provides alcoholic derivatives such as 78.

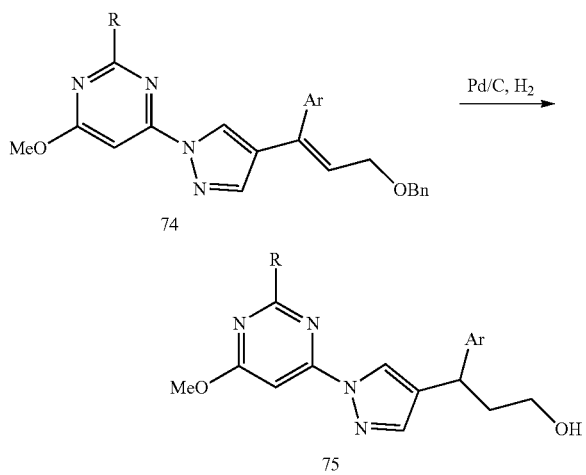

Scheme 29 illustrates a synthetic procedure for the preparation of pyrimidine derivatives such as 75 by the reduction of derivatives such as 74.

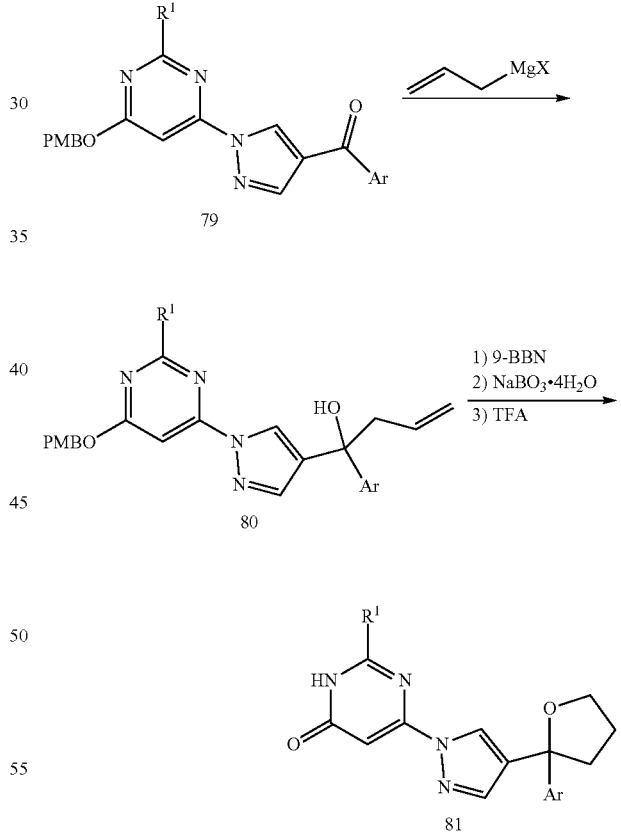

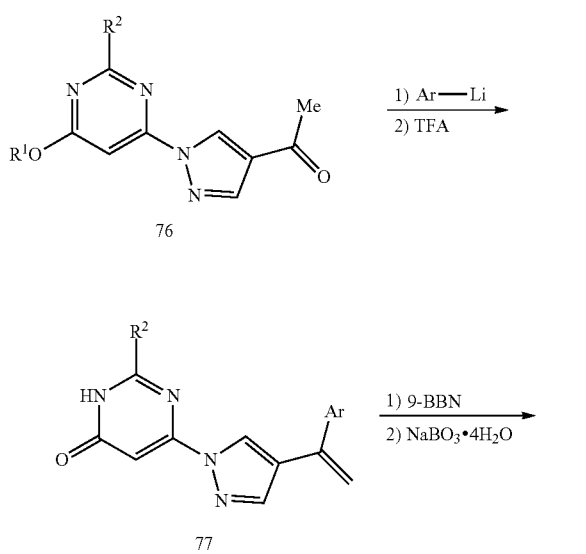

Scheme 31 illustrates a synthetic sequence for the preparation of pyrimidinone derivatives such as 81 starting with pyrazolylketones such as 79. Addition of allyl Grignard reagents to 79, conversion of the olefin to terminal alcohol via hydroboration/oxidation followed by acid-mediated deprotection and cyclization provides 4-tetrahydrofuranylpyrazoles such as 81.

Scheme 32.

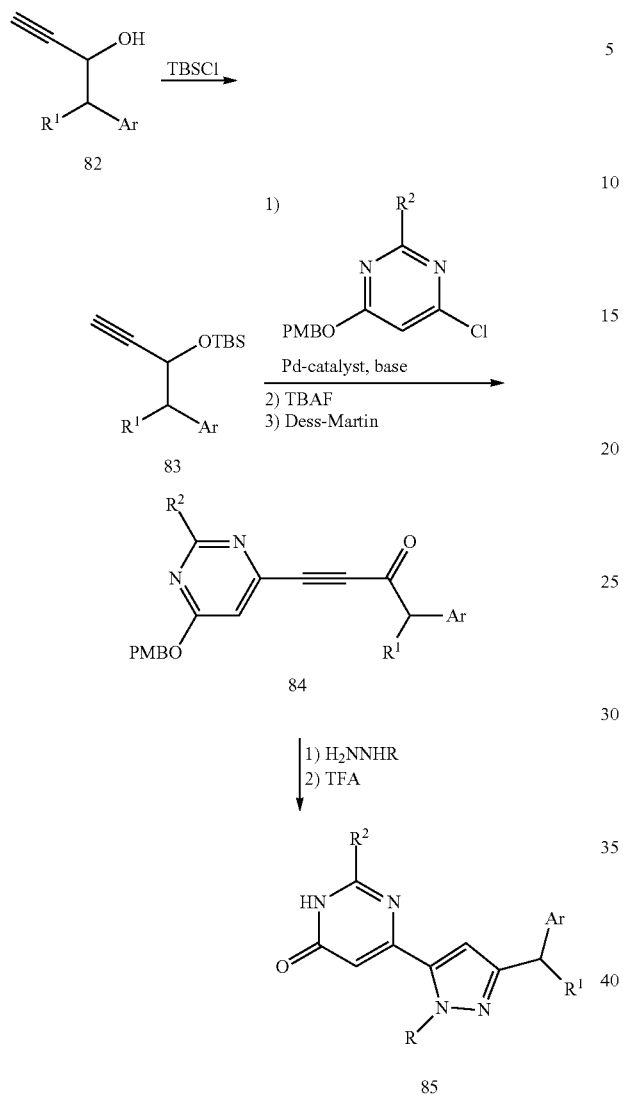

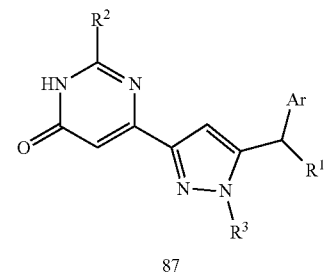

Scheme 32 illustrates a synthetic sequence for the preparation of pyrimidinone derivatives such as 85 starting with propargylic alcohols such as 82. Compound 82 is protected as the TBS ether 83 to enable the 3 step sequence, consisting of Sonogashira coupling, TBS deprotection, and oxidation that provides ynone intermediate 84. Condensation of 84 with a hydrazine followed by deprotection provides 85.

Scheme 33.

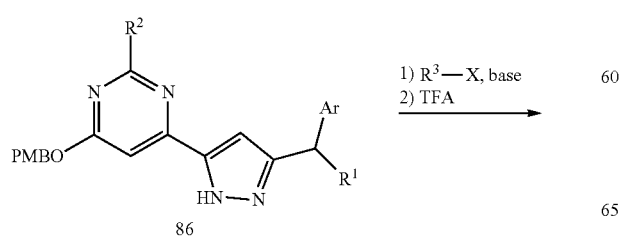

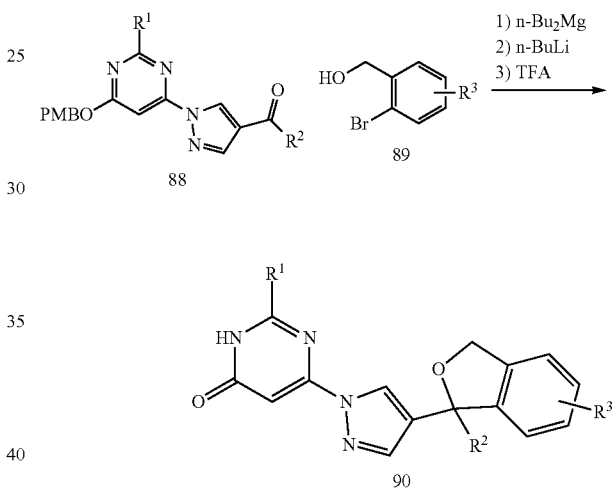

Scheme 33 illustrates a synthetic sequence for the preparation of pyrazoles such as 87 by alkylation of N—H pyrazoles such as 86 followed by deprotection with acid.

Scheme 34 illustrates a synthetic procedure for the preparation of benzodihydrofuranylpyrazolyl-pyrimidones such as 90 from ketones such as 88 and halobenzylic alcohols such as 89. Sequential metallation of 89 with di-n-butylmagnesium and n-butyllithium followed by addition of 88 provides an intermediate which is converted to a derivative such as 90 upon treatment with acid.

Scheme 35.

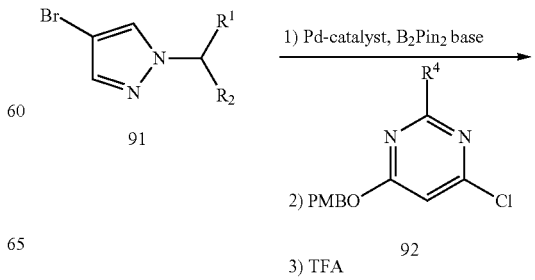

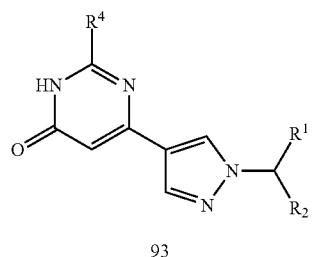

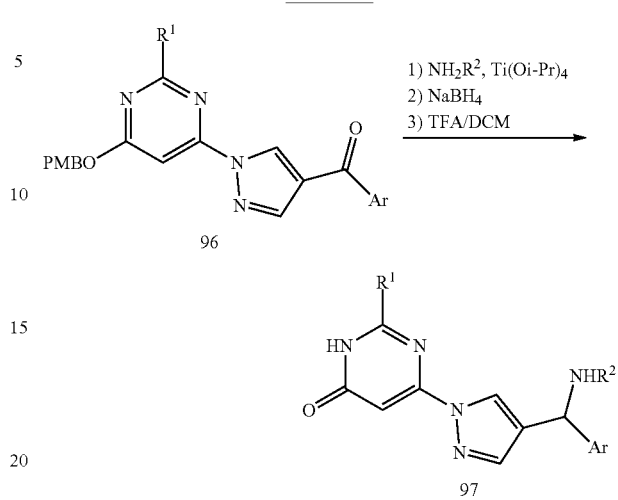

Scheme 35 illustrates a synthetic sequence for the preparation of pyrimidone-pyrazole derivatives such as 93 starting with bromopyrazoles such as 91. Borylation of 91 followed by Suzuki coupling with chloropyrimidine 92 provides the protected pyrimidinone derivative which can be deprotected to provide derivatives such as 93.

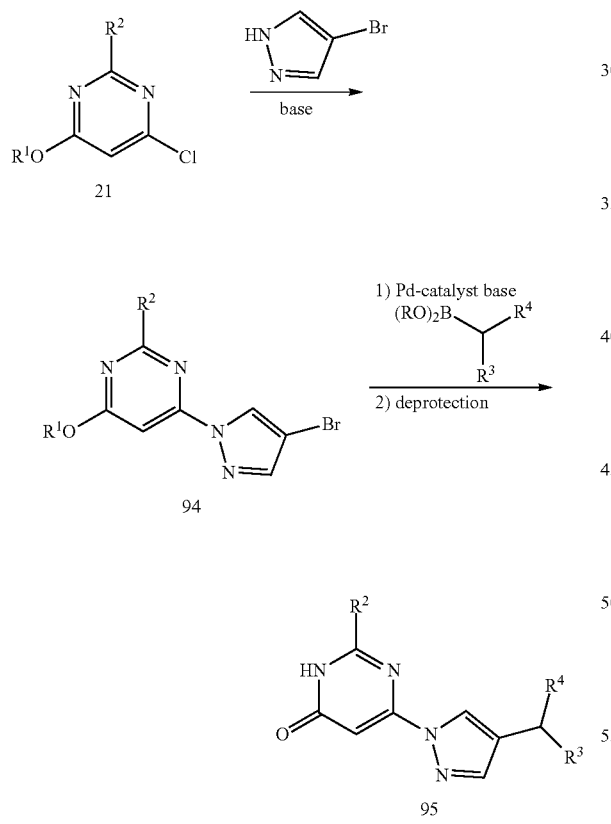

Scheme 36 illustrates a synthetic sequence for the preparation of pyrazolylpyrimidinone derivatives such as 95 starting with chloropyrimidines such as 21. $S_NAr$ reaction of 4-bromopyrazole with 21 provides intermediate 94. Suzuki coupling of 94 with the appropriate boronic acid followed by deprotection provides derivatives such as 95.

Scheme 37 illustrates a synthetic sequence for the preparation of pyrazolylpyrimidones such as 97 via reductive amination of ketones such as 96 followed by deprotection with TFA.

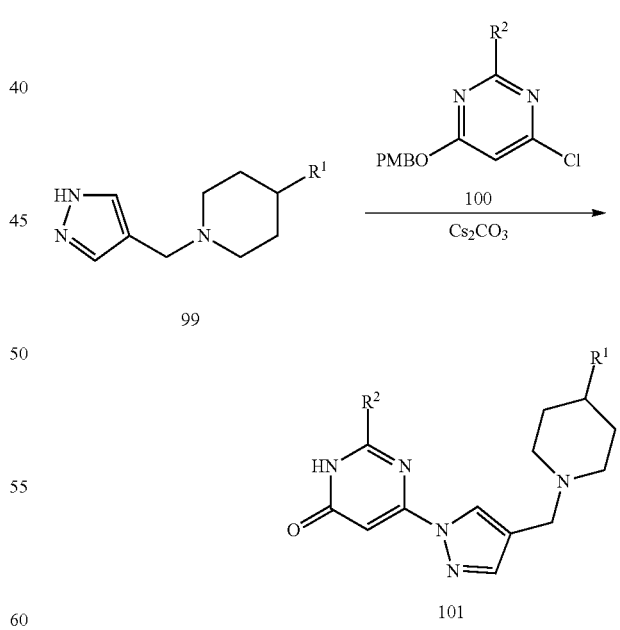

Scheme 38 illustrates a synthetic sequence for the preparation of pyrazolylpyrimidones such as 101 via $S_NAr$ reaction of pyrazole 99 with a chloropyrimidine such as 100. Pyrazole 99 is prepared via a reductive amination of 4-pyrazolecarboxaldehyde 97 with piperidine 98.

PREPARATORY EXAMPLE 1

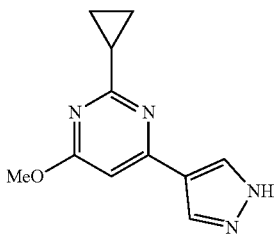 [SMILES: COc1cc(-c2cn[nH]c2)nc(C2CC2)n1]

2-Cyclopropyl-4-methoxy-6-(1H-pyrazol-4-yl)pyrimidine, (Scheme 1)

Step 1. 2-Cyclopropylpyrimidine-4,6-diol

Cyclopropanecarboximidamide hydrochloride (2.00 g, 16.6 mmol) was added to a solution of NaOMe (2.24 g, 41.5 mmol) in MeOH (10.0 mL) at RT. To the mixture was added dimethyl malonate (2.63 g, 19.9 mmol). The reaction mixture was stirred at 60° C. for 18 h. The reaction mixture was cooled to RT, diluted with water (20 mL) and extracted with ethyl acetate (3×40 mL). The combined organic extracts were washed with brine (3×20 mL), dried with anhydrous Na$_2$SO$_4$ and filtered. The filtrate was concentrated under reduced pressure. The title compound was obtained as a solid and was used for the next step without further purification. $^1$H NMR (300 MHz, DMSO-d$_6$) δ: 12.45-11.02 (br, 2H), 5.11 (s, 1H), 1.96-1.87 (m, 1H), 1.03-0.98 (m, 4H).

Step 2. 4,6-Dichloro-2-cyclopropylpyrimidine

To 2-cyclopropylpyrimidine-4,6-diol (0.750 g, 4.93 mmol) was added phosphoryl trichloride (9.0 mL) at RT. The reaction mixture was stirred at 100° C. for 2 h. The resulting solution was cooled and quenched with ice and water (20 mL) and was extracted with ethyl acetate (3×40 mL). The combined organic extracts were washed with brine (3×20 mL), dried with anhydrous Na$_2$SO$_4$, and filtered. The filtrate was concentrated under reduced pressure. The title compound was obtained as a liquid and was used in the next step without further purification. MS=189.1/191.1 (M+1).

Step 3. 4-Chloro-2-cyclopropyl-6-methoxypyrimidine

To a solution of NaOMe (0.143 g, 2.64 mmol) in methanol (25.0 mL) was added 4,6-dichloro-2-cyclopropylpyrimidine (0.500 g, 2.64 mmol) at RT. The reaction solution was stirred at RT for 2 h. The resulting mixture was diluted with water (70 mL) and extracted with ethyl acetate (3×50 mL). The combined organic extracts were washed with brine (50 mL), dried with anhydrous Na$_2$SO$_4$ and filtered. The filtrate was concentrated under reduced pressure. The crude title compound was obtained as a solid and was used in the next step without further purification. MS=185.1/187.1 (M+1).

Step 4. 2-Cyclopropyl-4-methoxy-6-(1H-pyrazol-4-yl)pyrimidine

Sodium carbonate (0.448 g, 4.2 mmol) was added to a solution of 4-chloro-2-cyclopropyl-6-methoxypyrimidine (0.260 g, 1.4 mmol) and 4-(4,4,5,5-tetramethyl-1,3,2-dioxaborolan-2-yl)-1H-pyrazole (0.328 g, 1.7 mmol) in toluene (2.4 mL), ethanol (2.4 mL) and water (0.6 mL) at RT. The reaction mixture was purged with nitrogen 3 times, then to the mixture was added tetrakis(triphenylphosphine) palladium(0) (0.325 g, 0.3 mmol). The resulting mixture was purged with nitrogen 3 times again and stirred under nitrogen atmosphere at 100° C. for 16 h. The reaction mixture was cooled and concentrated under reduced pressure. The residue was diluted with water (10 mL) and extracted with ethyl acetate (3×20 mL). The combined organic extracts were washed with brine (40 mL), dried with anhydrous Na$_2$SO$_4$, and filtered. The filtrate was concentrated under reduced pressure. The residue was purified by silica gel chromatography (0-10% MeOH in DCM) to afford the title compound as a solid. MS=217.2 (M+1).

TABLE 1

The following compounds were prepared using procedures similar to those described in preparatory example 1 using the appropriate starting materials.

| Preparatory Example No. | Structure | IUPAC Name | Exact Mass [M + H]$^+$ or [M + Na]$^+$ |
|---|---|---|---|
| 2 | (Me, PMBO-pyrimidine-pyrazole) | 4-((4-methoxybenzyl)oxy)-2-methyl-6-(1H-pyrazol-4-yl)pyrimidine | Calc'd 297.1, found 297.1 |
| 3 | (Me, MeO-pyrimidine-pyrazole) | 4-methoxy-2-methyl-6-(1H-pyrazol-4-yl)pyrimidine | Calc'd 191.1, found 191.1 |

TABLE 1-continued

The following compounds were prepared using procedures similar to those described in preparatory example 1 using the appropriate starting materials.

| Preparatory Example No. | Structure | IUPAC Name | Exact Mass [M + H]+ or [M + Na]+ |
|---|---|---|---|
| 4 | 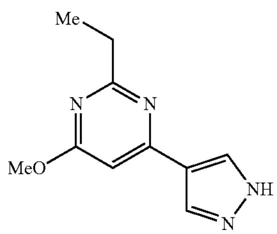 [SMILES: CCc1nc(OC)cc(-c2cn[nH]c2)n1] | 2-ethyl-4-methoxy-6-(1H-pyrazol-4-yl)pyrimidine | Calc'd 205.1, found 205.0 |
| 5 | 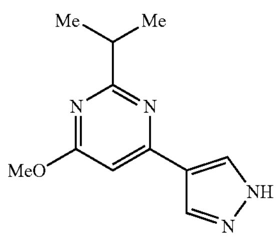 [SMILES: COc1cc(-c2cn[nH]c2)nc(C(C)C)n1] | 2-isopropyl-4-methoxy-6-(1H-pyrazol-4-yl)pyrimidine | Calc'd 219.1, found 219.1 |
| 6 | 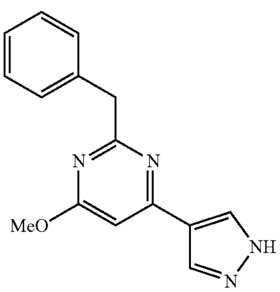 [SMILES: COc1cc(-c2cn[nH]c2)nc(Cc2ccccc2)n1] | 2-benzyl-4-methoxy-6-(1H-pyrazol-4-yl)pyrimidine | Calc'd 267.1, found 267.2 |
| 7 | 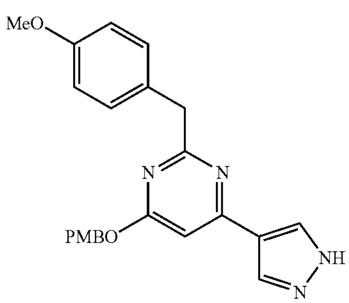 | 2-(4-methoxybenzyl)-4-((4-methoxy-benzyl)oxy)-6-(1H-pyrazol-4-yl)pyrimidine | Calc'd 402.2, Found 403.1 |
| 8 | 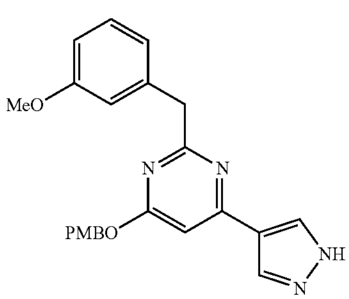 | 2-(3-methoxybenzyl)-4-((4-methoxy-benzyl)oxy)-6-(1H-pyrazol-4-yl)pyrimidine | Calc'd 402.2, Found 403.1 |

TABLE 1-continued

The following compounds were prepared using procedures similar to those described in preparatory example 1 using the appropriate starting materials.

| Preparatory Example No. | Structure | IUPAC Name | Exact Mass [M + H]+ or [M + Na]+ |
|---|---|---|---|
| 9 | MeO, MeO-phenyl-CH2-pyrimidine(PMBO)-pyrazole | 2-(3,4-dimethoxybenzyl)-4-((4-methoxy-benzyl)oxy)-6-(1H-pyrazol-4-yl)pyrimidine | Calc'd 432.18, Found 433.19 |
| 10 | F, MeO-phenyl-CH2-pyrimidine(PMBO)-pyrazole | 2-(3-methoxy-4-fluorobenzyl)-4-((4-methoxy-benzyl)oxy)-6-(1H-pyrazol-4-yl)pyrimidine | Calc'd 420.16, Found 421.02 |
| 11 | MeO, F-phenyl-CH2-pyrimidine(PMBO)-pyrazole | 2-(3-fluoro-4-methoxybenzyl)-4-((4-methoxy-benzyl)oxy)-6-(1H-pyrazol-4-yl)pyrimidine | Calc'd 420.16, Found 421.02 |
| 12 | Me-pyrimidine(PMBO)-pyrazole(Me) | 4-((4-methoxybenzyl)oxy)-2-methyl-6-(3-methyl-1H-pyrazol-4-yl)pyrimidine | Calc'd 311.1, Found 311.0 |

PREPARATORY EXAMPLE 13

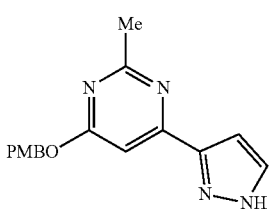

4-((4-Methoxybenzyl)oxy)-2-methyl-6-(1H-pyrazol-3-yl)pyrimidine, (Scheme 2)

To a stirred solution of pyrazole-3-boronic acid (254 mg, 2.267 mmol) and 4-chloro-6-((4-methoxybenzyl)oxy)-2-methylpyrimidine (500 mg, 1.889 mmol) in dioxane (9.4 ml) was added [1,1'-bis(diphenylphosphino)-ferrocene]dichloropalladium(II) (138 mg, 0.189 mmol) and 2 N $Na_2CO_3$ (aq.) (2.83 ml, 5.67 mmol). The reaction mixture was degassed by bubbling nitrogen through the solution and was then stirred at 90° C. overnight. The reaction was cooled to RT and then filtered through a pad of silica gel topped with $Na_2SO_4$ by eluting with ethyl acetate. The residue was purified by silica gel chromatography (0 to 100% ethyl acetate in hexane) to furnish the title compound as a solid. ¹H NMR (500 MHz, CD₃OD) δ: 7.74 (s, 1H), 7.42 (d, J=8.6 Hz, 2H), 7.15 (s, 1H), 6.99 (d, J=2 Hz, 1H), 6.94 (d, J=8.6 Hz, 2H), 5.40 (s, 2H), 3.81 (s, 3H), 2.65 (s, 3H).

PREPARATORY EXAMPLE 14

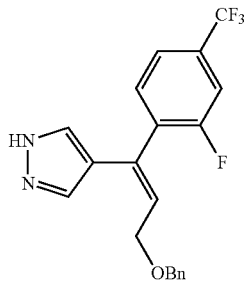 [SMILES: Fc1cc(C(F)(F)F)ccc1/C(=C/COCc1ccccc1)c1cn[nH]c1]

4-(3-(Benzyloxy)-1-(2-fluoro-4-(trifluoromethyl) phenyl)prop-1-en-1-yl)-1H-pyrazole, (Scheme 3)

Step 1. 3-(Benzyloxy)propanal

A solution of DMSO (8.5 mL, 0.120 mol) in dichloromethane (100 mL) was purged with nitrogen 3 times and stirred under nitrogen atmosphere at −78° C. This was followed by dropwise addition of oxalyl chloride (7.64 g, 60.2 mmol) at −78° C. The reaction mixture was stirred under nitrogen atmosphere at −78° C. for 15 minutes. To the reaction mixture was added 3-(benzyloxy)propan-1-ol (5.00 g, 30.1 mmol) in dichloromethane (15 mL). The reaction mixture was stirred at −78° C. for 1 h. Then it was quenched with TEA (33.5 mL, 0.241 mol) and stirred at RT for 10 minutes. The resulting mixture was diluted with brine (100 mL) and extracted with dichloromethane (3×50 mL). The combined organic extracts were dried over anhydrous Na₂SO₄ and filtered. The filtrate was concentrated under vacuum. The residue was purified by silica gel chromatography (0-20% ethyl acetate in petroleum ether) to afford the title compound. ¹H NMR (400 MHz, CDCl₃) δ: 9.83 (t, J=2.0 Hz, 1H), 7.40-7.28 (m, 5H), 4.56 (s, 2H), 3.84 (t, J=6.2 Hz, 2H), 2.74-2.71 (m, 2H).

Step 2. 3-(Benzyloxy)-1-(1-trityl-1H-pyrazol-4-yl) propan-1-ol

A solution of 4-iodo-1-trityl-1H-pyrazole (4.60 g, 10.5 mmol) in THF (50.0 mL) was purged with nitrogen 3 times. This was followed by dropwise addition of isopropylmagnesium bromide (2.9 M in THF, 4.18 mL, 12.1 mmol) at 0° C. The reaction mixture was stirred under a nitrogen atmosphere at 0° C. for 1 h. To the reaction mixture was added a solution of 3-(benzyloxy)propanal (2.08 g, 12.7 mmol) in THF (3.0 mL) at 0° C. The resulting mixture was stirred at RT for 30 minutes. The reaction mixture was quenched with saturated NH₄Cl solution (2.0 mL), diluted with brine (30 mL) and extracted with ethyl acetate (3×10 mL). The combined organic extracts were dried over anhydrous Na₂SO₄ and filtered. The filtrate was concentrated under vacuum. The residue was purified by silica gel chromatography (0-40% ethyl acetate in petroleum ether) to afford the title compound. MS=497.1 (M+1).

Step 3. 3-(Benzyloxy)-1-(1-trityl-1H-pyrazol-4-yl) propan-1-one

To a solution of 3-(benzyloxy)-1-(1-trityl-1H-pyrazol-4-yl)propan-1-ol (3.80 g, 8.0 mmol) in dichloroethane (20.0 mL) was added manganese(IV) oxide (3.48 g, 40.0 mmol) at RT. The reaction mixture was stirred at 85° C. for 16 h. The resulting mixture was filtered. The filter cake was washed with dichloromethane (50 mL). The filtrate was concentrated under vacuum. The residue was purified by column chromatography over silica gel (20% of ethyl acetate in petroleum ether) to afford the title compound as a liquid. MS=495.1 (M+1).

Step 4. 3-(Benzyloxy)-1-(2-fluoro-4-(trifluoromethyl)phenyl)-1-(1-trityl-1H-pyrazol-4-yl)propan-1-ol n-Butyllithium (1.0 M in hexane, 3.8 mL, 9.5 mmol) was added dropwise to a solution of 1-bromo-2-fluoro-4-(trifluoromethyl)benzene (2.57 g, 10.6 mmol) in THF (40 mL) cooled to −78° C. The reaction solution was stirred at −78° C. for 1 h. To the reaction mixture was added a solution of 3-(benzyloxy)-1-(1-trityl-1H-pyrazol-4-yl)propan-1-one (1.00 g, 2.1 mmol) in THF (10 mL) at −78° C. The reaction solution was stirred at RT for 16 h. The resulting mixture was quenched with saturated aqueous NH₄Cl solution (50 mL), diluted with water (100 mL) and extracted with ethyl acetate (3×10 mL). The combined organic extracts were washed with brine (50 mL), dried with anhydrous Na₂SO₄ and filtered. The filtrate was concentrated under reduced pressure. The residue was purified by column chromatography over silica gel (25% ethyl acetate in petroleum ether) to furnish the title compound as a liquid.

MS=659.1 (M+23).

Step 5. 4-(3-(Benzyloxy)-1-(2-fluoro-4-(trifluoromethyl)phenyl)prop-1-en-1-yl)-1-trityl-1H-pyrazole To a solution of 3-(benzyloxy)-1-(2-fluoro-4-(trifluoromethyl)phenyl)-1-(1-trityl-1H-pyrazol-4-yl) propan-1-ol (0.400 g, 0.6 mmol) in toluene (10.0 mL) was added Burgess reagent (0.449 g, 1.9 mmol) at RT. The reaction mixture was stirred at 110° C. for 16 h. The resulting solution was cooled and concentrated under reduced pressure. The crude title compound was obtained as a liquid and was used for next step without further purification.

MS=619.2 (M+1).

Step 6. 4-(3-(Benzyloxy)-1-(2-fluoro-4-(trifluoromethyl)phenyl)prop-1-en-1-yl)-1H-pyrazole To a solution of 4-(3-(benzyloxy)-1-(2-fluoro-4-(trifluoromethyl)phenyl)-prop-1-en-1-yl)-1-trityl-1H-pyrazole (300 mg, 0.5 mmol) in dichloromethane (20 mL) was added TFA (35.0 mg, 0.5 mmol) at RT. The reaction mixture was stirred at RT for 1 h. The resulting solution was concentrated under reduced pressure. The residue was purified by column chromatography over silica gel (30% of ethyl acetate in petroleum ether) to furnish the title compound. MS=377.1 (M+1).

PREPARATORY EXAMPLE 15

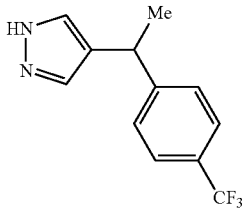 [SMILES: CC(c1ccc(C(F)(F)F)cc1)c1cn[nH]c1]

4-(1-(4-(Trifluoromethyl)phenyl)ethyl)-1H-pyrazole,
(Scheme 4)

Step 1. (1H-Pyrazol-4-yl)(4-(trifluoromethyl)phenyl)methanone

To a −78° C. solution of 4-bromo-1H-pyrazole (2 g, 13.61 mmol) in THF (28.0 ml) under nitrogen was added n-butyllithium (13.06 ml, 32.7 mmol) dropwise over 10 minutes. The reaction was removed from the cold bath and was allowed to stir at RT for 1.5 h. This solution was then cooled to −78° C. and added over 20 minutes to a −78° C. solution of methyl 4-(trifluoromethyl)benzoate (2.63 ml, 16.33 mmol) in THF (28.0 ml) under nitrogen. The reaction was removed from the cold bath after 1 h and was allowed to stir at RT for 1.5 h. The reaction was quenched with saturated $NH_4Cl$ solution (100 mL) and extracted with EtOAc. The organic extract was washed with brine, dried over $Na_2SO_4$ and concentrated. The residue was purified by silica gel chromatography (0-100% EtOAc in hexanes) to afford the title compound. MS=241.0 (M+1).

Step 2. 4-(1-(4-(Trifluoromethyl)phenyl)ethyl)-1H-pyrazole

Methylmagnesium bromide (3 M in ether) (1.041 mL, 3.12 mmol) was added to a 0° C. solution of (1H-pyrazol-4-yl)(4-(trifluoromethyl)phenyl)methanone (500 mg, 2.082 mmol) in THF (5.204 mL). After 1 h, additional methylmagnesium bromide (3 M in ether) (1.041 mL, 3.12 mmol) was added at 0° C. The reaction was warmed to RT and stirred overnight. The reaction was quenched with saturated $NH_4Cl$ solution and the product was extracted with ethyl acetate. The extracts were dried over $Na_2SO_4$, filtered, and concentrated. The resulting tertiary alcohol was then dissolved in DCE (5 mL) and treated with triethylsilane (5 mL, 31.3 mmol) followed by trifluoroacetic acid (5 mL, 64.9 mmol). The mixture was stirred overnight at RT. The reaction was concentrated and diluted with EtOAc. The organic layer was then washed with saturated $NaHCO_3$ solution, then washed with brine and concentrated. The residue was purified by silica gel chromatography (10% MeOH in $CH_2Cl_2$) to furnish the title compound. MS=241.0 (M+1).

PREPARATORY EXAMPLE 16

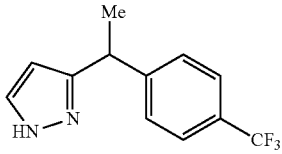

3-(1-(4-(Trifluoromethyl)phenyl)ethyl)-1H-pyrazole,
(Scheme 5)

Step 1. 4-(4-(Trifluoromethyl)phenyl)pent-1-yn-3-ol n-Butyllithium (14.50 ml, 36.3 mmol) was added dropwise to a −78° C. slurry of (methoxymethyl)triphenylphosphonium chloride (12.94 g, 37.8 mmol) in THF (150 ml). The solution was stirred at −78° C. for 30 minutes and then at RT for 1 h. The mixture was recooled to −78° C. and 1-(4-(trifluoromethyl)-phenyl)ethanone (4.70 g, 25 mmol) was added as a solution in THF (20 mL). The mixture was allowed to gradually warm to RT overnight. The reaction was quenched with water (35 mL) and half of the THF was removed by evaporation under reduced pressure. Then HCl (35 ml, 426 mmol) was added at 0° C. and the solution was warmed to 55° C. until the hydrolysis was complete as judged by $^1H$ NMR. The mixture was cooled to RT and the product was extracted with ether. The ethereal extract was washed with water and then saturated aqueous $NaHCO_3$ solution. The extract was dried over $Na_2SO_4$, filtered, and concentrated. The triphenylphosphineoxide and remaining phosphonium salts were precipitated using 20:1 hexane:$Et_2O$. These materials were removed via filtration and the crude solution of the intermediate aldehyde was concentrated. The aldehyde was dissolved in 25 mL THF, cooled to 0° C., and treated with ethynylmagnesium bromide (100 ml, 0.5 M in THF). This mixture was stirred for 1 h at 0° C. and 30 minutes at RT. The reaction was quenched with saturated aqueous $NH_4Cl$ solution and the product was extracted with ether. The ethereal extract was dried over $Na_2SO_4$, filtered, and concentrated. The residue was then purified by silica gel chromatography (0-25% ethyl acetate in hexanes) to provide the title compound as a mixture of diastereomers.
$^1H$ NMR (500 MHz, $CDCl_3$) δ: 7.64-7.62 (m, 2H), 7.50-7.45 (m, 2H), 4.57-4.55 (m, 1H) and 4.53-4.52 (m, 1H), 3.21-3.14 (m, 1H), 2.56 (m, 1H), 2.52 (m, 1H), 1.78 (broad, 1H), 1.49-1.47 (m, 3H).

Step 2. 3-(1-(4-(Trifluoromethyl)phenyl)ethyl)-1H-pyrazole

Dess-Martin Periodinane (1493 mg, 3.52 mmol) was added to a 0° C. mixture of 4-(4-(trifluoromethyl)phenyl)pent-1-yn-3-ol (730 mg, 3.2 mmol) and $NaHCO_3$ (2688 mg, 32.0 mmol) in $CH_2Cl_2$ (20 mL). The reaction was stirred at 0° C. for 1 h. The crude mixture was filtered through silica gel eluting with ether. The eluent was concentrated to yield crude 4-(4-(trifluoromethyl)phenyl)pent-1-yn-3-one which was dissolved in ethanol (20 mL) and treated with hydrazine (0.574 ml, 6.40 mmol). This mixture was stirred overnight at RT. The mixture was concentrated and purified by silica gel chromatography (0-40% ethyl acetate in hexanes) to provide the title compound. MS=241.2 (M+1).

PREPARATORY EXAMPLE 17

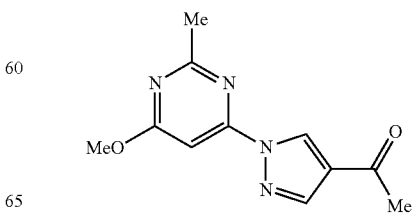

1-(1-(6-Methoxy-2-methylpyrimidin-4-yl)-1H-pyrazol-4-yl)ethanone, (Scheme 6)

To a solution of 4-chloro-6-methoxy-2-methylpyrimidine (1.60 g, 10.1 mmol) and 1-(1H-pyrazol-4-yl)ethanone (1.11 g, 10.1 mmol) in DMF (15.0 mL) was added $Cs_2CO_3$ (9.86 g, 30.2 mmol) at RT. The reaction solution was stirred at 70° C. for 4 h. The resulting mixture was diluted with brine (60 mL) and extracted with ethyl acetate (3×60 mL). The combined organic extracts were dried with anhydrous $Na_2SO_4$ and filtered. The filtrate was concentrated under reduced pressure. The crude title compound was obtained as a solid and used in the next step without further purification. MS=233.1 (M+1).

PREPARATORY EXAMPLE 21

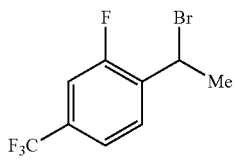

TABLE 2

The following compounds were prepared using procedures similar to those described in preparatory example 17 using the appropriate starting materials.

| Preparatory Example No. | Structure | IUPAC Name | Exact Mass [M + H]+ or [M + Na]+ |
|---|---|---|---|
| 18 | 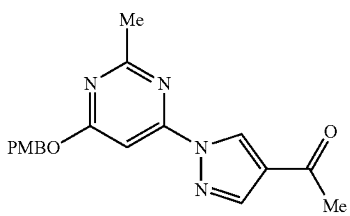 | 1-(1-(6-((4-methoxybenzyl)oxy)-2-methylpyrimidin-4-yl)-1H-pyrazol-4-yl)ethanone | Calc'd 339.1, found 339.1 |
| 19 | 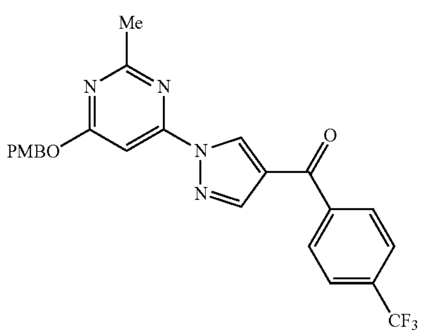 | (1-(6-((4-methoxybenzyl)oxy)-2-methylpyrimidin-4-yl)-1H-pyrazol-4-yl)(4-(trifluoromethyl)phenyl)methanone | Calc'd 469.1, found 469.0 |
| 20 | 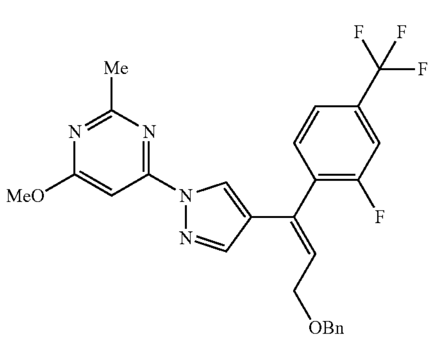 [SMILES: COc1cc(-n2cc(/C(=C\COCc3ccccc3)c3ccc(C(F)(F)F)cc3F)cn2)nc(C)n1] | 4-(4-(3-(benzyloxy)-1-(2-fluoro-4-(trifluoromethyl)phenyl)prop-1-en-1-yl)-1H-pyrazol-1-yl)-6-methoxy-2-methylpyrimidine | Calc'd 499.2, Found 499.1 |

1-(1-Bromoethyl)-2-fluoro-4-(trifluoromethyl)benzene, (Scheme 7)

Step 1. 1-(2-Fluoro-4-(trifluoromethyl)phenyl)ethanol

To a solution of 1-(2-fluoro-4-(trifluoro-methyl)phenyl)ethanone (5 g, 24.26 mmol) in THF (40.4 ml) and MeOH (40.4 ml) at 0° C. was added NaBH$_4$ (2.294 g, 60.6 mmol). The reaction was stirred at 0° C. under nitrogen for 2 h and then quenched with saturated aqueous NaHCO$_3$ and water. This mixture was then extracted with ethyl acetate. The combined organic layers were washed with brine, dried over Na$_2$SO$_4$, and concentrated under reduced pressure to afford the title compound. $^1$H NMR (500 MHz, DMSO-d$_6$): δ 7.76-7.72 (m, 1H), 7.58-7.56 (m, 2H), 5.50 (d, J=4.5 Hz, 1H), 5.04-4.99 (m, 1H), 1.34 (d, J=6.5 Hz, 3H).

Step 2. 1-(1-Bromoethyl)-2-fluoro-4-(trifluoromethyl)benzene

To a flask containing 1-(2-fluoro-4-(trifluoromethyl)phenyl)ethanol (4.65 g, 22.34 mmol) at 0° C. was added tribromophosphine (4.5 ml, 47.7 mmol) dropwise under nitrogen. The reaction was removed from the ice bath after 10 minutes. After 3 h, the reaction was cooled to 0° C. and quenched with saturated aqueous NaHCO$_3$ followed by solid NaHCO$_3$. The mixture was then extracted with EtOAc. The combined organic layers were then washed with brine, dried over Na$_2$SO$_4$ and concentrated under reduced pressure to afford the title compound. $^1$H NMR (500 MHz, CDCl$_3$): δ 7.67 (m, 1H), 7.44 (d, J=8 Hz, 1H), 7.33 (d, J=10 Hz, 1H), 5.46 (q, J=7 Hz, 1H), 2.06 (d, J=7 Hz, 3H).

PREPARATORY EXAMPLE 22

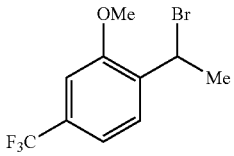 [SMILES: COc1cc(C(F)(F)F)ccc1C(C)Br]

1-(1-Bromoethyl)-2-methoxy-4-(trifluoromethyl)benzene, (Scheme 8)

Methylmagnesium bromide (1.796 ml, 5.39 mmol) was added to a 0° C. solution of 2-methoxy-4-(trifluoro-methyl)benzaldehyde (1.0 g, 4.90 mmol) in THF (25 mL). After 1 h, the reaction was quenched with saturated aqueous NH$_4$Cl and the product was extracted with ethyl acetate. The organic extract was dried over Na$_2$SO$_4$, filtered, and concentrated. The crude material was dissolved in CH$_2$Cl2 (1 mL) and the resulting solution was cooled to 0° C. before the addition of PBr$_3$ (1.016 ml, 10.78 mmol). The reaction was allowed to warm to RT and was stirred overnight. The reaction was added dropwise to a 0° C. rapidly stirring saturated aqueous solution of NaHCO$_3$. The resulting mixture was allowed to stir for 1 h, before the product was extracted with ether. The organic extract was then washed with brine, dried over MgSO$_4$, filtered, and concentrated to provide the title compound. $^1$H NMR (500 MHz, CDCl$_3$): δ 7.65 (d, J=9 Hz, 1H), 7.27 (d, J=9 Hz, 1H), 7.10 (s, 1H), 5.67 (q, J=7 Hz, 1H), 3.96 (s, 3H), 2.05 (d, J=7 Hz, 3H).

TABLE 3

The following compounds were prepared using procedures similar to those described in preparatory example 22 using the appropriate starting materials.

| Preparatory Example No. | Structure | IUPAC Name | $^1$H NMR |
|---|---|---|---|
| 23 | Me, F, Br, Me (structure) | 1-(1-bromoethyl)-2-fluoro-4-methylbenzene | $^1$H NMR (500 MHz, DMSO-d$_6$): δ 7.68 (m, 1H), 7.23 (m, 2H), 5.76 (q, J = 7 Hz, 1H), 2.19 (d, J = 7 Hz, 3H). |
| 24 | Me, Cl, Br, Me (structure) | 1-(2-chloro-4-methylphenyl)-ethanol | $^1$H NMR(500 MHz, DMSO-d$_6$): δ 7.62 (d, J = 8 Hz, 1H), 7.28 (s, 1H), 7.21 (d, J = 8 Hz, 1H), 5.63 (q, J =7 Hz, 1H), ), 2.01 (d, J = 7 Hz, 3H). |
| 25 | Me, CF$_3$, Br, CF$_3$ (structure) | 1-(2,4-bis(trifluoromethyl)phenyl)ethanol | $^1$H NMR (500 MHz. DMSO-d$_6$): δ 8.25 (d, J = 8 Hz, 1H), 7.94 (m, 2H), 5.53 (q, J = 7 Hz, 1H), 2.03 (d, J = 7 Hz, 3H). |

PREPARATORY EXAMPLE 26

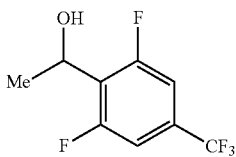

1-(2,6-Difluoro-4-(trifluoromethyl)phenyl)ethanol, (Scheme 9)

Step 1.
2,6-Difluoro-4-(trifluoromethyl)benzaldehyde n-Butyllithium (2.2 M in Hexane, 4.5 mL, 9.89 mmol) was added dropwise to a stirred solution of 1,3-difluoro-5-(trifluoromethyl)benzene (1.50 g, 8.24 mmol) in ethyl ether (70.0 mL) at −78° C. The reaction solution was stirred at −78° C. for 1 h. Then a solution of DMF (3.19 mL, 41.2 mmol) in ethyl ether (5.00 mL) was added to the reaction mixture and stirred for another 1 h at −78° C. The resulting mixture was quenched with saturated aqueous NH$_4$Cl solution (50.0 mL), diluted with water (100 mL) and extracted with ethyl ether (3×50 mL). The combined organic extracts were dried with anhydrous Na$_2$SO$_4$ and filtered. The filtrate was concentrated under reduced pressure. The crude title compound was obtained as a liquid and was used for next step directly without further purification. $^1$H NMR (300 MHz, CDCl$_3$) δ: 10.38 (s, 1H), 7.32-7.23 (m, 2H).

Step 2.
1-(2,6-Difluoro-4-(trifluoromethyl)phenyl)ethanol

To a solution of 2,6-difluoro-4-(trifluoromethyl)benzaldehyde (1.50 g, 7.14 mmol) in THF (100 mL) was added methylmagnesium bromide (3.0 M in THF, 5.24 mL, 15.7 mmol) under nitrogen atmosphere at 0° C. The reaction mixture was stirred under nitrogen atmosphere for 2 h at 0° C. and stirred for additional 2 h at RT. The resulting mixture was quenched with saturated aqueous NH$_4$Cl (100 mL) at 0° C. and extracted with ethyl ether (3×50 mL). The combined organic extracts were washed with brine (3×50 mL), dried with anhydrous Na$_2$SO$_4$ and filtered. The filtrate was concentrated under reduced pressure. The crude title compound was obtained as a liquid and was used for next step directly without further purification. $^1$H NMR (400 MHz, CDCl$_3$) δ: 7.20-7.14 (m, 2H), 5.28 (q, J=6.8 Hz, 1H), 1.65 (d, J=6.4 Hz, 3H).

TABLE 4

The following compounds were prepared using procedures similar to those described in preparatory example 26 using the appropriate starting materials.

| Preparatory Example No. | Structure | IUPAC Name | $^1$HNMR |
|---|---|---|---|
| 27 | 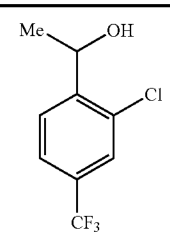 | 1-(2-chloro-4-(trifluoromethyl)phenyl)ethanol | $^1$H NMR (300 MHz, CDCl$_3$) δ: 7.80-7.70 (m, 1H), 7.61-7.50 (m, 2H), 5.33-5.21 (m, 1H), 1.90-1.80 (br, 1H), 1.50 (d, J = 6.3 Hz, 3H). |
| 28 | 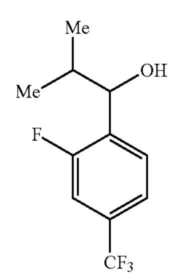 | 1-(2-fluoro-4-(trifluoromethyl)phenyl)-2-methyl-propan-1-ol | $^1$H NMR (300 MHz, CDCl$_3$) δ: 7.65-7.55 (m, 1H), 7.47-7.38 (m, 1H), 7.33-7.21 (m, 1H), 4.81 (d, J = 6.3 Hz, 1H), 2.09-1.89 (m, 1H), 1.91-1.79 (br, 1H), 0.92 (d, J = 8.7 Hz, 3H), 0.87 (d, J = 6.6 Hz, 3H). |
| 29 | 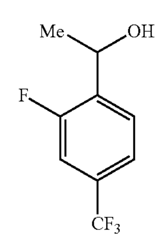 | 1-(2-fluoro-4-(trifluoromethyl)-phenyl)ethanol | $^1$H NMR (300 MHz, MeOD-d$_4$) δ: 7.82-7.73 (m, 1H), 7.56-7.44 (m, 1H), 7.40-7.37 (m, 1H), 5.18 (q, J = 6.5 Hz, 1H), 1.47 (d, J = 6.6 Hz, 3H). |

TABLE 4-continued

The following compounds were prepared using procedures similar to those described in preparatory example 26 using the appropriate starting materials.

| Preparatory Example No. | Structure | IUPAC Name | ¹HNMR |
|---|---|---|---|
| 30 | F-CHF-O-C6H3(F)-CH(OH)Me | 1-(4-(difluoromethoxy)-2-fluorophenyl)-ethanol | ¹H NMR (300 MHz, CDCl₃) δ: 7.55-7.43 (m, 1H), 6.95-6.90 (m, 1H), 6.88-6.81 (m, 1H), 6.50 (t, J = 73.5 Hz, 1H), 5.17 (q, J = 6.5 Hz, 1H), 2.08-1.89 (br, 1H), 1.50 (d, J = 6.3 Hz, 3H). |

PREPARATORY EXAMPLE 31

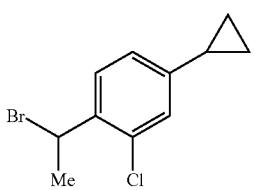 [SMILES: CC(Br)c1ccc(C2CC2)cc1Cl]

1-(1-Bromoethyl)-2-chloro-4-cyclopropylbenzene, (Scheme 10)

Step 1. 1-(2-Chloro-4-vinylphenyl)ethanone

Tributyl(vinyl)stannane (2.45 g, 7.7 mmol) was added to a mixture of 1-(4-bromo-2-chlorophenyl)ethanone (1.50 g, 6.4 mmol) in DMF (10.0 mL) at RT. The reaction mixture was purged with nitrogen 3 times, then to the mixture was added tetrakis(triphenylphosphine) palladium(0) (0.74 g, 0.6 mmol). The reaction mixture was purged with nitrogen 3 times again and stirred under nitrogen atmosphere at 100° C. for 3 h. The resulting mixture was cooled and concentrated under reduced pressure. The residue was diluted with ethyl acetate (300 mL) and washed with brine (2×20 mL), dried with anhydrous Na₂SO₄ and filtered. The filtrate was concentrated under reduced pressure. The residue was purified by silica gel chromatography (100% hexane) to afford the title compound. ¹H NMR (400 MHz, CDCl₃) δ: 7.59 (d, J=8.0 Hz, 1H), 7.47 (s, 1H), 7.36 (d, J=3.2 Hz, 1H), 6.73-6.66 (m, 1H), 5.90-5.85 (m, 1H), 5.45-5.43 (m, 1H), 2.68 (s, 3H).

Step 2. 1-(2-Chloro-4-cyclopropylphenyl)ethanone

A solution of trifluoroacetic acid (1.1 mL, 14.2 mmol) in DCM (10.0 mL) was added dropwise to a solution of diethylzinc (1.0 M in hexane, 14.2 mL, 14.2 mmol) in DCM (40 mL) at 0° C. The reaction suspension was stirred at 0° C. for 10 minutes. To the reaction suspension was added a solution of diiodomethane (1.1 mL, 14.2 mmol) in DCM (2 mL) at 0° C. The reaction suspension was stirred at 0° C. for 10 minutes. Then a solution of 1-(2-chloro-4-vinylphenyl)ethanone (0.570 g, 3.2 mmol) in DCM (2 mL) was added dropwise to the reaction suspension at 0° C. The reaction mixture was stirred at 0° C. for 30 minutes and warmed to RT. After 16 h, the resulting suspension was quenched with saturated aqueous NH₄Cl solution (50 mL) and extracted with dichloromethane (3×50 mL). The combined organic extracts were washed with brine (100 mL), dried with anhydrous Na₂SO₄ and filtered. The filtrate was concentrated under reduced pressure. The residue was purified by silica gel chromatography (100% hexanes) to afford the title compound. ¹H NMR (400 MHz, CDCl₃) δ: 7.53-7.48 (m, 1H), 7.09 (s, 1H), 6.98-6.93 (m, 1H), 2.65 (s, 3H), 1.92-1.86 (m, 1H), 1.08-1.03 (m, 2H), 0.78-0.73 (m, 2H).

Step 3. 1-(2-Chloro-4-cyclopropylphenyl)ethanol

NaBH₄ (78.0 mg, 2.0 mmol) was added to a solution of 1-(2-chloro-4-cyclopropylphenyl)ethanone (0.200 g, 1.03 mmol) in MeOH (5.0 mL). The reaction solution was stirred at RT for 2 h. The resulting solution was concentrated under reduced pressure. The residue was purified by silica gel chromatography (10-20% ethyl acetate in petroleum ether) to furnish the title compound. ¹H NMR (400 MHz, CDCl₃) δ: 7.44 (d, J=8.4 Hz, 1H), 7.03-6.99 (m, 2H), 5.25 (q, J=6.4 Hz, 1H), 2.05 (d, J=6.4 Hz, 3H), 1.90-1.82 (m, 1H), 0.98-0.92 (m, 2H), 0.70-0.66 (m, 2H).

Step 4. 1-(1-Bromoethyl)-2-chloro-4-cyclopropylbenzene

PBr₃ (0.16 mL, 1.7 mmol) was added dropwise to a solution of 1-(2-chloro-4-cyclopropylphenyl) ethanol (0.150 g, 0.8 mmol) in dichloromethane (10.0 ml) at 0° C. The reaction solution was stirred at RT for 16 h. The resulting mixture was diluted with saturated aqueous NaHCO₃ solution (30 mL) and extracted with dichloromethane (3×10 mL). The combined organic extracts were dried with anhydrous Na₂SO₄ and filtered. The filtrate was concentrated. The title compound was obtained as a liquid and used for the next step directly without further purification. ¹H NMR (400 MHz, CDCl₃) δ: 7.49 (d, J=8.4 Hz, 1H), 7.05-6.93 (m, 2H), 5.62 (q, J=6.9 Hz, 1H), 2.03 (d, J=7.2 Hz, 3H), 1.89-1.82 (m, 1H), 0.98-0.93 (m, 2H), 0.72-0.66 (m, 2H).

PREPARATORY EXAMPLE 32

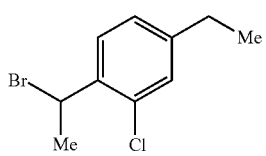 [SMILES: CCc1ccc(C(C)Br)c(Cl)c1]

1-(1-Bromoethyl)-2-chloro-4-ethylbenzene, (Scheme 10)

Step 1. 1-(2-Chloro-4-ethylphenyl)ethan-1-one

Palladium hydroxide on carbon (20%) (22.67 mg, 0.161 mmol) was added to a mixture of 1-(2-fluoro-4-vinylphenyl)ethanone) (265 mg, 1.614 mmol) in ethyl acetate (10 ml). The reaction mixture was degassed with hydrogen 3 times and stirred under hydrogen balloon (1.5 atm) for 1 h at 25° C. The solid was filtered off and the filtrate was concentrated under vacuum. The residue was purified by silica gel column chromatography (20:1 ethyl acetate:petroleum ether) to furnish the title compound.

Step 2. 1-(2-Chloro-4-ethylphenyl)ethan-1-ol

The title compound was prepared according to the procedure detailed in Preparatory Example 31, step 3 using 1-(2-chloro-4-ethylphenyl)ethan-1-one as the starting material.

Step 3. 1-(1-Bromoethyl)-2-chloro-4-ethylbenzene

The title compound was prepared according to the procedure detailed in Preparatory Example 31, step 4 using 1-(2-chloro-4-ethylphenyl)ethan-1-ol as the starting material. $^1$H NMR (400 MHz, DMSO-$d_6$) δ: 7.64 (d, J=8.8 Hz, 1H), 7.33-7.30 (m, 1H), 7.27-7.25 (m, 1H), 5.64 (q, J=6.9 Hz, 1H), 2.61 (q, J=7.6 Hz, 2H), 2.03 (d, J=6.8 Hz, 3H), 1.17 (t, J=7.6 Hz, 3H).

0.4 mmol) were added to a mixture of 1-(4-bromo-2-fluorophenyl)ethanone (1.50 g, 6.9 mmol) in toluene (20 mL) and water (2 mL) at RT. The reaction mixture was purged with nitrogen 3 times. Then to the mixture was added $Pd_2(dba)_3 \cdot CHCl_3$ (72.0 mg, 0.07 mmol). The resulting mixture was purged with nitrogen 3 times again and refluxed under nitrogen atmosphere for 16 h. The reaction mixture was cooled, diluted with water (30 mL) and extracted with ethyl acetate (3×20 mL). The combined organic extracts were washed with brine (3×50 mL), dried over anhydrous $Na_2SO_4$, and filtered. The filtrate was concentrated under vacuum. The residue was purified by silica gel chromatography (0-3% ethyl acetate in petroleum ether) to furnish the title compound.

$^1$H NMR (300 MHz, CDCl$_3$) δ: 7.80-7.72 (m, 1H), 6.90 (dd, J=8.1 Hz, J=1.5 Hz, 1H), 6.77 (dd, J =12.6 Hz; J=1.8 Hz, 1H), 2.60 (s, 3H), 1.99-1.81 (m, 1H), 1.14-1.00 (m, 2H), 0.80-0.75 (m, 2H).

Step 2. 1-(4-Cyclopropyl-2-fluorophenyl)ethanol

The title compound was prepared using procedures similar to those described in step 3 of Preparatory Example 31 using 1-(4-cyclopropyl-2-fluorophenyl)ethanone to afford the title compound as a liquid. $^1$H NMR (300 MHz, CDCl$_3$)

TABLE 5

The following compounds were prepared using procedures similar to those described in preparatory example 32 using appropriate starting materials.

| Preparatory Example No. | Structure | IUPAC Name | $^1$H NMR |
|---|---|---|---|
| 33 | Br–CH(Me)–C6H3(F)–CH2Me | 1-(1-bromoethyl)-4-ethyl-2-fluorobenzene | $^1$H NMR (300 MHz, CDCl$_3$) δ: 7.45-7.35 (m, 1H), 7.00-6.92 (m, 1H), 6.87 (d, J = 11.4 Hz, 1H), 5.48 (q, J = 6.9 Hz, 1H), 2.63 (q, J = 7.6 Hz, 2H), 2.04 (d, J = 6.9 Hz, 3H), 1.23 (t, J = 7.7 Hz, 3H). |

PREPARATORY EXAMPLE 34

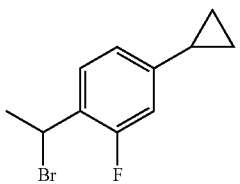

1-(1-Bromoethyl)-4-cyclopropyl-2-fluorobenzene, (Scheme 11)

Step 1. 1-(4-Cyclopropyl-2-fluorophenyl)ethanone

Cyclopropylboronic acid (0.742 g, 8.64 mmol), $K_2CO_3$ (2.87 g, 20.7 mmol) and tricyclohexylphosphine (0.116 g, δ: 7.36-7.22 (m, 1H), 6.88 (dd, J=8.1 Hz; J=1.5 Hz, 1H), 6.70 (dd, J=11.7 Hz; J=1.5 Hz, 1H), 5.16 (q, J=6.6 Hz, 1H), 1.92-1.83 (m, 1H), 1.50 (d, J=6.6 Hz, 3H), 1.00-0.89 (m, 2H), 0.75-0.65 (m, 2H).

Step 3. 1-(1-Bromoethyl)-4-cyclopropyl-2-fluorobenzene

The title compound was prepared using procedures similar to those described in step 4 of Preparatory Example 31 using 1-(4-cyclopropyl-2-fluorophenyl)ethanol (60.0 mg, 0.333 mmol) and PBr$_3$ (0.198 g, 0.732 mmol) in DCM (2.0 mL) to afford the title compound as a liquid. $^1$H NMR (300 MHz, CDCl$_3$) δ: 7.40-7.31 (m, 1H), 6.90-6.85 (m, 1H), 6.73-6.68 (m, 1H), 5.46 (q, J=7.0 Hz, 1H), 2.05 (d, J=6.9 Hz, 3H), 1.91-1.72 (m, 1H), 1.03-0.94 (m, 2H), 0.77-0.62 (m, 2H).

TABLE 6

The following compounds were prepared using procedures similar to those described in preparatory example 34 using the appropriate starting materials.

| Preparatory Example No. | Structure | IUPAC Name | ¹HNMR |
|---|---|---|---|
| 35 | 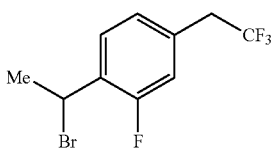 | 1-(1-bromo-ethyl)-4-cyclopropyl-2-methylbenzene | ¹H NMR (300 MHz, CDCl$_3$) δ: 7.43 (d, J = 8.1 Hz, 1H), 6.92 (d, J = 8.1 Hz, 1H), 6.86 (s, 1H), 5.42 (q, J = 6.9 Hz, 1H), 2.37 (s, 3H), 2.07 (d, J = 6.6 Hz, 3H), 1.89-1.80 (m, 1H), 0.98-0.94 (m, 2H), 0.71-0.62 (m, 2H). |

PREPARATORY EXAMPLE 36

1-(1-Bromoethyl)-2-fluoro-4-(2,2,2-trifluoroethyl)benzene, (Scheme 12)

Step 1. 1-Bromo-2-fluoro-4-(2,2,2-trifluoroethyl)benzene

Copper(I) iodide (0.249 g, 1.3 mmol) was added to a mixture of methyl 2,2-difluoro-2-(fluorosulfonyl)acetate (2.01 g, 10.5 mmol) and 1-bromo-4-(bromomethyl)-2-fluorobenzene (1.40 g, 5.2 mmol) in NMP (10.0 mL) at RT. The reaction mixture was purged with nitrogen 3 times and stirred under nitrogen atmosphere at 80° C. for 16 h. The resulting mixture was cooled, diluted with saturated aqueous NH$_4$Cl solution (100 mL) and extracted with dichloromethane (3×30 mL). The combined organic extracts were washed with brine (50 mL), dried over anhydrous Na$_2$SO$_4$, and filtered. The filtrate was concentrated under reduced pressure. The residue was purified by silica gel chromatography (100% hexane) to furnish the title compound. ¹H NMR (400 MHz, CD$_3$OD) δ: 7.66-7.50 (m, 1H), 7.31-7.24 (m, 1H), 7.18-7.12 (m, 1H), 3.55 (q, J=10.9 Hz, 2H).

Step 2. 1-(2-Fluoro-4-(2,2,2-trifluoroethyl)phenyl)ethanone

Tributyl(1-ethoxyvinyl)-stannane (0.696 g, 1.9 mmol) was added to a mixture of 1-bromo-2-fluoro-4-(2,2,2-trifluoroethyl)benzene (0.450 g, 1.8 mmol) in toluene (2.0 mL) at RT. The reaction mixture was purged with nitrogen 3 times. Then to the mixture was added tetrakis(triphenylphosphine) palladium(0) (0.202 g, 0.2 mmol). The resulting mixture was purged with nitrogen 3 times again and stirred under nitrogen atmosphere at 120° C. for 16 h. The reaction mixture was cooled and HCl (6.0 M, 5.0 mL) in THF (10 mL) was added. The reaction mixture was stirred at RT for 2 h. The resulting mixture was diluted with ethyl acetate (100 mL) and washed with brine (2×50 mL). The organic mixture was dried over anhydrous Na$_2$SO$_4$ and filtered. The filtrate was concentrated under reduced pressure. The residue was purified by silica gel chromatography (10% ethyl acetate in petroleum ether) to furnish the title compound. ¹H NMR (300 MHz, CDCl$_3$) δ: 7.91-7.84 (m, 1H), 7.19-7.10 (m, 2H), 3.42 (q, J=10.4 Hz, 2H), 2.65 (s, 3H).

Step 3. 1-(2-Fluoro-4-(2,2,2-trifluoroethyl)phenyl)ethanol

The title compound was prepared using procedures similar to those described in step 3 of Preparatory Example 31 using 1-(2-fluoro-4-(2,2,2-trifluoroethyl)phenyl)ethanone (0.220 g, 1.00 mmol) and sodium borohydride (0.113 g, 3.00 mmol) in methanol (10.0 mL) to afford the title compound as a liquid. ¹H NMR (400 MHz, DMSO-d$_6$) δ: 7.55-7.51 (m, 1H), 7.20-7.13 (m, 2H), 5.35-5.21 (br, 1H), 4.97 (q, J=6.3 Hz, 1H), 3.67 (q, J=11.5 Hz, 2H), 1.33 (d, J=6.4 Hz, 3H).

Step 4. 1-(1-Bromoethyl)-2-fluoro-4-(2,2,2-trifluoroethyl)benzene

The title compound was prepared using procedures similar to those described in step 4 of Preparatory Example 31 using 1-(2-fluoro-4-(2,2,2-trifluoroethyl)phenyl)ethanol (0.140 g, 0.63 mmol) and tribromophosphine (0.682 mg, 2.52 mmol) in DCM (10 mL) to afford the title compound as a liquid. ¹H NMR (400 MHz, CDCl$_3$) δ: 7.57-7.48 (m, 1H), 7.15-7.09 (m, 1H), 7.06-7.02 (m, 1H), 5.49 (q, J=4.7 Hz, 1H), 3.38 (q, J=10.7 Hz, 2H), 2.07 (d, J=4.8 Hz, 3H).

TABLE 7

The following compounds were prepared using procedures similar to those described in preparatory example 36 using the appropriate starting materials.

| Preparatory Example No. | Structure | IUPAC Name | ¹HNMR |
|---|---|---|---|
| 37 | 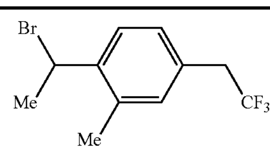 | 1-(1-bromoethyl)-2-methyl-4-(2,2,2-trifluoroethyl)-benzene | ¹H NMR (300 MHz, CDCl$_3$) δ: 7.53 (d, J = 8.1 Hz, 1H), 7.18-7.13 (m, 1H), 7.09 (s, 1H), 5.40 (q, J = 6.9 Hz, 1H), 3.32 (q, J = 10.9 Hz, 2H), 2.41 (s, 3H), 2.08 (d, J = 7.2 Hz, 3H). |

TABLE 7-continued

The following compounds were prepared using procedures similar to those described in preparatory example 36 using the appropriate starting materials.

| Preparatory Example No. | Structure | IUPAC Name | ¹HNMR |
|---|---|---|---|
| 38 | ![structure] | 1-(1-bromoethyl)-4-(difluoromethoxy)-2-methylbenzene | $^1$H NMR (400 MHz, MeOD-$d_4$) δ: 7.38-7.33 (m, 1H), 7.05-6.92 (m, 2H), 6.79 (t, J = 74.4 Hz, 1H), 4.61 (q, J = 6.4 Hz, 1H), 2.36 (s, 3H), 1.38 (d, J = 6.4 Hz, 3H). |
| 39 | ![structure] | 1-(1-bromoethyl)-2-chloro-4-(methoxymethyl)benzene | $^1$H NMR (300 MHz, DMSO-$d_6$) δ: 7.73-7.68 (m, 1H), 7.41 (s, 1H), 7.39-7.32 (m, 1H), 5.65 (q, J = 6.9 Hz, 1H), 4.42 (s, 2H), 3.32 (s, 3H), 2.04 (d, J = 6.9 Hz, 3H). |
| 40 | ![structure] | 1-(1-bromoethyl)-2-fluoro-4-(methoxymethyl)benzene | $^1$H NMR (300 MHz, DMSO-$d_6$) δ: 7.68-7.55 (m, 1H), 7.20-7.11 (m, 2H), 5.61 (q, J = 6.8 Hz, 1H), 4.42 (s, 2H), 3.32 (s, 3H), 2.02 (q, J = 6.9 Hz, 3H). |

PREPARATORY EXAMPLE 41

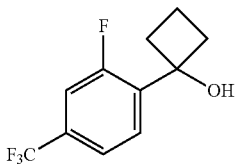

1-(2-Fluoro-4-(trifluoromethyl)phenyl)cyclobutanol, (Scheme 13)

n-Butyllithium (2.5 M in Hexane, 4.7 mL, 11.9 mmol) was added dropwise to a stirring solution of 1-bromo-2-fluoro-4-(trifluoromethyl)benzene (2.40 g, 9.9 mmol) in ethyl ether (80.0 mL) cooled to −78° C. The reaction solution was stirred at −78° C. for 1 h. Then a solution of cyclobutanone (0.831 g, 11.9 mmol) in ethyl ether (10.0 mL) was added to the reaction mixture and stirred for another 1 h at −78° C. The reaction mixture was quenched with saturated aqueous ammonium chloride solution (50.0 mL) and extracted with ethyl ether (3×100 mL). The combined organic extracts were dried with anhydrous Na$_2$SO$_4$ and filtered. The filtrate was concentrated under reduced pressure. The crude title compound was obtained as a liquid and was used for next step directly without further purification. $^1$H NMR (300 MHz, DMSO-$d_6$) δ: 7.72-7.61 (m, 1H), 7.59-7.50 (m, 2H), 5.88-5.62 (br, 1H), 2.65-2.51 (m, 2H), 2.34-2.21 (m, 2H), 2.11-1.92 (m, 2H).

PREPARATORY EXAMPLE 42

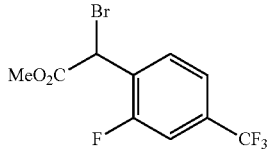

Methyl 2-bromo-2-(2-fluoro-4-(trifluoromethyl)phenyl)acetate, (Scheme 14)

Step 1. Methyl 2-(2-fluoro-4-(trifluoromethyl)phenyl)acetate

To a solution of 2-(2-fluoro-4-(trifluoromethyl)phenyl)acetic acid (2.00 g, 9.0 mmol) in MeOH (3.00 ml) was added SOCl$_2$ (0.66 mL, 9.0 mmol) at RT. The reaction mixture was stirred at RT for 16 h. The reaction mixture was concentrated under vacuum. The residue was diluted with water (50 mL) and extracted by ethyl acetate (3×50 mL). The combined organic extracts were washed with brine (3×50 mL), dried over anhydrous sodium sulfate and filtered. The filtrate was concentrated under vacuum. The residue was purified by silica gel chromatography (0-20% ethyl acetate in petroleum ether) to furnish the title compound. $^1$H NMR (400 MHz, CDCl$_3$) δ: 7.45-7.40 (m, 2H), 7.35 (d, J=10.0 Hz, 1H), 3.75 (s, 3H), 3.66 (s, 2H).

Step 2. Methyl 2-bromo-2-(2-fluoro-4-(trifluoromethyl)phenyl)acetate

To a solution of methyl 2-(2-fluoro-4-(trifluoromethyl)phenyl)acetate (1.14 g, 4.8 mmol) in CCl$_4$ (3 mL) were added NBS (1.03 g, 5.8 mmol) and benzoyl peroxide (0.117 g, 0.5 mmol) at RT. The reaction suspension was stirred at 80° C. for 16 h. The resulting mixture was cooled and was filtered. The filtrate was concentrated under reduced pressure. The residue was purified by silica gel chromatography (0-20% ethyl acetate in petroleum ether) to furnish the title compound. $^1$H NMR (300 MHz, CDCl$_3$) δ: 7.87 (m, 1H), 7.50-7.34 (m, 2H), 5.72 (s, 1H), 3.84 (s, 3H).

added triethylamine (89.0 mg, 0.9 mmol) and methanesulfonyl chloride (60.8 mg, 0.5 mmol) at 0° C. The reaction solution was stirred at RT for 2 h. The resulting mixture was diluted with water (10 mL) and extracted with ethyl acetate (3×10 mL). The combined organic extracts were dried with anhydrous Na$_2$SO$_4$ and filtered. The filtrate was concentrated under reduced pressure to give the crude title compound as a liquid and was used for next step directly without further purification. $^1$H NMR (300 MHz, CDCl$_3$) δ: 7.27-7.22 (m, 2H), 6.12 (q, J=6.8 Hz, 1H), 2.97 (s, 3H), 1.82 (d, J=6.9 Hz, 3H).

TABLE 8

The following compounds were prepared using procedures similar to those described in Preparatory Example 42 using the appropriate starting materials.

| Preparatory Example No. | Structure | IUPAC Name | $^1$HNMR |
|---|---|---|---|
| 43 | MeO-C(=O)-CHBr-(2-Cl,4-CF$_3$-phenyl) | methyl 2-bromo-2-(2-chloro-4-(trifluoromethyl)phenyl)acetate | $^1$H NMR (400 MHz, CDCl$_3$) δ: 7.94 (d, J = 8.4 Hz, 1H), 7.68 (s, 1H), 7.60 (d, J = 8.0 Hz, 1H), 5.91 (s, 1H), 3.85 (s, 3H). |
| 44 | MeO-C(=O)-CHBr-(2-Cl,4-Br-phenyl) | methyl 2-bromo-2-(4-bromo-2-chlorophenyl)acetate | $^1$H NMR (300 MHz, CDCl$_3$) δ: 7.67-7.64 (m, 1H), 7.56 (s, 1H), 7.48-7.44 (m, 1H), 5.83 (s, 1H), 3.81 (s, 3H). |
| 45 | MeO-C(=O)-CHBr-(2-F,4-Br-phenyl) | methyl 2-bromo-2-(4-bromo-2-fluorophenyl)acetate | $^1$H NMR (400 MHz, CDCl$_3$) δ: 7.64-7.60 (m, 1H), 7.38-7.26 (m, 2H), 5.67 (s, 1H), 3.84 (s, 3H). |

PREPARATORY EXAMPLE 46

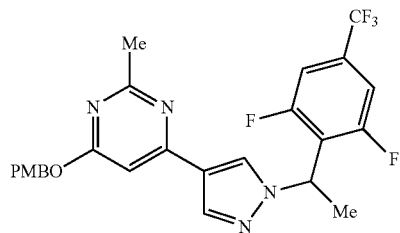

4-(1-(1-(2,6-Difluoro-4-(trifluoromethyl)phenyl)ethyl)-1H-pyrazol-4-yl)-6-((4-methoxybenzyl)oxy)-2-methylpyrimidine, (Scheme 15)

Step 1. 1-(2,6-Difluoro-4-(trifluoromethyl)phenyl)ethyl methanesulfonate

To a solution of 1-(2,6-difluoro-4-(trifluoromethyl)phenyl)ethanol (100 mg, 0.4 mmol) in DCM (1.0 mL) were

Step 2. 4-(1-(1-(2,6-Difluoro-4-(trifluoromethyl)phenyl)ethyl)-1H-pyrazol-4-yl)-6-((4-methoxybenzyl)oxy)-2-methylpyrimidine Sodium hydride (60% in mineral oil, 24.7 mg, 0.6 mmol) was added to a solution of 4-((4-methoxybenzyl)oxy)-2-methyl-6-(1H-pyrazol-4-yl)pyrimidine (118 mg, 0.4 mmol) in DMF (5.0 ml). To the mixture was added 1-(2,6-difluoro-4-(trifluoromethyl)phenyl)ethyl methanesulfonate (125 mg, 0.4 mmol) at RT. The reaction mixture was stirred at RT for 3 h. The resulting mixture was quenched with saturated NH$_4$Cl (20 mL) solution and extracted with DCM (3×20 mL). The combined organic extracts were washed with brine (3×20 mL), dried with anhydrous Na$_2$SO$_4$, and filtered. The filtrate was concentrated under reduced pressure. The residue was purified by silica gel chromatography (0-20% of ethyl acetate in petroleum ether) to furnish the title compound. MS=505.0 (M+1).

PREPARATORY EXAMPLE 47

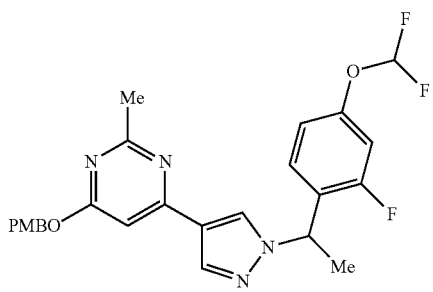

4-(1-(1-(4-(Difluoromethoxy)-2-fluorophenyl)ethyl)-1H-pyrazol-4-yl)-6-((4-methoxybenzyl)oxy)-2-methylpyrimidine, (Scheme 16)

1-(1-Bromoethyl)-4-(difluoromethoxy)-2-fluorobenzene was prepared using procedures similar to those described in step 4 of Preparatory Example 31 using 1-(4-(difluoromethoxy)-2-fluorophenyl)ethanol (80.0 mg, 0.39 mmol) and tribromophosphine (0.231 g, 0.854 mmol) in DCM (4.0 mL) to afford the desired bromide as a liquid and was used in the next step without further purification.

Cesium carbonate (87.0 mg, 0.268 mmol) was added to a solution of 4-((4-methoxybenzyl)oxy)-2-methyl-6-(1H-pyrazol-4-yl)pyrimidine (79.0 mg, 0.268 mmol) in DMF (2.0 ml). To the mixture was added 1-(1-bromoethyl)-4-(difluoromethoxy)-2-fluorobenzene (60.0 mg, 0.223 mmol) at RT. The reaction mixture was stirred at RT for 16 h. The reaction mixture was diluted with DCM (30 mL) and washed with brine (2×30 mL). The separated organic layer was dried with anhydrous Na$_2$SO$_4$, and filtered. The filtrate was concentrated under reduced pressure to afford the title compound as a liquid. MS=485.2 (M+1).

PREPARATORY EXAMPLE 48

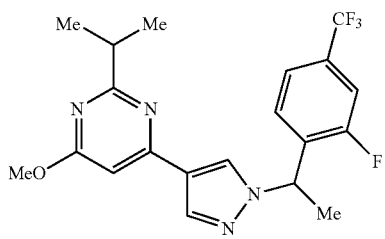 [SMILES: COc1cc(-c2cnn(C(C)c3ccc(C(F)(F)F)cc3F)c2)nc(C(C)C)n1]

4-(1-(1-(2-Fluoro-4-(trifluoromethyl)phenyl)ethyl)-1H-pyrazol-4-yl)-2-isopropyl-6-methoxypyrimidine, (Scheme 17)

To a solution of 2-isopropyl-4-methoxy-6-(1H-pyrazol-4-yl)pyrimidine (100 mg, 0.458 mmol) and 1-(2-fluoro-4-(trifluoromethyl)phenyl)ethanol from (191 mg, 0.916 mmol) in THF (4.0 mL) were added triphenylphosphine (0.361 g, 1.38 mmol) and DIAD (0.27 mL, 1.38 mmol) at 0° C. The reaction mixture was stirred under nitrogen atmosphere at RT for 16 h. The resulting mixture was concentrated under reduced pressure. The residue was diluted with ethyl acetate (100 mL) and washed with brine (2×30 mL). The organic extract was dried with anhydrous Na$_2$SO$_4$ and filtered. The filtrate was concentrated under reduced pressure. The residue was purified by silica gel chromatography (0-5% ethyl acetate in petroleum ether) to furnish the title compound as a solid. MS=409.1 (M+1).

PREPARATORY EXAMPLE 49

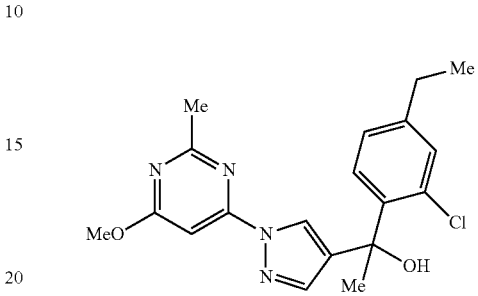

1-(2-Chloro-4-ethylphenyl)-1-(1-(6-methoxy-2-methylpyrimidin-4-yl)-1H-pyrazol-4-yl)ethanol, (Scheme 18)

The title compound was prepared using procedures similar to those described in step 4 of Preparatory Example 14 using 1-(1-(6-methoxy-2-methylpyrimidin-4-yl)-1H-pyrazol-4-yl)ethanone (0.265 g, 1.14 mmol), 1-bromo-2-chloro-4-ethylbenzene (0.50 g, 2.28 mmol) and n-butyllithium (2.5 M in Hexane, 0.9 ml, 2.28 mmol) in THF (6.0 mL) to afford the title compound as a solid. MS=373.2/375.2 (M+1).

PREPARATORY EXAMPLE 50

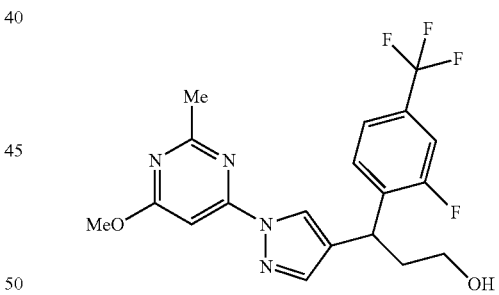

3-(2-fluoro-4-(trifluoromethyl)phenyl)-3-(1-(6-methoxy-2-methylpyrimidin-4-yl)-1H-pyrazol-4-yl)propan-1-ol, (Scheme 29)

Pd-C (53.4 mg, 0.502 mmol) was added to a stirred solution of 4-(4-(3-(benzyloxy)-1-(2-fluoro-4-(trifluoromethyl)phenyl)prop-1-en-1-yl)-1H-pyrazol-1-yl)-6-methoxy-2-methylpyrimidine (50 mg, 0.100 mmol) in MeOH (5 ml) at RT. The reaction mixture was degassed with hydrogen 3 times and stirred under hydrogen for 4 h at RT. The mixture was filtered and the filter cake was washed with MeOH (20 ml). The residue was purified by silica gel chromatography (25% ethyl acetate in petroleum ether) to furnish the title compound as a colorless oil. MS=411.0 (M+1).

EXAMPLES 1 AND 2

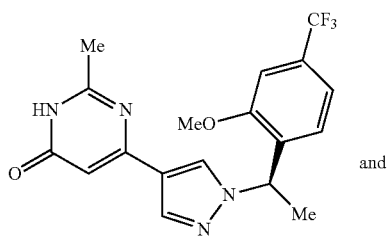

and

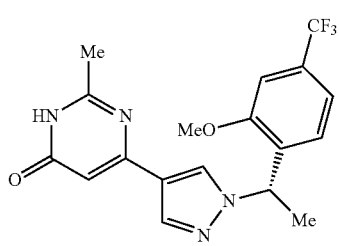

(S)- and (R)-6-(1-(1-(2-Methoxy-4-(trifluoromethyl)phenyl)ethyl)-1H-pyrazol-4-yl)-2-methylpyrimidin-4(3H)-one, (Scheme 19)

4-((4-Methoxybenzyl)oxy)-2-methyl-6-(1H-pyrazol-4-yl)-pyrimidine (100 mg, 0.337 mmol), 1-(1-bromoethyl)-2-methoxy-4-(trifluoromethyl)benzene (115 mg, 0.405 mmol), and cesium carbonate (132 mg, 0.405 mmol) were combined in DMF (1 mL) and stirred for 3 h at RT. The reaction was diluted with ethyl acetate and washed with water (3×). The organic extract was dried over Na$_2$SO$_4$, filtered, and concentrated. The crude alkylation product was then dissolved in DCM (1.0 mL) and treated with TFA (1.0 mL, 12.98 mmol). When the PMB removal was complete, as judged by LC-MS, the volatiles were removed. The residue was dissolved in DCM and washed with saturated NaHCO$_3$ solution. The organic extract was dried over Na$_2$SO$_4$, filtered, and concentrated. The compound was purified by silica gel chromatography (ethyl acetate in hexanes) to furnish the racemic title compound.

The racemic title compound was resolved by chiral HPLC (CHIRALCEL IC column; 40% MeOH in CO$_2$+0.1% Et$_2$NH). Faster-eluting enantiomer of the title compound (Example 1) was obtained as a solid. $^1$H NMR (500 MHz, DMSO-d$_6$) δ: 11.6-11.1 (broad, 1H), 8.39 (s, 1H), 8.01 (s, 1H), 7.30 (s, 1H), 7.27 (d, J=8 Hz, 1H), 7.09 (d, J=8 Hz, 1H), 6.45 (s, 1H), 5.92 (q, J=7 Hz, 1H), 3.92 (s, 3H), 2.28 (s, 3H), 1.77 (d, J=7 Hz, 3H). MS=379.0 (M+1). Slower-eluting enantiomer of the title compound (Example 2) was obtained as a solid. $^1$H NMR (500 MHz, DMSO-d$_6$) δ: 11.6-11.1 (broad, 1H), 8.39 (s, 1H), 8.01 (s, 1H), 7.30 (s, 1H), 7.27 (d, J=8 Hz, 1H), 7.09 (d, J=8 Hz, 1H), 6.45 (s, 1H), 5.92 (q, J=7 Hz, 1H), 3.92 (s, 3H), 2.28 (s, 3H), 1.77 (d, J=7 Hz, 3H). MS=379.0 (M+1).

EXAMPLES 3 AND 4

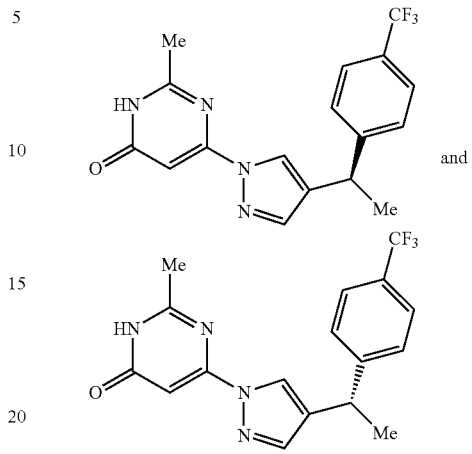

and (S)- and (R)-2-Methyl-6-(4-(1-(4-(trifluoromethyl)phenyl)ethyl)-1H-pyrazol-1-yl)pyrimidin-4(3H)-one, (Scheme 20)

Method A. n-Butyllithium (189 μL, 0.473 mmol) was added to a −40° C. solution of 1-bromo-4-(trifluoromethyl)benzene (66.2 μL, 0.473 mmol) in THF (1.5 ml). The reaction was allowed to stir at this temperature for 1.5 h. Then the cold solution was transferred via cannula to a flask containing a −40° C. solution of 1-(1-(6-((4-methoxybenzyl)oxy)-2-methylpyrimidin-4-yl)-1H-pyrazol-4-yl)ethanone (80 mg, 0.236 mmol) in THF (1 ml). This solution was stirred at −40° C. for 30 min. LCMS indicated complete conversion to the tertiary alcohol 1-(1-(6-((4-methoxybenzyl)oxy)-2-methylpyrimidin-4-yl)-1H-pyrazol-4-yl)-1-(4-(trifluoromethyl)-phenyl)ethanol. The reaction was warmed to RT and quenched with saturated aqueous NH$_4$Cl solution and the product was extracted with ethyl acetate. The extract was dried over Na$_2$SO$_4$, filtered, and concentrated. The crude material was dissolved in DCE (0.7 μL) and treated with triethylsilane (700 μL, 4.38 mmol) and then TFA (700 μL, 9.09 mmol). The reaction was allowed to stir overnight at RT. The reaction mixture was concentrated to provide the crude racemic title compound.

The racemic title compound was resolved by chiral chromatography (Chiralpak ID column; 40% MeOH in CO$_2$+ 0.2% NH$_4$OH). Faster-eluting enantiomer of the title compound (Example 3) was obtained as a solid. $^1$H NMR (500 MHz, DMSO-d$_6$) δ: 12.59 (s, 1H), 8.28 (s, 1H), 7.74 (s, 1H), 7.64 (d, J=8 Hz, 2H), 7.52 (d, J=8 Hz, 2H), 6.38 (s, 1H), 4.24 (q, J=7 Hz, 1), 2.35 (s, 3H), 1.58 (d, J=7 Hz, 3H). MS=349.1 (M+1). Slower-eluting enantiomer of the title compound (Example 4) was obtained as a solid. $^1$H NMR (500 MHz, DMSO-d$_6$) δ: 12.59 (s, 1H), 8.28 (s, 1H), 7.74 (s, 1H), 7.64 (d, J=8 Hz, 2H), 7.52 (d, J=8 Hz, 2H), 6.38 (s, 1H), 4.24 (q, J=7 Hz, 1), 2.35 (s, 3H), 1.58 (d, J=7 Hz, 3H). MS=349.1 (M+1).

Method B. Methylmagnesium bromide (0.025 ml, 0.075 mmol) was added to 0° C. solution of (1-(6-((4-methoxybenzyl)oxy)-2-methylpyrimidin-4-yl)-1H-pyrazol-4-yl)(4-(trifluoromethyl)-phenyl)-methanone (28 mg, 0.060 mmol) in THF (0.5 ml). After 30 minutes an additional equivalent of methylmagnesium bromide (0.025 ml, 0.075 mmol) was added. After an additional 30 minutes, the reaction was quenched with saturated NH₄Cl solution and the product was extracted with ethyl acetate. The extracts were dried over Na₂SO₄, filtered, and concentrated. The resulting tertiary alcohol was purified by silica gel chromatography (5-50% ethyl acetate in hexanes). The product containing fractions were combined and concentrated to yield the tertiary alcohol intermediate. The tertiary alcohol was then dissolved in DCE (0.05 ml) and TFA (0.046 ml, 0.598 mmol) and treated with triethylsilane (0.048 ml, 0.299 mmol). The reaction was stirred at RT until judged to be complete by LCMS. The solvent was removed under vacuum and the product was purified directly by reverse phase chromatography (Biotage 12 g C-18 cartridge; 5-75% acetonitrile in water+0.05% TFA). The product-containing fractions were concentrated and the product was freebased by partitioning between CH₂Cl₂ and saturated NaHCO₃. The organic extract was dried over Na₂SO₄, filtered, and concentrated to provide the title compound. See Method A above for chiral resolution and spectral data.

EXAMPLES 5 AND 6

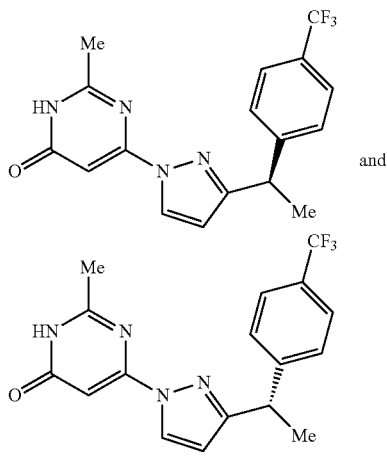

(S)- and (R)-2-Methyl-6-(3-(1-(4-(trifluoromethyl)phenyl)ethyl)-1H-pyrazol-1-yl)pyrimidin-4(3H)-one, (Scheme 21)

3-(1-(4-(Trifluoromethyl)phenyl)ethyl)-1H-pyrazole (100 mg, 0.416 mmol), 4-chloro-6-((4-methoxybenzyl)oxy)-2-methylpyrimidine (95 mg, 0.359 mmol), and cesium carbonate (234 mg, 0.718 mmol) were combined in DMF (1.2 mL) and heated to 100° C. overnight. The reaction was cooled to RT and the DMF was removed by partitioning between ethyl acetate and brine. The organic extract was dried over Na₂SO₄, filtered, and concentrated. The crude material was then dissolved in CH₂Cl₂ (2 mL) and TFA (2 mL, 26.0 mmol) and stirred at RT until the reaction was judged to be complete by LCMS. The solvents were removed and the product was purified by reverse phase chromatography (Biotage 30 g C-18 SNAP cartridge; 10-65% acetonitrile in water+0.05% TFA). The product-containing fractions were concentrated and the solid was partitioned between CH₂Cl₂ and saturated NaHCO₃ solution. The organic extract was dried over Na₂SO₄, filtered, and concentrated to provide the racemic title compound.

The racemic title compound was then resolved into the enantiomers by chiral chromatography (Chiralpak AD column; MeOH in CO₂) to furnish the enantiopure title compounds. Faster-eluting enantiomer of the title compound (Example 5) was obtained as a solid. $^1$H NMR (500 MHz, DMSO-d₆) δ: 12.57 (s, 1H), 8.38 (d, J=2.5 Hz, 1H), 7.68 (d, J=8 Hz, 2H), 7.55 (d, J=8 Hz, 2H), 6.45 (d, J=2.5 Hz, 1H), 6.39 (s, 1H), 4.36 (q, J=7 Hz, 1H), 2.36 (s, 3H), 1.63 (d, J=7 Hz, 3H). MS=349.1 (M+1). Slower-eluting enantiomer of the title compound (Example 6) was obtained as a solid. $^1$H NMR (500 MHz, DMSO-d₆) δ: 12.57 (s, 1H), 8.38 (d, J=2.5 Hz, 1H), 7.68 (d, J=8 Hz, 2H), 7.55 (d, J=8 Hz, 2H), 6.45 (d, J=2.5 Hz, 1H), 6.39 (s, 1H), 4.36 (q, J=7 Hz, 1H), 2.36 (s, 3H), 1.63 (d, J=7 Hz, 3H). MS=349.1 (M+1).

EXAMPLES 7 AND 8

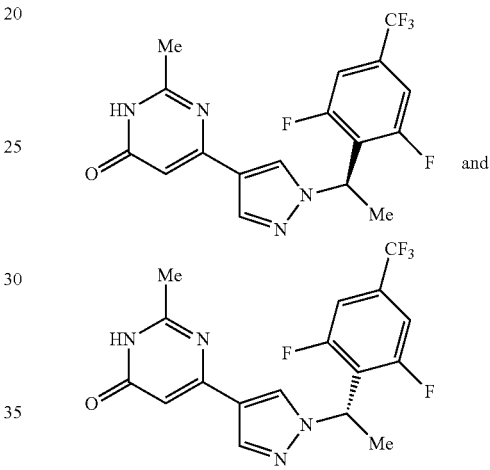

(R)- and (S)-6-(1-(1-(2,6-Difluoro-4-(trifluoromethyl)phenyl)ethyl)-1H-pyrazol-4-yl)-2-methylpyrimidin-4(3H)-one, (Scheme 22)

Step 1. 6-(1-(1-(2,6-Difluoro-4-(trifluoromethyl)phenyl)ethyl)-1H-pyrazol-4-yl)-2-methylpyrimidin-4(3H)-one Trifluoroacetic acid (0.170 g, 1.5 mmol) was added to a stirred solution of 4-(1-(1-(2,6-difluoro-4-(trifluoromethyl)phenyl)ethyl)-1H-pyrazol-4-yl)-6-((4-methoxybenzyl)oxy)-2-methylpyrimidine (0.150 g, 0.3 mmol) in DCM (5.0 mL). The reaction mixture was stirred at RT for 3 h. The reaction mixture was quenched with saturated aqueous NaHCO₃ solution (30 mL) and extracted with DCM (3×30 mL). The combined organic extracts were washed with brine (3×20 mL), dried with anhydrous Na₂SO₄, and filtered. The filtrate was concentrated under reduced pressure. The residue was purified by silica gel chromatography (0-5% MeOH in DCM) to furnish the racemic title compound as a solid. MS=385.0 (M+1).

Step 2. (R)- and (S)-6-(1-(1-(2,6-difluoro-4-(trifluoromethyl)phenyl)ethyl)-1H-pyrazol-4-yl)-2-methylpyrimidin-4(3H)-one The racemic title compound was separated into the enantiomers by chiral HPLC with the following conditions (Chiralcel OJ-H; 50% EtOH in hexanes). Faster-eluting enantiomer of the title compound (Example 7) was obtained as a solid. $^1$H NMR (400 MHz, MeOH-d$_4$) δ: 8.57 (s, 1H), 8.07 (s, 1H), 7.44-7.41 (m, 2H), 6.64 (s, 1H), 6.06 (q, J=7.1 Hz, 1H), 2.54 (s, 3H), 2.08 (d, J=7.2 Hz, 3H). MS=385.1 (M+1). Slower-eluting enantiomer of the title compound (Example 8) was obtained as a solid. $^1$H NMR (400 MHz, MeOH-d$_4$) δ: 8.54 (s, 1H), 8.05 (s, 1H), 7.45-7.42 (m, 2H), 6.60 (s, 1H), 6.07 (q, J=7.2 Hz, 1H), 2.50 (s, 3H), 2.08 (d, J=7.2 Hz, 3H). MS=385.1 (M+1).

EXAMPLE 9

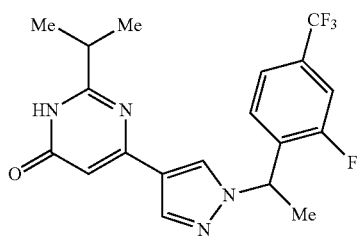 [SMILES: CC(C)c1nc(-c2cnn(C(C)c3ccc(C(F)(F)F)cc3F)c2)cc(=O)[nH]1]

6-(1-(1-(2-Fluoro-4-(trifluoromethyl)phenyl)ethyl)-1H-pyrazol-4-yl)-2-isopropylpyrimidin-4(3H)-one, (Scheme 23)

A solution of 4-(1-(1-(2-fluoro-4-(trifluoromethyl)phenyl)ethyl)-1H-pyrazol-4-yl)-2-isopropyl-6-methoxypyrimidine (210 mg, 0.257 mmol) in MeCN (5 mL) was added sodium iodide (154 mg, 1.028 mmol) and chlorotrimethylsilane (112 mg, 1.028 mmol) at RT. The mixture was stirred for 1.5 h at 70° C. The cooled reaction solution was concentrated under reduced pressure. The residue was dissolved in 50 mL of ethyl acetate washed with brine (2×10 mL). The organic layer was dried over anhydrous sodium sulfate and filtered. The residue was then purified by preparative HPLC (Column: X Bridge C18; 30-70 acetonitrile in water+0.05% TFA) to furnish the title compound as a solid. $^1$H NMR (400 MHz, DMSO-d$_6$) δ: 12.2-12.0 (br, 1H), 8.50 (s, 1H), 8.07 (s, 1H), 7.72 (d, J=10.0 Hz, 1H), 7.60 (d, J=7.6 Hz, 1H), 7.43-7.39 (m, 1H), 6.47 (s, 1H), 6.01 (q, J=7.2 Hz, 1H), 2.86-2.79 (m, 1H), 1.86 (d, J=7.2 Hz, 3H), 1.24 (d, J=8.5 Hz, 3H), 1.22 (d, J=8.5 Hz, 3H). MS=395.2 (M+1).

EXAMPLE 10

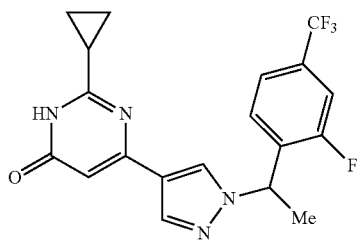 [SMILES: CC(c1ccc(C(F)(F)F)cc1F)n1cc(-c2cc(=O)[nH]c(C3CC3)n2)cn1]

2-Cyclopropyl-6-(1-(2-fluoro-4-(trifluoromethyl)phenyl)ethyl)-1H-pyrazol-4-yl)pyrimidin-4(3H)-one, (Scheme 24)

In a 250 mL round bottom flask, NaCN (338 mg, 6.89 mmol) was added to a stirred solution of 2-cyclopropyl-4-(1-(1-(2-fluoro-4-(trifluoromethyl)phenyl)ethyl)-1H-pyrazol-4-yl)-6-methoxypyrimidine (700 mg, 1.723 mmol) in DMSO (50 ml) at RT. The reaction solution was stirred at 130° C. for 4 h. The reaction solution was cooled, diluted with water (50 mL) and extracted with ethyl acetate (3×70 mL). The combined organic extracts were washed with brine (2×100 mL), dried over anhydrous sodium sulfate, and filtered. The filtrate was concentrated under vacuum. The crude product was purified by preparative HPLC (Surefire Shield C18 column; 38-44% acetonitrile in water+0.05% TFA) to furnish the title compound as a solid. $^1$H NMR (300 MHz, DMSO-d$_6$) δ: 12.33 (s, 1H), 8.45 (s, 1H), 8.01 (s, 1H), 7.71 (d, J=12.5 Hz, 1H), 7.59 (d, J=12.5 Hz, 1H), 7.39 (t, J=12.5 Hz, 1H), 6.38 (s, 1H), 5.98 (q, J=11 Hz, 1H), 1.91-1.83 (m, 1H), 1.84 (d, J=11 Hz, 3H), 1.10-1.00 (m, 4H). MS=393.1 (M+1).

EXAMPLES 11 AND 12

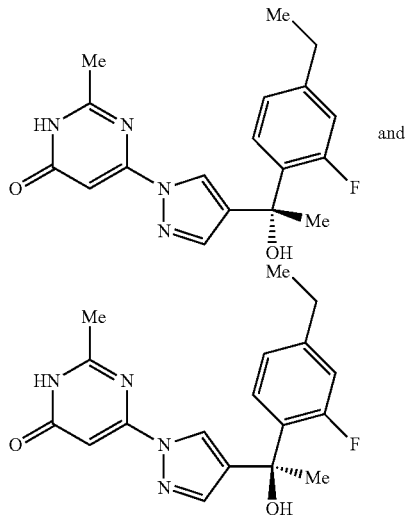

(S)- and (R)-6-(4-(1-(4-Ethyl-2-fluorophenyl)-1-hydroxyethyl)-1H-pyrazol-1-yl)-2-methylpyrimidin-4(3H)-one, (Scheme 25)

Step 1: 6-(4-(1-(4-Ethyl-2-fluorophenyl)-1-hydroxyethyl)-1H-pyrazol-1-yl)-2-methylpyrimidin-4(3H)-one To a solution of 1-(2-fluoro-4-vinylphenyl)-1-(1-(6-((4-methoxybenzyl)oxy)-2-methylpyrimidin-4-yl)-1H-pyrazol-4-yl)ethanol (0.120 g, 0.261 mml) in ethyl acetate (5.0 ml) was added Lindlar catalyst (53.8 mg, 0.026 mmol) at RT. The reaction mixture was purged with hydrogen 3 times and stirred under an atmosphere of hydrogen at RT for 16 h. The resulting mixture was filtered. The filter cake was washed with ethyl acetate (10.0 mL) and the filtrate was concentrated under reduced pressure to afford the crude racemic title compound as a liquid. MS=343.2 (M+1).

Step 2. (S)- and (R)-6-(4-(1-(4-ethyl-2-fluorophenyl)-1-hydroxyethyl)-1H-pyrazol-1-yl)-2-methylpyrimidin-4(3H)-one The racemic title compound (30.0 mg, 0.088 mmol) was separated by chiral HPLC (Lux Cellulose-4; 0-95% EtOH in hexanes+0.1% NH$_4$HCO$_3$) to furnish the enantiopure title compounds. The faster-eluting enantiomer of the title compound (Example 11) was obtained as a solid: $^1$H NMR (400 MHz, MeOD-d$_4$) δ: 8.30 (s, 1H), 7.69-7.63 (m, 2H), 7.08-7.05 (m, 1H), 6.92-6.89 (m, 1H), 6.66 (s, 1H), 2.67 (q, J=7.6 Hz, 2H), 2.45 (s, 3H), 1.95 (s, 3H), 1.26 (t, J=7.6 Hz, 3H). MS=342.9 (M+1). The slower-eluting enantiomer of the title compound (Example 12) was obtained as a solid. $^1$H NMR (400 MHz, MeOD-d$_4$) δ: 8.30 (s, 1H), 7.69-7.63 (m, 2H), 7.07-7.05 (m, 1H), 6.92-6.89 (m, 1H), 6.66 (s, 1H), 2.67 (q, J=7.6 Hz, 2H), 2.45 (s, 3H), 1.95 (s, 3H), 1.26 (t, J=7.8 Hz, 3H). MS=342.9 (M+1).

EXAMPLES 13 AND 14

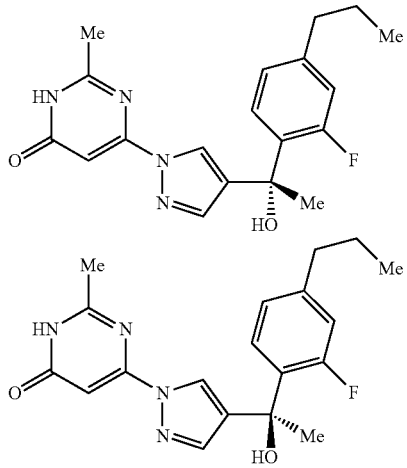

(S)- and (R)-6-(4-(1-(2-Fluoro-4-propylphenyl)-1-hydroxyethyl)-1H-pyrazol-1-yl)-2-methylpyrimidin-4(3H)-one, (Scheme 26)

2,3-Dichloro-5,6-dicyano-1,4-benzoquinone (50.0 mg, 0.220 mmol) was added to a solution of 1-(2-fluoro-4-propylphenyl)-1-(1-(6-((4-methoxybenzyl)oxy)-2-methylpyrimidin-4-yl)-1H-pyrazol-4-yl)ethanol (70.0 mg, 0.147 mmol) in dichloromethane (2.0 mL). The reaction mixture was stirred at 25° C. for 16 h. The resulting mixture was diluted with water (20 mL), extracted with dichloromethane (3×30 mL), washed with brine (2×10.0 mL), dried with anhydrous Na$_2$SO$_4$, and filtered. The filtrate was concentrated under reduced pressure. The residue was purified by preparative HPLC (Gemini C-18 column; 56-71% acetonitrile in water+0.05% TFA) to furnish the racemic title compound.

The racemic title compound was separated by chiral HPLC (Lux Cellulose-4; 0-95% EtOH in hexanes) to furnish the pure enantiomers of the title compound. The faster-eluting enantiomer of the title compound (Example 13): $^1$H NMR (400 MHz, MeOD-d$_4$) δ: 8.31 (s, 1H), 7.69-7.62 (m, 2H), 7.06-7.03 (m, 1H), 6.90-6.87 (m, 1H), 6.66 (s, 1H), 2.62 (t, J=7.6 Hz, 2H), 2.45 (s, 3H), 1.95 (s, 3H), 1.72-1.63 (m, 2H), 0.97 (t, J=7.2 Hz, 3H). MS=357.0 (M+1). The slower-eluting enantiomer of the title compound (Example 14): $^1$H NMR (400 MHz, MeOD-d$_4$) δ: 8.31 (s, 1H), 7.69-7.62 (m, 2H), 7.06-7.03 (m, 1H), 6.90-6.87 (m, 1H), 6.66 (s, 1H), 2.62 (t, J=7.6 Hz, 2H), 2.45 (s, 3H), 1.95 (s, 3H), 1.72-1.63 (m, 2H), 0.97 (t, J=7.2 Hz, 3H). MS=357.0 (M+1).

EXAMPLES 15 AND 16

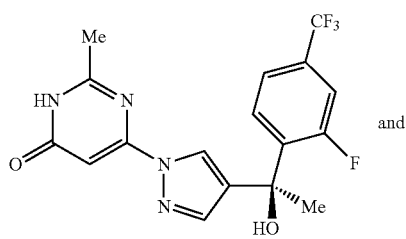
and
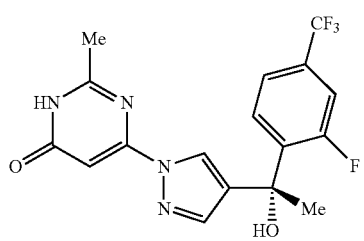

(S)- and (R)-6-(4-(1-(2-Fluoro-4-(trifluoromethyl)phenyl)-1-hydroxyethyl)-1H-pyrazol-1-yl)-2-methylpyrimidin-4(3H)-one, (Scheme 27)

1-(2-Fluoro-4-(trifluoromethyl)phenyl)-1-(1-(6-((4-methoxy-benzyl)oxy)-2-methylpyrimidin-4-yl)-1H-pyrazol-4-yl)ethanol (297 mg, 0.591 mmol), allyltrimethylsilane (0.282 ml, 1.773 mmol), and iron(III) chloride hexahydrate (32.0 mg, 0.118 mmol) were combined in CH$_2$Cl$_2$ (2.5 mL) and stirred at RT overnight and then at 60° C. for 3 h. The reaction was diluted with CH$_2$Cl$_2$ and washed with saturated NaHCO$_3$ solution. The organic layer was dried over Na$_2$SO$_4$, filtered, and concentrated. The residue was purified by reverse phase chromatography (Biotage 30 g C-18 SNAP cartridge; 0-70% acetonitrile in water+0.05% TFA) to provide the title compound.

The racemic title compound was separated by chiral HPLC (Chiralpak OD-H (15% MeOH in CO$_2$+0.1% Et$_2$NH) to furnish the title compounds. The faster-eluting enantiomer of the title compound (Example 15): $^1$H NMR (500 MHz, DMSO-d$_6$) δ: 12.78-12.40 (broad, 1H), 8.24 (s, 1H), 8.00 (t, J=8 Hz, 1H), 7.75 (s, 1H), 7.65 (d, J=8 Hz, 1H), 7.58 (d, J=11.5 Hz, 1H), 6.40 (s, 1H), 6.16 (s, 1H), 2.35 (s, 3H), 1.88 (s, 3H). MS=383.1 (M+1). The slower-eluting enantiomer of the title compound (Example 16): $^1$H NMR (500 MHz, DMSO-d$_6$) δ: 12.78-12.38 (broad, 1H), 8.24 (s, 1H), 8.00 (t, J=8 Hz, 1H), 7.75 (s, 1H), 7.65 (d, J=8 Hz, 1H), 7.58 (d, J=11.5 Hz, 1H), 6.40 (s, 1H), 6.17 (s, 1H), 2.35 (s, 3H), 1.88 (s, 3H). MS=383.1 (M+1).

EXAMPLES 17 AND 18

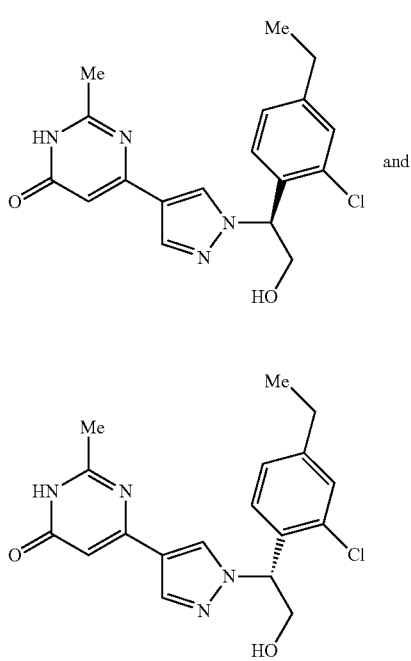

(S)- and (R)-6-(1-(1-(2-Chloro-4-ethylphenyl)-2-hydroxyethyl)-1H-pyrazol-4-yl)-2-methylpyrimidin-4(3H)-one, (Scheme 28)

NaBH$_4$ (70.0 mg, 1.86 mmol) was added to a solution of methyl 2-(2-chloro-4-ethylphenyl)-2-(4-(2-methyl-6-oxo-1,6-dihydropyrimidin-4-yl)-1H-pyrazol-1-yl)acetate (120 mg, 0.310 mmol) in methanol (2.0 mL). The reaction solution was stirred at RT for 12 h. The resulting mixture was diluted with water (30 mL), extracted with ethyl acetate (3×30 mL), washed with brine (2×10 mL), dried with anhydrous Na$_2$SO$_4$, and filtered. The filtrate was concentrated under reduced pressure. The residue was purified by silica gel chromatography (0-40% of ethyl acetate in hexane) to furnish the racemic title compound.

The racemic title compound was separated by chiral HPLC (Chiralpak IA; 0-20% EtOH in hexane) to furnish the enantiomers of the title compound. The faster-eluting enantiomer of the title compound (Example 17) was obtained as a solid. $^1$H NMR (300 MHz, CDCl$_3$) δ: 8.10 (s, 1H), 7.91 (s, 1H), 7.03-6.95 (m, 2H), 6.39 (s, 1H), 5.95-5.93 (m, 1H), 4.50-4.43 (m, 1H), 4.18-4.15 (m, 1H), 2.58 (q, J=7.5 Hz, 2H), 2.50 (s, 3H), 1.31-1.27 (m, 2H), 1.20 (t, J=7.5 Hz, 3H). MS=359.2; 361.2 (M+1). The slower-eluting enantiomer of the title compound (Example 18) was obtained as a solid. $^1$H NMR (300 MHz, CDCl$_3$) δ: 8.10 (s, 1H), 7.91 (s, 1H), 7.03-6.95 (m, 2H), 6.39 (s, 1H), 5.95-5.93 (m, 1H), 4.50-4.43 (m, 1H), 4.18-4.15 (m, 1H), 2.58 (q, J=7.5 Hz, 2H), 2.50 (s, 3H), 1.31-1.27 (m, 2H), 1.20 (t, J=7.5 Hz, 3H). MS=359.2; 361.2 (M+1).

EXAMPLES 19 AND 20

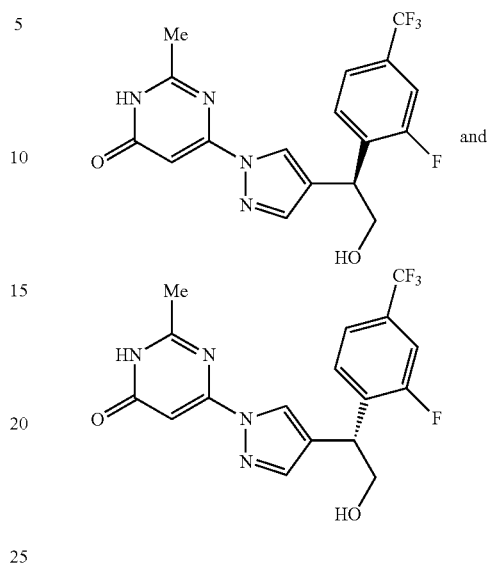

(S)- and (R)-6-(4-(1-(2-Fluoro-4-(trifluoromethyl)phenyl)-2-hydroxyethyl)-1H-pyrazol-1-yl)-2-methylpyrimidin-4(3H)-one, (Scheme 30)

Step 1. 6-(4-(1-(2-Fluoro-4-(trifluoromethyl)phenyl)vinyl)-1H-pyrazol-1-yl)-2-methylpyrimidin-4(3H)-one n-Butyllithium (0.461 ml, 1.153 mmol) was added to a −78° C. solution of 1-bromo-2-fluoro-4-(trifluoromethyl)benzene (287 mg, 1.182 mmol) in THF (3 mL). The reaction was stirred at −78° C. for 1 h. The temperature was warmed to −40° C. before the dropwise addition of 1-(1-(6-((4-methoxybenzyl)oxy)-2-methylpyrimidin-4-yl)-1H-pyrazol-4-yl)ethanone (200 mg, 0.591 mmol) as a solution in THF (1 mL). Upon completion of the reaction, as judged by LCMS, saturated aqueous NH$_4$Cl solution was added. The addition product was extracted with ethyl acetate and the extract was dried over Na$_2$SO$_4$, filtered, and concentrated. The residue was then dissolved in DCE (2 mL) and treated with TFA (0.911 ml, 11.82 mmol). The volatiles were removed and the product was partitioned between CH$_2$Cl$_2$ and saturated NaHCO$_3$ solution. The organic extract was dried over Na$_2$SO$_4$, filtered, and concentrated to yield the title compound which was used in the next step without further purification. LC-MS?

Step 2. (S)- and (R)-6-(4-(1-(2-fluoro-4-(trifluoromethyl)phenyl)-2-hydroxyethyl)-1H-pyrazol-1-yl)-2-methylpyrimidin-4(3H)-one 6-(4-(1-(2-Fluoro-4-(trifluoromethyl)phenyl)vinyl)-1H-pyrazol-1-yl)-2-methylpyrimidin-4(3H)-one (114 mg, 0.313 mmol) was treated with 9-BBN (2.503 mL, 1.252 mmol) and heated to 50° C. for 15 h. The reaction was cooled to RT and treated with water (1 mL, 55.5 mmol) and sodium perborate tetrahydrate (385 mg, 2.503 mmol) and stirred for 2 h at RT. The reaction was diluted with DCM and washed with saturated aqueous NaHCO$_3$ solution. The organic layer was dried over Na$_2$SO$_4$, filtered, and concentrated. The residue was purified by reverse phase chromatography (10-70% acetonitrile in water+0.05% TFA) to provide the racemic title compound.

The racemic title compound was then separated by chiral SFC chromatography (AD-H column; 30% MeOH in $CO_2$+ 0.2% diethylamine) to provide the enantiomers of the title compound. The faster-eluting enantiomer of the title compound (Example 19): $^1$H NMR (500 MHz, DMSO-$d_6$) δ: 12.6-12.1 (broad, 1H), 8.36 (s, 1H), 7.78 (s, 1H), 7.66-7.60 (m, 2H), 7.56 (d, J=8.5 Hz, 1H), 6.40 (s, 1H), 5.09-5.07 (m, 1H), 4.46-4.43 (m, 1H), 3.94-3.92 (m, 2H), 2.36 (s, 3H). MS=383.0 (M+1). The slower-eluting enantiomer of the title compound (Example 20): $^1$H NMR (500 MHz, CDCl$_3$) δ: 12.6-12.1 (broad, 1H), 8.36 (s, 1H), 7.78 (s, 1H), 7.66-7.60 (m, 2H), 7.56 (d, J=8.5 Hz, 1H), 6.40 (s, 1H), 5.09-5.07 (m, 1H), 4.46-4.43 (m, 1H), 3.94-3.92 (m, 2H), 2.36 (s, 3H). MS=383.0 (M+1).

EXAMPLES 21 AND 22

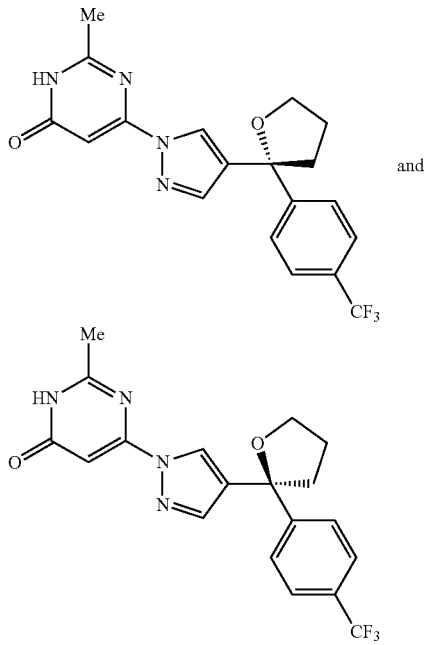

(S)- and (R)-2-Methyl-6-(4-(2-(4-(trifluoromethyl)phenyl)tetrahydrofuran-2-yl)-1H-pyrazol-1-yl)pyrimidin-4(3H)-one, (Scheme 31)

Step 1. 1-(1-(6-((4-Methoxybenzyl)oxy)-2-methylpyrimidin-4-yl)-1H-pyrazol-4-yl)-1-(4-(trifluoromethyl)phenyl)but-3-en-1-ol Allylmagnesium bromide (0.640 ml, 0.640 mmol) was added to a 0° C. solution of (1-(6-((4-methoxybenzyl)oxy)-2-methylpyrimidin-4-yl)-1H-pyrazol-4-yl)(4-(trifluoromethyl)phenyl)methanone (200 mg, 0.427 mmol) in THF (2 mL). The reaction was allowed to warm to RT. After 3 h the reaction was quenched with saturated aqueous $NH_4Cl$ solution. The product was extracted with ethyl acetate. The extracts were dried over $Na_2SO_4$, filtered, and concentrated. The residue was purified by silica gel chromatography (0-20% ethyl acetate in hexanes) to provide the title compound. MS=511.2 (M+1).

Step 2. (S)- and (R)-2-methyl-6-(4-(2-(4-(trifluoromethyl)phenyl)tetrahydrofuran-2-yl)-1H-pyrazol-1-yl)pyrimidin-4(3H)-one 9-BBN (1.410 ml, 0.705 mmol) was added to stirring solution of 1-(1-(6-((4-methoxybenzyl)oxy)-2-methylpyrimidin-4-yl)-1H-pyrazol-4-yl)-1-(4-(trifluoromethyl)-phenyl)but-3-en-1-ol (100 mg, 0.196 mmol) in THF (0.5 ml) at RT in three equal portions. The reaction was heated to 50° C. overnight. Water (2 mL) and sodium perborate tetrahydrate (332 mg, 2.155 mmol) were added and the solution was stirred vigorously for 1 h. The reaction was diluted with ethyl acetate and washed with water (3×10 mL). The organic extract was dried over $Na_2SO_4$, filtered, and concentrated. Crude 1-(1-(6-((4-methoxybenzyl)oxy)-2-methylpyrimidin-4-yl)-1H-pyrazol-4-yl)-1-(4-(trifluoromethyl)phenyl)-butane-1,4-diol was then dissolved in $CH_2Cl_2$ (2 mL) and treated with TFA (2 mL). After 1 h, the solvent was removed and the crude material was taken up in DCM and washed with $NaHCO_3$. The organic extract was dried over $Na_2SO_4$, filtered, and concentrated. The residue was purified by silica gel chromatography (0-50% (3:1 ethyl acetate:EtOH) in hexanes) to provide the racemic title compound.

The enantiomers were then separated by chiral SFC chromatography (AD column; 60% MeOH in $CO_2$+0.2% $NH_4OH$) to provide the enantiomers of the title compound. The faster-eluting enantiomer of the title compound (Example 21): $^1$H NMR (500 MHz, CDCl$_3$) δ: 13.4-12.8 (broad, 1H), 8.30 (s, 1H), 7.70 (s, 1H), 7.63 (d, J=9 Hz, 2H), 7.60 (d, J=9 Hz, 2H), 6.85 (s, 1H), 4.12-4.09 (m, 2H), 2.64-2.58 (m, 1H), 2.56 (s, 3H), 2.46-2.41 (m, 1H), 2.14-2.07 (m, 1H), 2.05-1.98 (m, 1H). MS=391.2 (M+1). The slower-eluting enantiomer of the title compound (Example 22): $^1$H NMR (500 MHz, CDCl$_3$) δ: 13.4-12.8 (broad, 1H), 8.30 (s, 1H), 7.70 (s, 1H), 7.63 (d, J=9 Hz, 2H), 7.60 (d, J=9 Hz, 2H), 6.85 (s, 1H), 4.12-4.09 (m, 2H), 2.64-2.58 (m, 1H), 2.56 (s, 3H), 2.46-2.41 (m, 1H), 2.14-2.07 (m, 1H), 2.05-1.98 (m, 1H). MS=391.2 (M+1).

EXAMPLES 23 AND 24

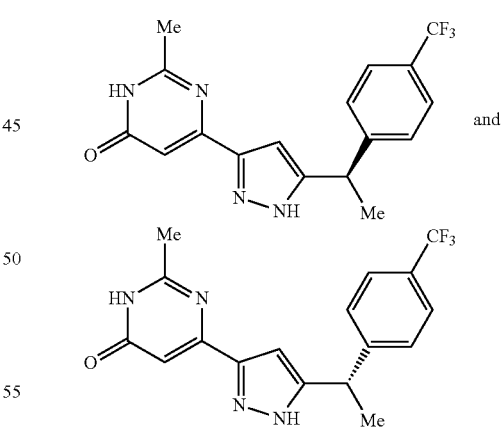

(S)- and (R)-2-Methyl-6-(3-(1-(4-(trifluoromethyl)phenyl)ethyl)-1H-pyrazol-5-yl)pyrimidin-4(3H)-one, (Scheme 32)

Step 1. t-Butyldimethyl((4-(4-(trifluoromethyl)phenyl)pent-1-yn-3-yl)oxy)silane

TBS-Cl (1.290 g, 8.56 mmol) was added as a solution in DMF (2 mL) to a 0° C. solution of 4-(4-(trifluoromethyl)- phenyl)pent-1-yn-3-ol (1.86 g, 8.15 mmol) and imidazole (1.110 g, 16.30 mmol) in DMF (8 mL). The mixture was warmed to room temperature and stirred for 36 h. The reaction was partioned between water and ether and the organic extract was dried over $Na_2SO_4$, filtered, and concentrated. The residue was then purified by silica gel chromatography (0-5% ethyl acetate in hexanes) to provide the title compound as a mixture of diastereomers. $^1H$ NMR (500 MHz, $CDCl_3$) δ: 7.59 (d, J=8.5 Hz, 2H), 7.43 (d, J=8.5 Hz, 2H), 4.47 (dd, J=5 Hz, J=3.5 Hz, 0.66H, major diastereomer), 4.41 (dd, J=2 Hz, J=7 Hz, 0.33H, minor diastereomer), 3.14-3.05 (m, 1H), 2.46 (d, J=2.5 Hz, 0.33H, minor diastereomer), 2.41 (d, J=2 Hz, 0.66H, major diastereomer), 1.46-1.44 (m, 3H), 0.91 (s, 6H, major diastereomer), 0.83 (s, 3H, minor diastereomer), 0.09 and 0.01 (s, 4H, major diastereomer), 0.08 and –0.03 (s, 2H, minor diastereomer).

Step 2. 1-(6-((4-Methoxybenzyl)oxy)-2-methylpyrimidin-4-yl)-4-(4-(trifluoromethyl)-phenyl)pent-1-yn-3-one 4-Chloro-6-((4-methoxybenzyl)oxy)-2-methylpyrimidine (529 mg, 2 mmol), t-butyl-dimethyl((4-(4-(trifluoromethyl)phenyl)pent-1-yn-3-yl)oxy)silane (790 mg, 2.307 mmol), [(Di(1-adamantyl)-butylphosphine)-2-(2'-amino-1,1'-biphenyl)]palladium(II) methanesulfonate (134 mg, 0.200 mmol), and cesium carbonate (1955 mg, 6.00 mmol) were combined in degassed toluene (7 ml). The mixture was degassed briefly (~2 min) after all the reactants were combined to ensure that the mixture was air-free. The reaction was then heated to 90° C. overnight. The mixture was cooled to RT and filtered through silica gel eluting with ethyl acetate. The eluent was concentrated to yield the crude intermediate 4-(3-((tert-butyldimethylsilyl)oxy)-4-(4-(trifluoromethyl)-phenyl)pent-1-yn-1-yl)-6-((4-methoxy-benzyl)oxy)-2-methylpyrimidine. This material was dissolved in THF (20 mL), treated with tetrabutylammonium fluoride (2.400 ml, 2.400 mmol), and stirred for 3 h at RT. The mixture was diluted with ethyl acetate and washed with saturated $NaHCO_3$ solution. The organic extract was dried over $Na_2SO_4$, filtered, and concentrated. Crude 1-(6-((4-methoxybenzyl)oxy)-2-methylpyrimidin-4-yl)-4-(4-(trifluoromethyl)phenyl)pent-1-yn-3-ol was then dissolved in DCM (7.00 ml) cooled to 0° C. and sodium bicarbonate (1680 mg, 20.00 mmol) and Dess-Martin Periodinane (1018 mg, 2.400 mmol) were added sequentially. After 1 h, the reaction mixture was filtered through silica gel eluting with ethyl acetate. The eluent was concentrated and the residue was purified by silica gel chromatography (0-20% ethyl acetate in hexanes) to yield the title compound. MS=455.0 (M+1).

Step 3. (S)- and (R)-2-Methyl-6-(3-(1-(4-(trifluoromethyl)phenyl)ethyl)-1H-pyrazol-5-yl)pyrimidin-4(3H)-one 1-(6-((4-Methoxybenzyl)oxy)-2-methylpyrimidin-4-yl)-4-(4-(trifluoromethyl)phenyl)pent-1-yn-3-one (52 mg, 0.114 mmol) and hydrazine (0.012 ml, 0.137 mmol) were combined in DMA (0.70 mL) and stirred at RT until the reaction was judged to be complete by LCMS. The reaction mixture was diluted with ethyl acetate and the DMA was washed away with brine (3×). The organic extracts were dried over $Na_2SO_4$, filtered, and concentrated. The crude material was then dissolved in $CH_2Cl_2$ (1 mL) and treated with TFA (1 mL, 12.98 mmol) and the reaction was stirred at RT until the deprotection was complete as judged by LCMS. The solvent was removed and the mixture was directly purified by reverse phase chromatography (10-55% acetonitrile in water+0.05% TFA) to furnish the racemic title compound.

The racemic title compound was then separated by chiral chromatography (Chiralpak AD column; 70% MeOH in $CO_2$+0.2% $NH_4OH$) to furnish the enantiopure title compounds. The faster-eluting enantiomer of the title compound (Example 23): $^1H$ NMR (500 MHz, DMSO-$d_6$) δ: 13.22-13.02 (broad, 1H), 12.42-12.28 (broad, 1H), 7.67 (d, J=8 Hz, 2H), 7.50 (d, J=8 Hz, 2H), 6.64 (broad, 1H), 6.56 (s, 1H), 4.32 (m, 1H), 2.31 (s, 3H), 1.60 (d, J=7 Hz, 3H). MS=349.1 (M+1). The slower-eluting enantiomer of the title compound (Example 24): $^1H$ NMR (500 MHz, DMSO-$d_6$) δ: 13.22-13.02 (broad, 1H), 12.42-12.28 (broad, 1H), 7.67 (d, J=8 Hz, 2H), 7.50 (d, J=8 Hz, 2H), 6.64 (broad, 1H), 6.56 (s, 1H), 4.32 (m, 1H), 2.31 (s, 3H), 1.60 (d, J=7 Hz, 3H). MS=349.1 (M+1).

EXAMPLES 25 AND 26

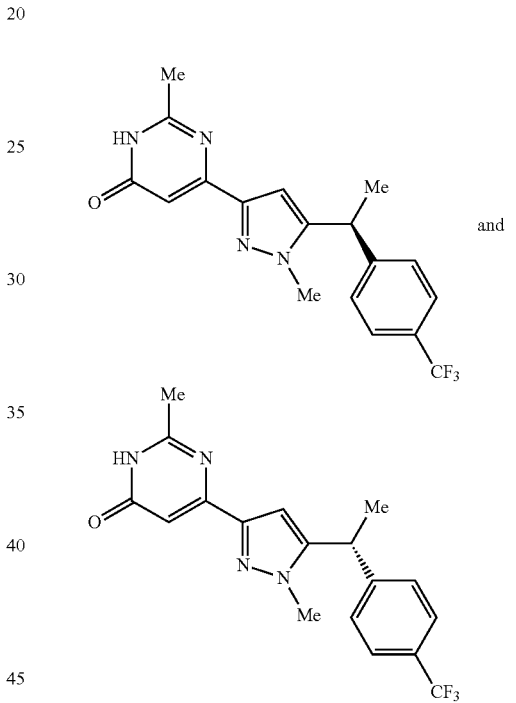

(S)- and (R)-2-Methyl-6-(1-methyl-5-(1-(4-(trifluoromethyl)-phenyl)-1-ethyl)-1H-pyrazol-3-yl)pyrimidin-4(3H)-one, (Scheme 33)

A suspension of sodium hydride (60% in mineral oil, 5.89 mg, 0.147 mmol) in DMSO (0.3 mL) was added dropwise to a 0° C. solution of 4-((4-methoxybenzyl)oxy)-2-methyl-6-(5-(1-(4-(trifluoromethyl)phenyl)ethyl)-1H-pyrazol-3-yl) pyrimidine (50 mg, 0.098 mmol) in DMSO (0.3 mL). Next, methyl iodide (15 µL, 0.240 mmol) was added and the reaction was warmed to RT after 5 minutes. One hour later, an additional portion of sodium hydride (5.89 mg, 0.147 mmol) and methyl iodide (15 µL, 0.240 mmol) were added at RT. After 15 minutes, the reaction was poured into ice water and diluted with EtOAc. The organic extract was washed with brine/water (50/50), dried over $Na_2SO_4$, and concentrated. The crude residue was then dissolved in DCM (1 mL) and treated with TFA (1 mL, 12.98 mmol) at RT. The reaction mixture was concentrated and purified by RP- HPLC (Sunfire Prep C18; 20%-90% acetonitrile in water+ 0.05% TFA) to furnish the racemic title compound.

The racemic title compound was then separated by chiral chromatography (Chiralpak AD column; 70% MeOH in CO$_2$+0.2% NH$_4$OH) to furnish the enantiopure title compounds. The faster-eluting enantiomer of the title compound (Example 25): $^1$H NMR (500 MHz, DMSO-d$_6$) δ: 12.34 (s, 1H), 7.69 (d, J=8.5 Hz, 2H), 7.45 (d, J=8 Hz, 2H), 6.78 (s, 1H), 6.51 (s, 1H), 4.45 (q, J=7.5 Hz, 1H), 3.62 (s, 3H), 2.32 (s, 3H), 1.59 (d, J=7.5 Hz, 3H). MS=363.1 (M+1). The slower-eluting enantiomer of the title compound (Example 26): $^1$H NMR (500 MHz, DMSO-d$_6$) δ: 12.34 (s, 1H), 7.69 (d, J=8.5 Hz, 2H), 7.45 (d, J=8 Hz, 2H), 6.78 (s, 1H), 6.51 (s, 1H), 4.45 (q, J=7.5 Hz, 1H), 3.62 (s, 3H), 2.32 (s, 3H), 1.59 (d, J=7.5 Hz, 3H). MS=363.1 (M+1).

EXAMPLES 27 AND 28

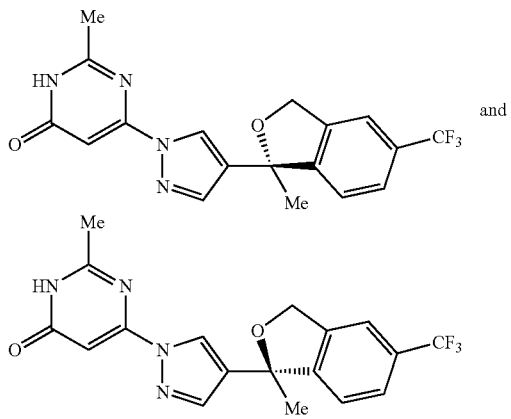

(S)- and (R)-2-Methyl-6-(4-(1-methyl-5-(trifluoromethyl)-1,3-dihydroisobenzofuran-1-yl)-1H-pyrazo-1-1-yl)pyrimidin-4(3H)-one, (Scheme 34)

Di-n-butylmagnesium (0.307 ml, 0.307 mmol) was added to a 0° C. solution of (2-bromo-5-(trifluoromethyl)phenyl)methanol (151 mg, 0.591 mmol) in THF (1 mL). The mixture was warmed to RT for 5 minutes and then recooled to 0° C. and stirred for 15 minutes at this temperature. Then n-butyllithium (0.236 ml, 0.591 mmol) was added slowly over 15 minutes and the resulting mixture was stirred for 1 h at 0° C. At this time, a solution of 1-(1-(6-((4-methoxybenzyl)oxy)-2-methylpyrimidin-4-yl)-1H-pyrazol-4-yl) ethanone (100 mg, 0.296 mmol) in THF (1 mL) was added and the mixture was stirred until the addition was deemed to be complete by LCMS. The reaction was then quenched with saturated aqueous NH$_4$Cl solution and the product was extracted with CH$_2$Cl$_2$ (2×10 mL). The organic extracts were dried over Na$_2$SO$_4$, filtered, and concentrated. The crude material was then dissolved in DCE (2 mL)/TFA (2 mL, 26.0 mmol) and stirred until the intermediate, 1-(2-hydroxymethyl)-4-(trifluoromethyl)phenyl)-1-(1-(6-((4-methoxybenzyl)oxy)-2-methylpyrimidin-4-yl)-1H-pyrazol-4-yl)ethanol, was converted completely to 2-methyl-6-(4-(1-methyl-5-(trifluoromethyl)-1,3-dihydroisobenzofuran-1-yl)-1H-pyrazol-1-yl)pyrimidin-4(3H)-one. The volatiles were removed and the residue was purified by silica gel chromatography (0-30% (3:1 EA:EtOH) in hexanes) to provide the racemic title compound.

The racemic title compound was then separated by chiral SFC chromatography (Chiralpak OZ column; 20% MeOH in CO$_2$+0.2% NH$_4$OH) to furnish the enantiopure title compounds. The faster-eluting enantiomer of the title compound (Example 27): $^1$H NMR (500 MHz, DMSO-d$_6$) δ: 12.70-12.43 (broad s, 1H), 8.33 (s, 1H), 7.87 (s, 1H), 7.74 (s, 1H), 7.69 (d, J=8 Hz, 1H), 7.63 (d, J=8 Hz, 1H), 6.40 (s, 1H), 5.20 (d, J=13.5 Hz, 1H), 5.17 (d, J=13.5 Hz, 1H), 2.36 (s, 3H), 1.83 (s, 3H). MS=377.2 (M+1). The slower-eluting enantiomer of the title compound (Example 28): $^1$H NMR (500 MHz, DMSO-d$_6$) δ: 12.66-12.43 (broad s, 1H), 8.33 (s, 1H), 7.87 (s, 1H), 7.74 (s, 1H), 7.69 (d, J=8 Hz, 1H), 7.63 (d, J=8 Hz, 1H), 6.40 (s, 1H), 5.20 (d, J=13.5 Hz, 1H), 5.17 (d, J=13.5 Hz, 1H), 2.36 (s, 3H), 1.83 (s, 3H). MS=377.2 (M+1).

EXAMPLE 29

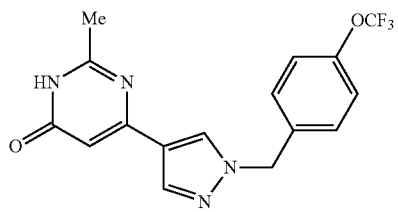 [SMILES: Cc1nc(-c2cnn(Cc3ccc(OC(F)(F)F)cc3)c2)cc(=O)[nH]1]

2-Methyl-6-(1-(4-(trifluoromethoxy)benzyl)-1H-pyrazol-4-yl)pyrimidin-4(3H)-one (Scheme 35)

4-Bromo-1-(4-(trifluoromethoxy)benzyl)-1H-pyrazole (193 mg, 0.601 mmol), 4,4,4',4',5,5,5',5'-octamethyl-2,2'-bi (1,3,2-dioxaborolane) (153 mg, 0.601 mmol), potassium acetate (98 mg, 1 mmol), 2-dicyclohexylphosphino-2',6'-dimethoxybiphenyl (24.67 mg, 0.060 mmol), and Pd$_2$(dba)$_3$ (13.76 mg, 0.015 mmol) were combined in degassed dioxane (2 mL) and heated to 105° C. for 2.5 h. Then potassium phosphate tribasic (0.601 ml, 3.01 mmol) and 4-chloro-6-((4-methoxybenzyl)oxy)-2-methylpyrimidine (132 mg, 0.5 mmol) were added and the reaction was heated at 105° C. for an additional 4 h. The reaction was cooled to RT, filtered through silica gel eluting with ethyl acetate, and concentrated. The crude material was then dissolved in DCM (1 ml) and treated with TFA (1 ml, 12.98 mmol) and stirred at RT until the deprotection was judged to be complete by LCMS. The solvent was removed and the residue was purified by reverse chromatography (Biotage C-18 cartridge; 10-60% ACN in water+0.05 TFA) to afford the title compound. $^1$H NMR (500 MHz, DMSO-d$_6$) δ: 12.20 (s, 1H), 8.43 (s, 1H), 8.04 (s, 1H), 7.40 (d, J=9 Hz, 2H), 7.36 (d, J=9 Hz, 2H), 6.43 (s, 1H), 5.41 (s, 2H), 2.29 (s, 3H). MS=351.0 (M+1).

EXAMPLE 30

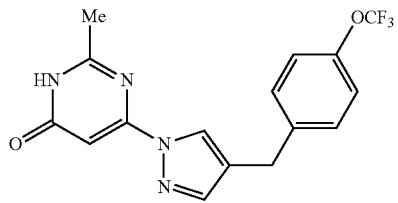 [SMILES: Cc1nc(-n2cc(Cc3ccc(OC(F)(F)F)cc3)cn2)cc(=O)[nH]1]

2-Methyl-6-(4-(4-(trifluoromethoxy)benzyl)-1H-pyrazol-1-yl)pyrimidin-4(3H)-one, (Scheme 36)

Step 1. 4-(4-Bromo-1H-pyrazol-1-yl)-6-((4-methoxybenzyl)oxy)-2-methylpyrimidine 4-bromo-1H-pyrazole (220 mg, 1.500 mmol) was added to a suspension of sodium hydride (60% in mineral oil, 60.0 mg, 1.500 mmol) in DMF (0.25 mL) as a solution in DMF (0.75 mL). The mixture was stirred at RT for 30 minutes before the addition of 4-chloro-6-((4-methoxybenzyl)oxy)-2-methylpyrimidine (265 mg, 1 mmol) as a solution in DMF (1 mL). The reaction was then heated to 100° C. for 4 h. The reaction was cooled to RT, diluted with ethyl acetate, washed with brine (3×), dried over Na$_2$SO$_4$, filtered, and concentrated. The material was then purified by silica gel chromatography (0-25% ethyl acetate in hexanes) to furnish the title compound. MS=376.9 (M+1).

Step 2. 2-Methyl-6-(4-(4-(trifluoromethoxy)benzyl)-1H-pyrazol-1-yl)pyrimidin-4(3H)-one 4-(4-Bromo-1H-pyrazol-1-yl)-6-((4-methoxybenzyl)oxy)-2-methylpyrimidine (50 mg, 0.133 mmol), 4,4,5,5-tetramethyl-2-(4-(trifluoromethoxy)benzyl)-1,3,2-dioxaborolane (121 mg, 0.400 mmol), palladium(II) acetate (2.99 mg, 0.013 mmol), 2-dicyclohexylphosphino-2',6'-dimethoxybiphenyl (6.56 mg, 0.016 mmol), and potassium phosphate tribasic (0.081 ml, 0.400 mmol) were combined in a 5 mL microwave vial and degassed dioxane (0.5 ml) and water (0.1 ml) were added under an atmosphere of nitrogen. The reaction was heated to 85° C. for 3 h. The reaction was cooled to RT, filtered through a silica gel plug eluting with ethyl acetate, and concentrated. The crude mixture was then concentrated, dissolved in DCM (1 ml) and treated with TFA (10.27 µl, 0.133 mmol). After 1 h, the solvent was removed and the product was residue was purified by reverse phase chromatography (Biotage C-18 SNAP cartridge; 10-75% ACN in water+0.05% TFA) to furnish the title compound. $^1$H NMR (500 MHz, DMSO-d$_6$) δ: 12.60 (s, 1H), 8.31 (s, 1H), 7.75 (s, 1H), 7.40 (d, J=8.5 Hz, 2H), 7.29 (d, J=8.5 Hz, 2H), 6.39 (s, 1H), 3.89 (s, 2H), 2.35 (s, 3H). MS=351.0 (M+1).

EXAMPLE 31

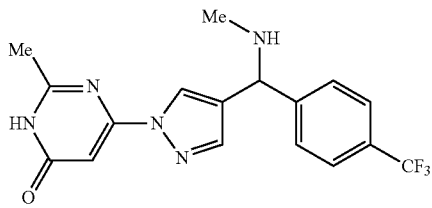 [SMILES: CNC(c1ccc(C(F)(F)F)cc1)c1cnn(-c2cc(=O)[nH]c(C)n2)c1]

2-Methyl-6-(4-((methylamino)(4-(trifluoromethyl)phenyl)methyl)-1H-pyrazol-1-yl)pyrimidin-4(3H)-one, (Scheme 37)

Titanium(iv) isopropoxide (0.043 mL, 0.144 mmol) was added to a vial containing methanamine (2M in THF) (0.167 mL, 0.333 mmol) followed by the addition of (1-(6-((4-methoxybenzyl)oxy)-2-methylpyrimidin-4-yl)-1H-pyrazol-4-yl)(4-(trifluoromethyl)-phenyl)methanone (52 mg, 0.111 mmol) and the mixture was allowed to stir at RT for 4 h. The reaction was heated to 55° C. for 2 h. After cooling to RT sodium borohydride (4.62 mg, 0.122 mmol) was added and the mixture was stirred overnight at RT. The reaction was quenched with brine and diluted with DCM. The organic extract was washed with brine, dried over Na$_2$SO$_4$, and concentrated. The residue was dissolved in DCM (1 ml) and treated with TFA (1 mL, 12.98 mmol) at RT. The mixture was concentrated after 1 h and diluted with DCM. The organic layer was washed with saturated aqueous NaHCO$_3$, dried over Na$_2$SO$_4$, and concentrated. The residue was purified by reverse phase chromatography (Sunfire Prep C18; 20%-100% acetonitrile in water+0.05% TFA) to furnish the title compound. $^1$H NMR (500 MHz, DMSO-d$_6$) δ: 8.29 (s, 1H), 7.73 (s, 1H), 7.67 (m, 2H), 7.64 (m, 2H), 6.36 (s, 1H), 4.79 (s, 1H), 2.34 (s, 3H), 2.19 (s, 3H). MS=364.0 (M+1).

EXAMPLE 32

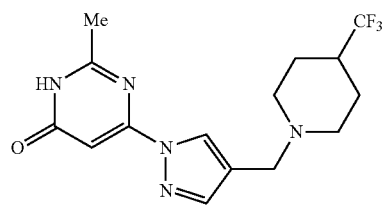 [SMILES: Cc1nc(-n2cc(CN3CCC(C(F)(F)F)CC3)cn2)cc(=O)[nH]1]

2-Methyl-6-(4-((4-(trifluoromethyl)piperidin-1-yl)methyl)-1H-pyrazol-1-yl)pyrimidin-4(3H)-one. (Scheme 38)

Step 1. 1-((1H-pyrazol-4-yl)methyl)-4-(trifluoromethyl)piperidine

1H-Pyrazole-4-carbaldehyde (100 mg, 1.041 mmol), 4-(trifluoromethyl)piperidine (159 mg, 1.041 mmol), sodium triacetoxyborohydride (441 mg, 2.081 mmol), and acetic acid (0.119 ml, 2.081 mmol) were combined in DCE (3 ml) and stirred overnight at RT. The reaction was then poured into a flask containing a saturated solution of NaHCO$_3$. After the bubbling ceased, the product was extracted with DCM. The organic extract was dried over Na$_2$SO$_4$, filtered, and concentrated. This material was used in the next step without further purification.

Step 2. 2-Methyl-6-(4-((4-(trifluoromethyl)piperidin-1-yl)methyl)-1H-pyrazol-1-yl)pyrimidin-4(3H)-one 4-Chloro-6-((4-methoxybenzyl)oxy)-2-methylpyrimidine (109 mg, 0.412 mmol), 1-((1H-pyrazol-4-yl)methyl)-4-(trifluoromethyl)piperidine (113 mg, 0.484 mmol), and cesium carbonate (158 mg, 0.484 mmol) were combined in DMF (0.8 ml) and heated to 80° C. for 16 h. The reaction was diluted with ethyl acetate and washed with brine (4×) to remove the DMF. The organic extract was dried over Na$_2$SO$_4$, filtered, and concentrated. The residue was then dissolved in DCM (1 ml) and treated with TFA (1 ml, 12.98 mmol). When the reaction was complete, as judged by LCMS, the volatiles were removed and the residue was purified by reverse phase chromatography (Biotage C-18 SNAP cartridge; 5-55% acetonitrile in water+0.05% TFA) to furnish the title compound.

$^1$H NMR (500 MHz, CDCl$_3$) δ: 12.88-12.32 (broad, 1H), 8.35 (s, 1H), 7.76 (s, 1H), 6.41 (s, 1H), 3.46 (s, 2H), 2.91-2.89 (m, 2H), 2.37 (s, 3H), 2.29-2.19 (broad, 1H), 1.96-1.91 (m, 2H), 1.78-1.75 (m, 2H), 1.48-1.40 (m, 2H). MS=342.0 (M+1).

Table 9—The compounds in Table 9 were prepared following the indicated methods/schemes therein. In cases where chiral HPLC was used to separate pairs of enantiomers, the fast-eluting isomer is always listed first in the table.

TABLE 9

| Example No. | Structure | IUPAC Name | Exact Mass [M + H]$^+$ | Chiral column | Methods |
|---|---|---|---|---|---|
| 33 | 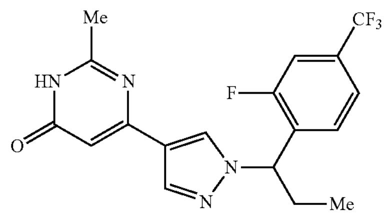 [SMILES: CCC(c1ccc(C(F)(F)F)cc1F)n1cc(-c2cc(=O)[nH]c(C)n2)cn1] | 6-(1-(1-(2-fluoro-4-(trifluoromethyl)phenyl)propyl)-1H-pyrazol-4-yl)-2-methylpyrimidin-4(3H)-one | Calc'd 381.1, found 381.1 | | Schemes 16 and 23 |
| 34 | 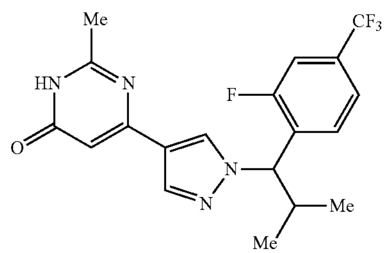 [SMILES: Cc1nc(-c2cnn(C(c3ccc(C(F)(F)F)cc3F)C(C)C)c2)cc(=O)[nH]1] | 6-(1-(1-(2-fluoro-4-(trifluoromethyl)phenyl)-2-methylpropyl)-1H-pyrazol-4-yl)-2-methylpyrimidin-4(3H)-one | Calc'd 395.1, found 395.1 | | Schemes 16 and 23 |
| 35 | 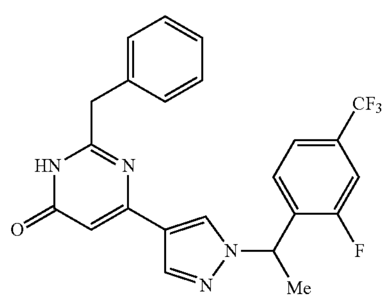 [SMILES: CC(c1ccc(C(F)(F)F)cc1F)n1cc(-c2cc(=O)[nH]c(Cc3ccccc3)n2)cn1] | 2-benzyl-6-(1-(1-(2-fluoro-4-(trifluoromethyl)phenyl)ethyl)-1H-pyrazol-4-yl)pyrimidin-4(3H)-one | Calc'd 443.1, found 443.1 | | Schemes 16 and 22 |
| 36 | 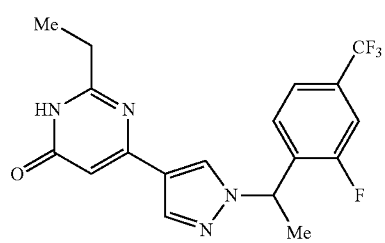 [SMILES: CCc1nc(-c2cnn(C(C)c3ccc(C(F)(F)F)cc3F)c2)cc(=O)[nH]1] | 2-ethyl-6-(1-(1-(2-fluoro-4-(trifluoromethyl)phenyl)ethyl)-1H-pyrazol-4-yl)pyrimidin-4(3H)-one | Calc'd 381.1, found 381.2 | | Schemes 16 and 22 |
| 37 | 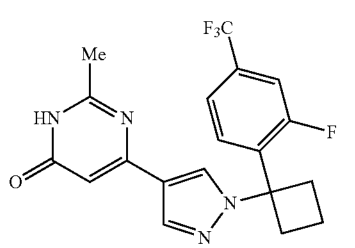 [SMILES: Cc1nc(-c2cnn(C3(c4ccc(C(F)(F)F)cc4F)CCC3)c2)cc(=O)[nH]1] | 6-(1-(1-(2-fluoro-4-(trifluoromethyl)phenyl)cyclobutyl)-1H-pyrazol-4-yl)-2-methylpyrimidin-4(3H)-one | Calc'd 393.1, found 393.3 | | Schemes 16 and 23 |

TABLE 9-continued

| Example No. | Structure | IUPAC Name | Exact Mass [M + H]⁺ | Chiral column | Methods |
|---|---|---|---|---|---|
| 38 | 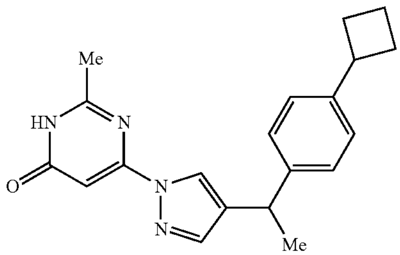 [SMILES: Cc1nc(-n2cc(C(C)c3ccc(C4CCC4)cc3)cn2)cc(=O)[nH]1] | 6-(4-(1-(4-cyclobutylphenyl)ethyl)-1H-pyrazol-1-yl)-2-methylpyrimidin-4(3H)-one | Calc'd 335.2, found 335.3 | | Scheme 20 |
| 39 | 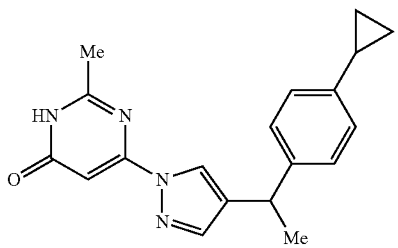 [SMILES: Cc1nc(-n2cc(C(C)c3ccc(C4CC4)cc3)cn2)cc(=O)[nH]1] | 6-(4-(1-(4-cyclopropylphenyl)ethyl)-1H-pyrazol-1-yl)-2-methylpyrimidin-4(3H)-one | Calc'd 321.2, found 321.2 | | Scheme 20 |
| 40 | 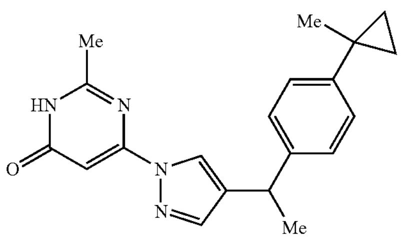 [SMILES: Cc1nc(-n2cc(C(C)c3ccc(C4(C)CC4)cc3)cn2)cc(=O)[nH]1] | 2-methyl-6-(4-(1-(4-(1-methylcyclopropyl)phenyl)ethyl)-1H-pyrazol-1-yl)pyrimidin-4(3H)-one | Calc'd 335.2, found 335.2 | | Scheme 20 |
| 41 | 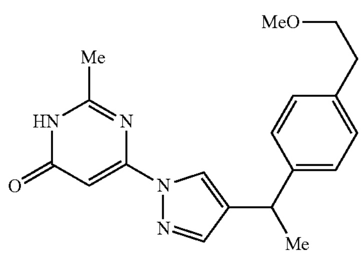 [SMILES: COCCc1ccc(C(C)c2cnn(-c3cc(=O)[nH]c(C)n3)c2)cc1] | 6-(4-(1-(4-(2-methoxyethyl)phenyl)ethyl)-1H-pyrazol-1-yl)-2-methylpyrimidin-4(3H)-one | Calc'd 339.2, found 339.2 | | Scheme 20 |
| 42 | 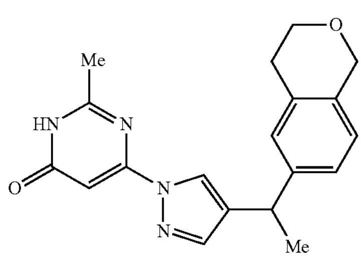 [SMILES: Cc1nc(-n2cc(C(C)c3ccc4c(c3)CCOC4)cn2)cc(=O)[nH]1] | 6-(4-(1-(isochroman-6-yl)ethyl)-1H-pyrazol-1-yl)-2-methylpyrimidin-4(3H)-one | Calc'd 337.2, found 337.2 | | Scheme 20 |
| 43 | 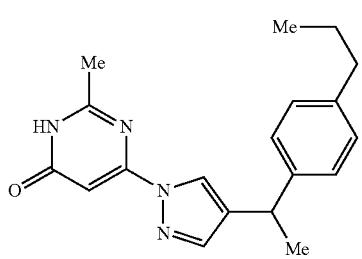 [SMILES: CCCc1ccc(C(C)c2cnn(-c3cc(=O)[nH]c(C)n3)c2)cc1] | 2-methyl-6-(4-(1-(4-propylphenyl)ethyl)-1H-pyrazol-1-yl)pyrimidin-4(3H)-one | Calc'd 323.2, found 323.2 | | Scheme 20 |

TABLE 9-continued

| Example No. | Structure | IUPAC Name | Exact Mass [M + H]+ | Chiral column | Methods |
|---|---|---|---|---|---|
| 44 | 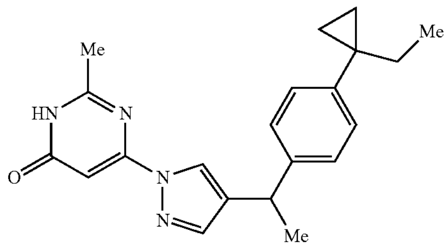 [SMILES: CCC1(c2ccc(C(C)c3cnn(-c4cc(=O)[nH]c(C)n4)c3)cc2)CC1] | 6-(4-(1-(4-(1-ethylcyclopropyl)phenyl)ethyl)-1H-pyrazol-1-yl)-2-methylpyrimidin-4(3H)-one | Calc'd 349.2, found 349.2 | | Scheme 20 |
| 45 | 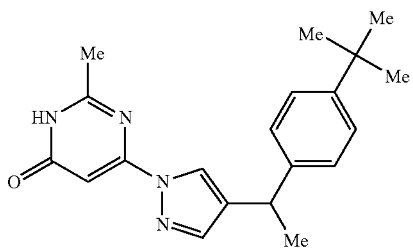 [SMILES: Cc1nc(-n2cc(C(C)c3ccc(C(C)(C)C)cc3)cn2)cc(=O)[nH]1] | 6-(4-(1-(4-(tert-butyl)phenyl)ethyl)-1H-pyrazol-1-yl)-2-methylpyrimidin-4(3H)-one | Calc'd 337.2, found 337.3 | | Scheme 20 |
| 46 | 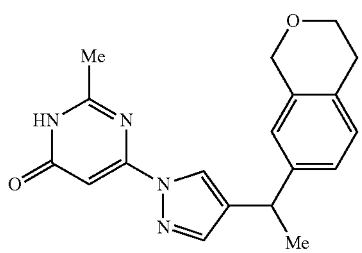 [SMILES: Cc1nc(-n2cc(C(C)c3ccc4c(c3)COCC4)cn2)cc(=O)[nH]1] | 6-(4-(1-(isochroman-7-yl)ethyl)-1H-pyrazol-1-yl)-2-methylpyrimidin-4(3H)-one | Calc'd 337.2, found 337.2 | | Scheme 20 |
| 47 | 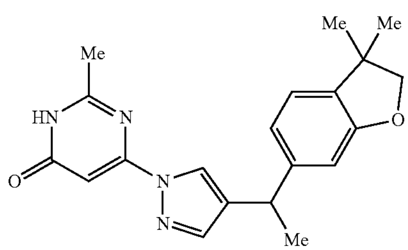 [SMILES: Cc1nc(-n2cc(C(C)c3ccc4c(c3)OCC4(C)C)cn2)cc(=O)[nH]1] | 6-(4-(1-(3,3-dimethyl-2,3-dihydrobenzofuran-6-yl)ethyl)-1H-pyrazol-1-yl)-2-methylpyrimidin-4(3H)-one | Calc'd 351.2, found 351.2 | | Scheme 20 |
| 48 | 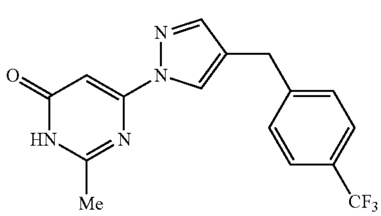 [SMILES: Cc1nc(-n2cc(Cc3ccc(C(F)(F)F)cc3)cn2)cc(=O)[nH]1] | 2-methyl-6-(4-(4-(trifluoromethyl)benzyl)-1H-pyrazol-1-yl)pyrimidin-4(3H)-one | Calc'd 335.1, found 335.0 | | Scheme 20 |
| 49 | 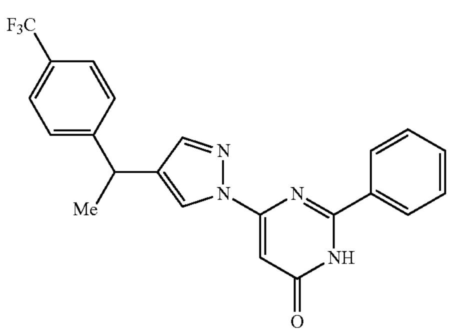 [SMILES: CC(c1ccc(C(F)(F)F)cc1)c1cnn(-c2cc(=O)[nH]c(-c3ccccc3)n2)c1] | 2-phenyl-6-(4-(1-(4-(trifluoromethyl)phenyl)ethyl)-1H-pyrazol-1-yl)pyrimidin-4(3H)-one | Calc'd 411.1, found 411.0 | | Scheme 20 |

TABLE 9-continued

| Example No. | Structure | IUPAC Name | Exact Mass [M + H]+ | Chiral column | Methods |
|---|---|---|---|---|---|
| 50 | 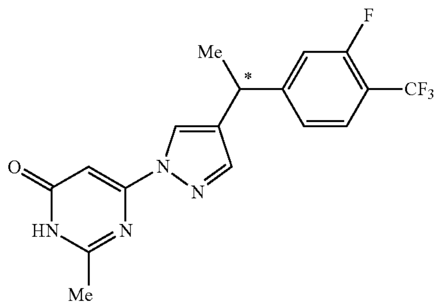 [SMILES: Cc1nc(-n2cc(C(C)c3ccc(C(F)(F)F)c(F)c3)cn2)cc(=O)[nH]1] | (R)- or (S)-6-(4-(1-(3-fluoro-4-(trifluoromethyl)phenyl)ethyl)-1H-pyrazol-1-yl)-2-methylpyrimidin-4(3H)-one | Calc'd 367.1, found 367.0 | Chiralpak ID | Scheme 20 |
| 51 | 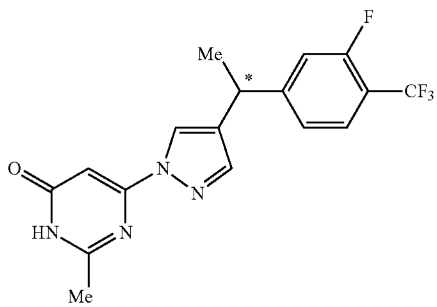 [SMILES: Cc1nc(-n2cc(C(C)c3ccc(C(F)(F)F)c(F)c3)cn2)cc(=O)[nH]1] | (S)- or (R)-6-(4-(1-(3-fluoro-4-(trifluoromethyl)phenyl)ethyl)-1H-pyrazol-1-yl)-2-methylpyrimidin-4(3H)-one | Calc'd 367.1, found 367.0 | Chiralpak ID | Scheme 20 |
| 52 | 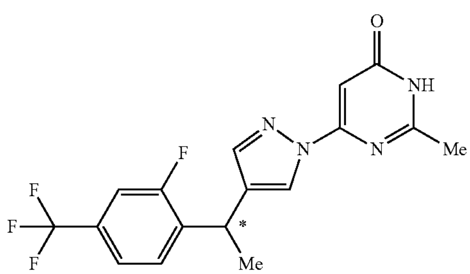 [SMILES: Cc1nc(-n2cc(C(C)c3ccc(C(F)(F)F)cc3F)cn2)cc(=O)[nH]1] | (R)- or (S)-6-(4-(1-(2-fluoro-4-(trifluoromethyl)phenyl)ethyl)-1H-pyrazol-1-yl)-2-methylpyrimidin-4(3H)-one | Calc'd 367.1, found 367.2 | Lux Cellulose-4 | Scheme 20 |
| 53 | 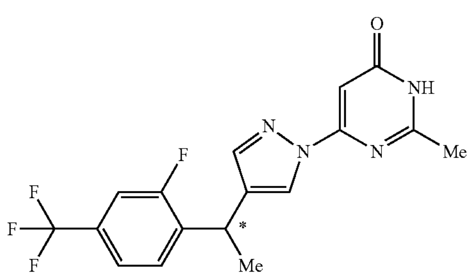 [SMILES: Cc1nc(-n2cc(C(C)c3ccc(C(F)(F)F)cc3F)cn2)cc(=O)[nH]1] | (S)- or (R)-6-(4-(1-(2-fluoro-4-(trifluoromethyl)phenyl)ethyl)-1H-pyrazol-1-yl)-2-methylpyrimidin-4(3H)-one | Calc'd 367.1, found 367.1 | Lux Cellulose-4 | Scheme 20 |
| 54 | 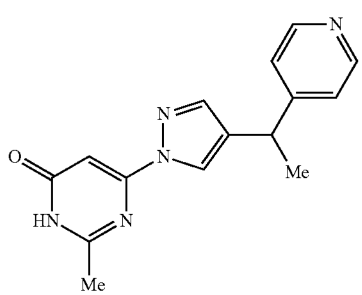 [SMILES: Cc1nc(-n2cc(C(C)c3ccncc3)cn2)cc(=O)[nH]1] | 2-methyl-6-[4-(1-pyridin-4-ylethyl)-1H-pyrazol-1-yl]pyrimidin-4(3H)-one | Calc'd 282.1, found 282.2 | | Scheme 20 |

TABLE 9-continued

| Example No. | Structure | IUPAC Name | Exact Mass [M + H]+ | Chiral column | Methods |
|---|---|---|---|---|---|
| 55 | 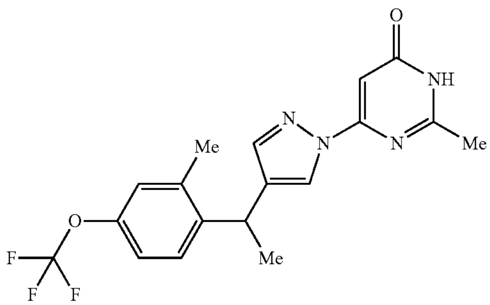 [SMILES: Cc1nc(-n2cc(C(C)c3ccc(OC(F)(F)F)cc3C)cn2)cc(=O)[nH]1] | 2-methyl-6-(4-(1-(2-methyl-4-(trifluoromethoxy)phenyl)ethyl)-1H-pyrazol-1-yl)pyrimidin-4(3H)-one | Calc'd 379.1, found 379.1 | | Scheme 20 |
| 56 | 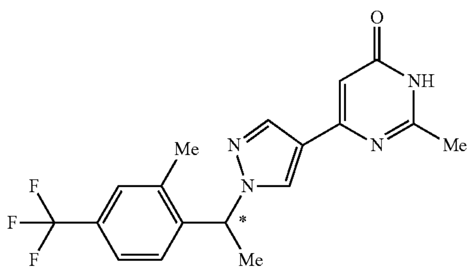 [SMILES: Cc1nc(-c2cnn(C(C)c3ccc(C(F)(F)F)cc3C)c2)cc(=O)[nH]1] | (R)- or (S)-2-methyl-6-(1-(1-(2-methyl-4-(trifluoromethyl)phenyl)ethyl)-1H-pyrazol-4-yl)pyrimidin-4(3H)-one | Calc'd 363.1, found 363.0 | Chiralpak IC | Scheme 19 |
| 57 | 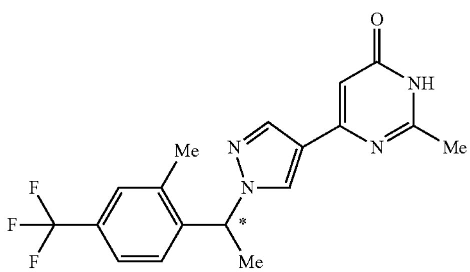 [SMILES: Cc1nc(-c2cnn(C(C)c3ccc(C(F)(F)F)cc3C)c2)cc(=O)[nH]1] | (S)- or (R)-2-methyl-6-(1-(1-(2-methyl-4-(trifluoromethyl)phenyl)ethyl)-1H-pyrazol-4-yl)pyrimidin-4(3H)-one | Calc'd 363.1, found 363.0 | Chiralpak IC | Scheme 19 |
| 58 | 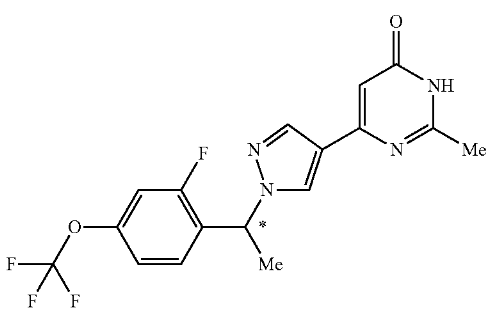 [SMILES: Cc1nc(-c2cnn(C(C)c3ccc(OC(F)(F)F)cc3F)c2)cc(=O)[nH]1] | (R)- or (S)-6-(1-(1-(2-fluoro-4-(trifluoromethoxy)phenyl)ethyl)-1H-pyrazol-4-yl)-2-methylpyrimidin-4(3H)-one | Calc'd 383.1, found 383.0 | Chiralpak IC | Scheme 19 |
| 59 | 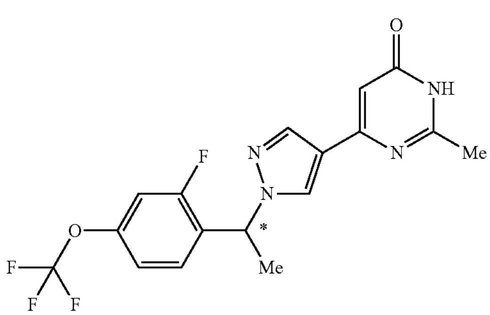 [SMILES: Cc1nc(-c2cnn(C(C)c3ccc(OC(F)(F)F)cc3F)c2)cc(=O)[nH]1] | (S)- or (R)-6-(1-(1-(2-fluoro-4-(trifluoromethoxy)phenyl)ethyl)-1H-pyrazol-4-yl)-2-methylpyrimidin-4(3H)-one | Calc'd 383.1, found 383.0 | Chiralpak IC | Scheme 19 |

TABLE 9-continued

| Example No. | Structure | IUPAC Name | Exact Mass [M + H]+ | Chiral column | Methods |
|---|---|---|---|---|---|
| 60 | 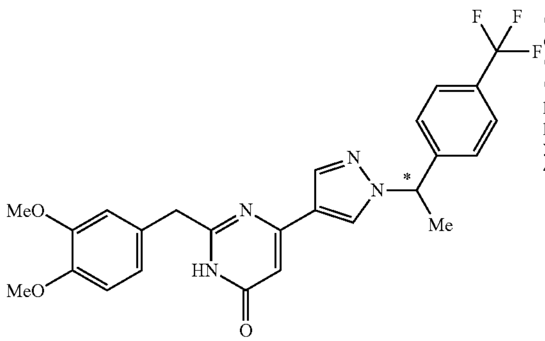 [SMILES: COc1ccc(Cc2nc(-c3cnn(C(C)c4ccc(C(F)(F)F)cc4)c3)cc(=O)[nH]2)cc1OC] | (R)- or (S)-2-(3,4-dimethoxybenzyl)-6-(1-(1-4-(trifluoromethyl)phenyl)ethyl)-1H-pyrazol-4-yl)pyrimidin-4(3H)-one | Calc'd 485.2, found 485.1 | Chiralpak IC | Schemes 17 and 20 |
| 61 | 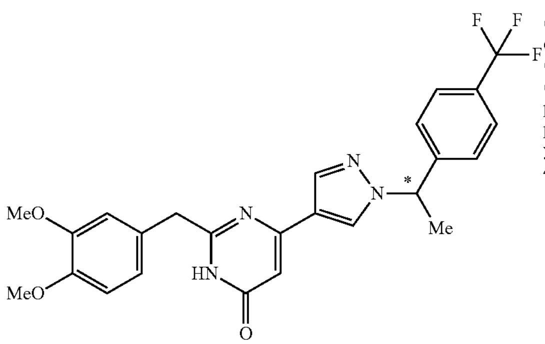 [SMILES: COc1ccc(Cc2nc(-c3cnn(C(C)c4ccc(C(F)(F)F)cc4)c3)cc(=O)[nH]2)cc1OC] | (S)- or (R)-2-(3,4-dimethoxybenzyl)-6-(1-(1-(4-(trifluoromethyl)phenyl)ethyl)-1H-pyrazol-4-yl)pyrimidin-4(3H)-one | Calc'd 485.2, found 485.1 | Chiralpak IC | Schemes 17 and 20 |
| 62 | 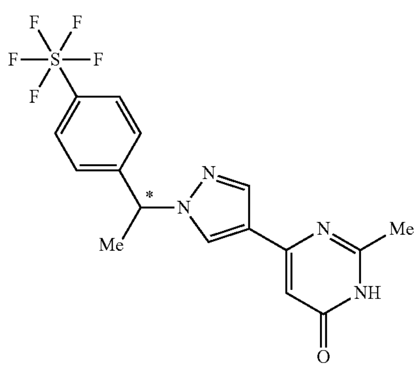 [SMILES: Cc1nc(-c2cnn(C(C)c3ccc(S(F)(F)(F)(F)F)cc3)c2)cc(=O)[nH]1] | (R)- or (S)-2-methyl-6-(1-(1-(4-(pentafluorosulfanyl)phenyl)ethyl)-1H-pyrazol-4-yl)pyrimidin-4(3H)-one | Calc'd 407.1, found 407.0 | Lux Cellulose-4 | Scheme 19 |
| 63 | 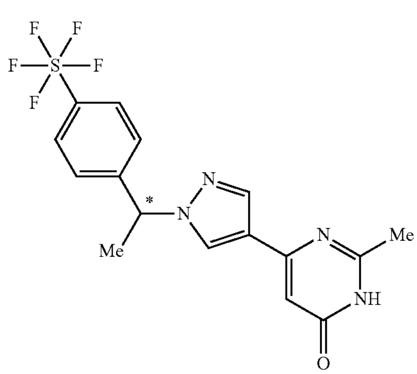 [SMILES: Cc1nc(-c2cnn(C(C)c3ccc(S(F)(F)(F)(F)F)cc3)c2)cc(=O)[nH]1] | (S)- or (R)-2-methyl-6-(1-(1-(4-(pentafluorosulfanyl)phenyl)ethyl)-1H-pyrazol-4-yl)pyrimidin-4(3H)-one | Calc'd 407.1, found 407.0 | Lux Cellulose-4 | Scheme 19 |

TABLE 9-continued

| Example No. | Structure | IUPAC Name | Exact Mass [M + H]+ | Chiral column | Methods |
|---|---|---|---|---|---|
| 64 | 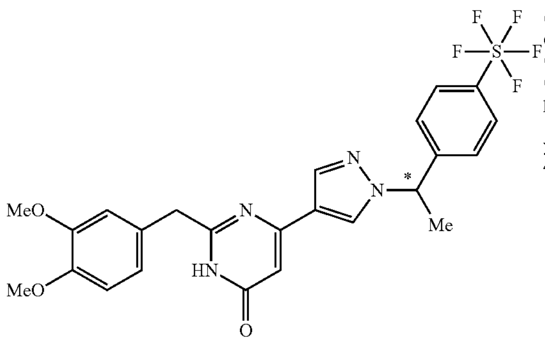 [SMILES: COc1ccc(Cc2nc(-c3cnn(C(C)c4ccc(S(F)(F)(F)(F)F)cc4)c3)cc(=O)[nH]2)cc1OC] | (R)- or (S)-2-(3,4-dimethoxybenzyl)-6-(1-(1-(4-(pentafluorosulfanyl)phenyl)ethyl)-1H-pyrazol-4-yl)pyrimidin-4(3H)-one | Calc'd 543.1, found 543.1 | Chiralpak OJ-H | Scheme 19 |
| 65 | 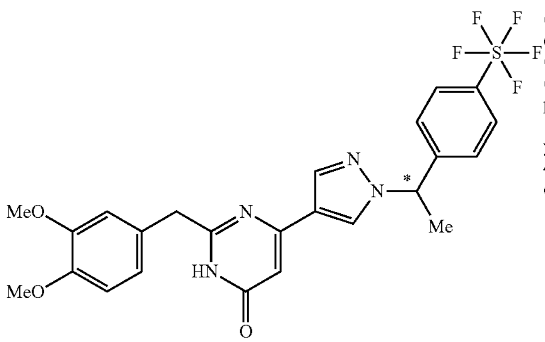 [SMILES: COc1ccc(Cc2nc(-c3cnn(C(C)c4ccc(S(F)(F)(F)(F)F)cc4)c3)cc(=O)[nH]2)cc1OC] | (S)- or (R)-2-(3,4-dimethoxybenzyl)-6-(1-(1-(4-(pentafluorosulfanyl)phenyl)ethyl)-1H-pyrazol-4-yl)pyrimidin-4(3H)-one 4(3H)-one | Calc'd 543.1, found 543.1 | Chiralpak OJ-H | Scheme 19 |
| 66 | 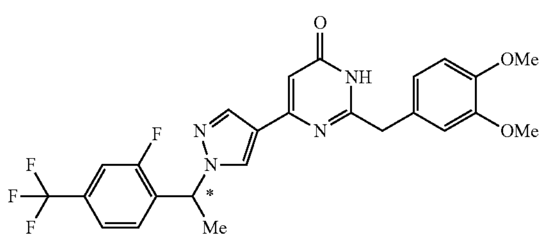 [SMILES: COc1ccc(Cc2nc(-c3cnn(C(C)c4ccc(C(F)(F)F)cc4F)c3)cc(=O)[nH]2)cc1OC] | (R)- or (S)-2-(3,4-dimethoxybenzyl)-6-(1-(1-(2-fluoro-4-(trifluoromethyl)phenyl)ethyl)-1H-pyrazol-4-yl)pyrimidin-4(3H)-one | Calc'd 503.2, found 503.1 | Chiralpak OJ-H | Scheme 19 |
| 67 | 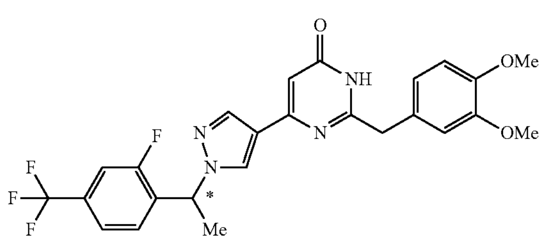 [SMILES: COc1ccc(Cc2nc(-c3cnn(C(C)c4ccc(C(F)(F)F)cc4F)c3)cc(=O)[nH]2)cc1OC] | (S)- or (R)-2-(3,4-dimethoxybenzyl)-6-(1-(1-(2-fluoro-4-(trifluoromethyl)phenyl)ethyl)-1H-pyrazol-4-yl)pyrimidin- | Calc'd 503.2, found 503.1 | Chiralpak OJ-H | Scheme 19 |
| 68 | 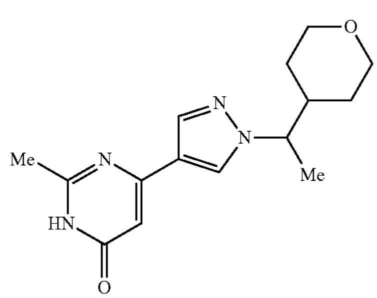 [SMILES: Cc1nc(-c2cnn(C(C)C3CCOCC3)c2)cc(=O)[nH]1] | 2-methyl-6-(1-(1-(tetrahydro-2H-pyran-4-yl)ethyl)-1H-pyrazol-4-yl)pyrimidin-4(3H)-one | Calc'd 289.2, found 289.0 | | Scheme 19 |

TABLE 9-continued

| Example No. | Structure | IUPAC Name | Exact Mass [M + H]+ | Chiral column | Methods |
|---|---|---|---|---|---|
| 69 | 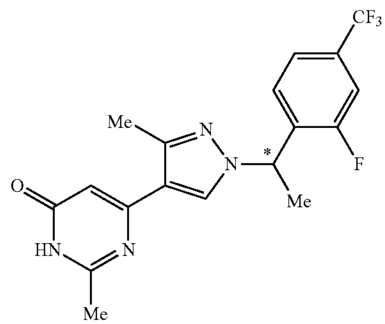 [SMILES: Cc1nc(-c2cn(C(C)c3ccc(C(F)(F)F)cc3F)nc2C)cc(=O)[nH]1] | (R)- or (S)-(6-(1-(1-(2-fluoro-4-(trifluoromethyl)phenyl)ethyl)-3-methyl-1H-pyrazol-4-yl)-2-methylpyrimidin-4(3H)-one | Calc'd 381.1, found 380.9 | Chiralpak OZ-H | Scheme 19 |
| 70 | 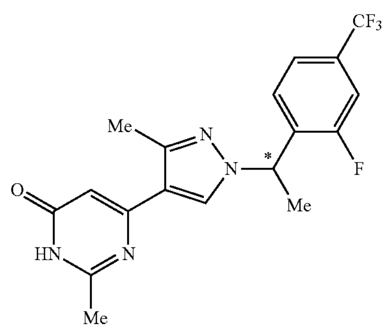 [SMILES: Cc1nc(-c2cn(C(C)c3ccc(C(F)(F)F)cc3F)nc2C)cc(=O)[nH]1] | (S)- or (R)-(6-(1-(1-(2-fluoro-4-(trifluoromethyl)phenyl)ethyl)-3-methyl-1H-pyrazol-4-yl)-2-methylpyrimidin-4(3H)-one | Calc'd 381.1, found 380.9 | Chiralpak OZ-H | Scheme 19 |
| 71 | 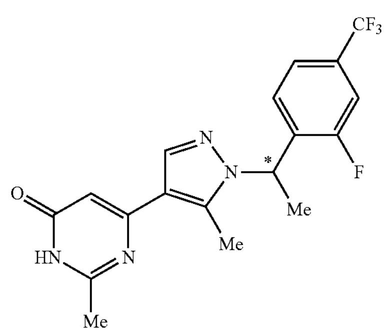 [SMILES: Cc1nc(-c2cnn(C(C)c3ccc(C(F)(F)F)cc3F)c2C)cc(=O)[nH]1] | (R)- or (S)-6-(1-(1-(2-fluoro-4-(trifluoromethyl)phenyl)ethyl)-5-methyl-1H-pyrazol-4-yl)-2-methylpyrimidin-4(3H)-one | Calc'd 381.1, found 380.9 | Chiralpak OD-H | Scheme 19 |
| 72 | 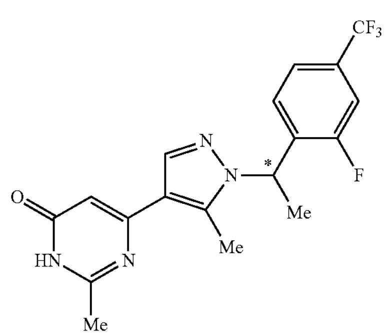 [SMILES: Cc1nc(-c2cnn(C(C)c3ccc(C(F)(F)F)cc3F)c2C)cc(=O)[nH]1] | (S)- or (R)-6-(1-(1-(2-fluoro-4-(trifluoromethyl)phenyl)ethyl)-5-methyl-1H-pyrazol-4-yl)-2-methylpyrimidin-4(3H)-one | Calc'd 381.1, found 380.9 | Chiralpak OD-H | Scheme 19 |

TABLE 9-continued

| Example No. | Structure | IUPAC Name | Exact Mass [M + H]+ | Chiral column | Methods |
|---|---|---|---|---|---|
| 73 | 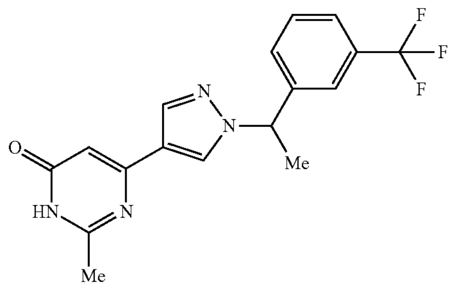 [SMILES: Cc1nc(-c2cnn(C(C)c3cccc(C(F)(F)F)c3)c2)cc(=O)[nH]1] | 2-methyl-6-(1-(1-(3-(trifluoromethyl)phenyl)ethyl)-1H-pyrazol-4-yl)pyrimidin-4(3H)-one | Calc'd 349.1, found 349.1 | | Schemes 19 and 22 |
| 74 | 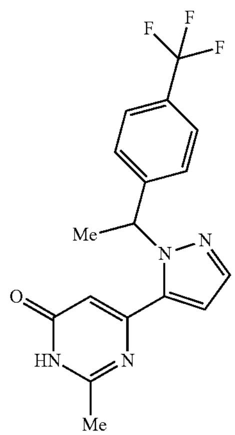 [SMILES: Cc1nc(-c2ccnn2C(C)c2ccc(C(F)(F)F)cc2)cc(=O)[nH]1] | 2-methyl-6-(1-(1-(4-(trifluoromethyl)phenyl)ethyl)-1H-pyrazol-5-yl)pyrimidin-4(3H)-one | Calc'd 349.1, found 349.0 | | Scheme 19 |
| 75 | 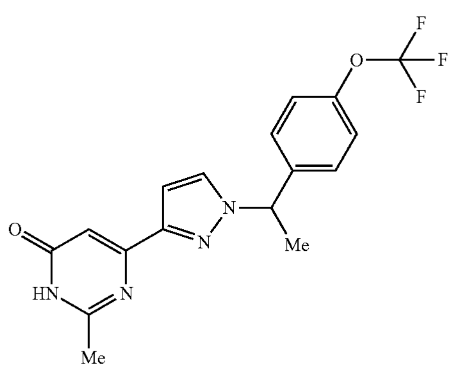 [SMILES: Cc1nc(-c2ccn(C(C)c3ccc(OC(F)(F)F)cc3)n2)cc(=O)[nH]1] | 2-methyl-6-(1-(1-(4-(trifluoromethoxy)phenyl)ethyl)-1H-pyrazol-3-yl)pyrimidin-4(3H)-one | Calc'd 365.0, found 365.1 | | Scheme 19 |
| 76 | 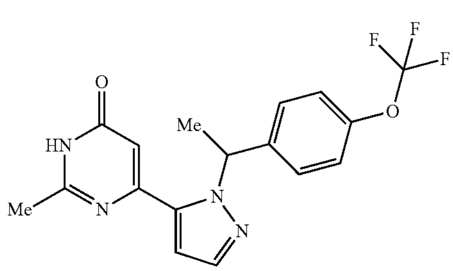 [SMILES: Cc1nc(-c2ccnn2C(C)c2ccc(OC(F)(F)F)cc2)cc(=O)[nH]1] | 2-methyl-6-(1-(1-(4-(trifluoromethoxy)phenyl)ethyl)-1H-pyrazol-5-yl)pyrimidin-4(3H)-one | Calc'd 365.0, found 365.1 | | Scheme 19 |

TABLE 9-continued

| Example No. | Structure | IUPAC Name | Exact Mass [M + H]$^+$ | Chiral column | Methods |
|---|---|---|---|---|---|
| 77 | 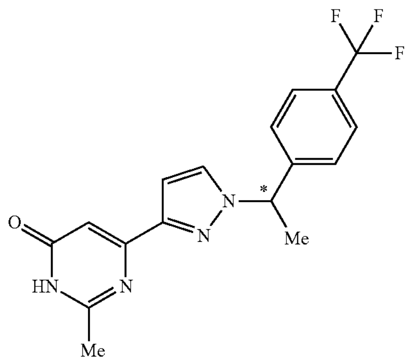 [SMILES: Cc1nc(-c2ccn(C(C)c3ccc(C(F)(F)F)cc3)n2)cc(=O)[nH]1] | (R)- or (S)-2-methyl-6-(1-(1-(4-(trifluoromethyl)phenyl)ethyl)-1H-pyrazol-3-yl)pyrimidin-4(3H)-one | Calc'd 349.1, found 349.0 | Chiralpak AD | Scheme 19 |
| 78 | 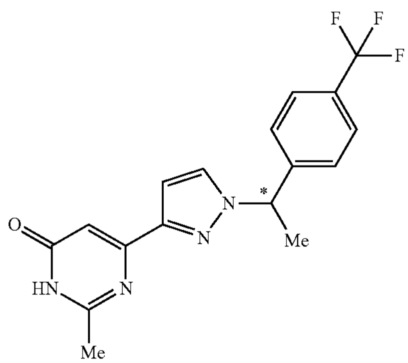 [SMILES: Cc1nc(-c2ccn(C(C)c3ccc(C(F)(F)F)cc3)n2)cc(=O)[nH]1] | (S)- or (R)-2-methyl-6-(1-{(1R)-1-[4-(trifluoromethyl)phenyl]ethyl}-1H-pyrazol-3-yl)pyrimidin-4(3H)-one | Calc'd 349.1, found 349.0 | Chiralpak AD | Scheme 19 |
| 79 | 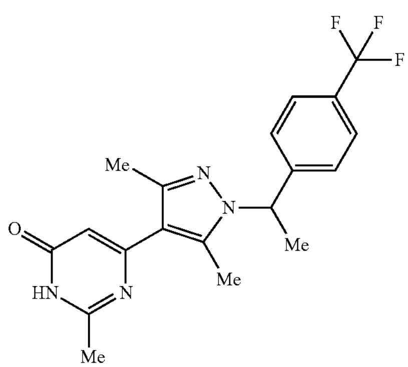 [SMILES: Cc1nc(-c2c(C)nn(C(C)c3ccc(C(F)(F)F)cc3)c2C)cc(=O)[nH]1] | 6-(3,5-dimethyl-1-(1-(4-(trifluoromethyl)phenyl)ethyl)-1H-pyrazol-4-yl)-2-methylpyrimidin-4(3H)-one | Calc'd 377.1, found 377.1 | | Scheme 19 |
| 80 | 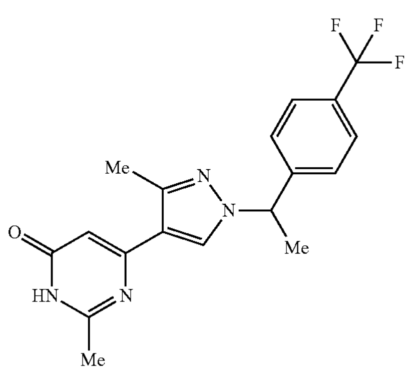 [SMILES: Cc1nc(-c2cn(C(C)c3ccc(C(F)(F)F)cc3)nc2C)cc(=O)[nH]1] | 2-methyl-6-(3-methyl-1-(1-(4-(trifluoromethyl)phenyl)ethyl)-1H-pyrazol-4-yl)pyrimidin-4(3H)-one | Calc'd 363.1, found 363.1 | | Scheme 19 |

TABLE 9-continued

| Example No. | Structure | IUPAC Name | Exact Mass [M + H]+ | Chiral column | Methods |
|---|---|---|---|---|---|
| 81 | 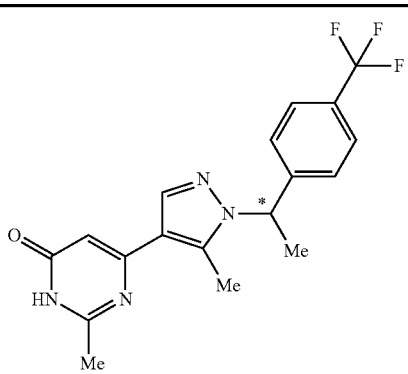 | (R)- or (S)-2-methyl-6-(5-methyl-1-(1-(4-(trifluoromethyl)phenyl)ethyl)-1H-pyrazol-4-yl)pyrimidin-4(3H)-one | Calc'd 363.1, found 363.1 | Chiralpak IC | Scheme 19 |
| 82 | 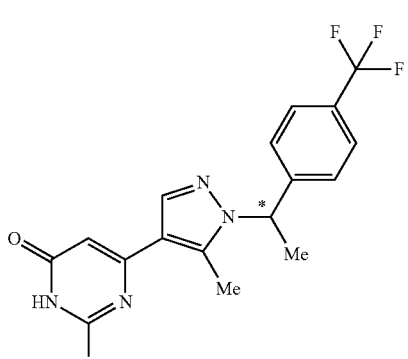 | (S)- or (R)-2-methyl-6-(5-methyl-1-{(1R)-1-[4-(trifluoromethyl)phenyl]ethyl}-1H-pyrazol-4-yl)pyrimidin-4(3H)-one | Calc'd 363.1, found 363.1 | Chiralpak IC | Scheme 19 |
| 83 | 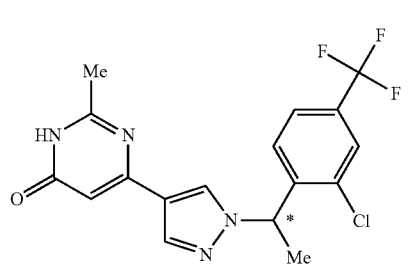 | (R)- or (S)-6-(1-(1-(2-chloro-4-(trifluoromethyl)phenyl)ethyl)-1H-pyrazol-4-yl)-2-methylpyrimidin-4(3H)-one | Calc'd 383.1, found 383.1 | Chiralpak IA | Schemes 16 and 23 |
| 84 | 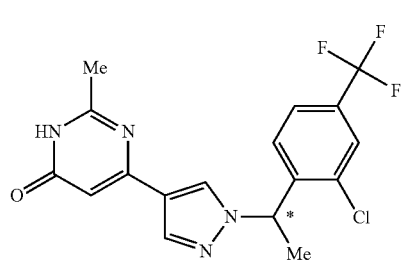 [SMILES: Cc1nc(-c2cnn(C(C)c3ccc(C(F)(F)F)cc3Cl)c2)cc(=O)[nH]1] | (S)- or (R)-6-(1-(1-(2-chloro-4-(trifluoromethyl)phenyl)ethyl)-1H-pyrazol-4-yl)-2-methylpyrimidin-4(3H)-one | Calc'd 383.1, found 383.1 | Chiralpak IA | Schemes 16 and 23 |
| 85 | 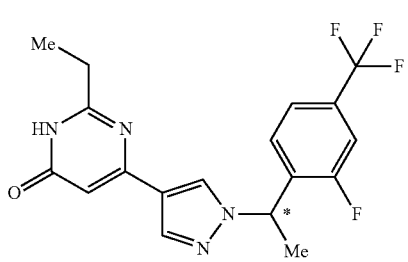 [SMILES: CCc1nc(-c2cnn(C(C)c3ccc(C(F)(F)F)cc3F)c2)cc(=O)[nH]1] | (R)- or (S)-2-ethyl-6-(1-(1-(2-fluoro-4-(trifluoromethyl)phenyl)ethyl)-1H-pyrazol-4-yl)pyrimidin-4(3H)-one | Calc'd 381.1, found 381.1 | Chiralpak IA | Schemes 16 and 22 |

TABLE 9-continued

| Example No. | Structure | IUPAC Name | Exact Mass [M + H]+ | Chiral column | Methods |
|---|---|---|---|---|---|
| 86 | 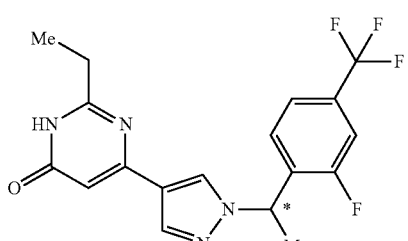 | (S)- or (R)-2-ethyl-6-(1-(1-(2-fluoro-4-(trifluoromethyl)phenyl)ethyl)-1H-pyrazol-4-yl)pyrimidin-4(3H)-one | Calc'd 381.1, found 381.1 | Chiralpak IA | Schemes 16 and 22 |
| 87 | 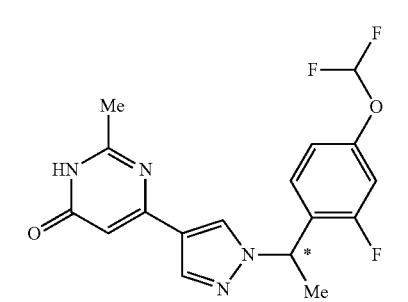 [SMILES: Cc1nc(-c2cnn(C(C)c3ccc(OC(F)F)cc3F)c2)cc(=O)[nH]1] | (R)- or (S)-6-(1-(1-(4-(difluoromethoxy)-2-fluorophenyl)ethyl)-1H-pyrazol-4-yl)-2-methylpyrimidin-4(3H)-one | Calc'd 365.1, found 365.1 | Chiralpak AS-H | Schemes 17 and 22 |
| 88 | 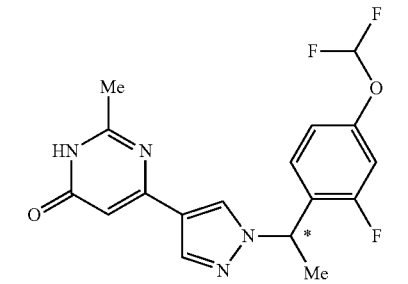 [SMILES: Cc1nc(-c2cnn(C(C)c3ccc(OC(F)F)cc3F)c2)cc(=O)[nH]1] | (S)- or (R)-6-(1-(1-(4-(difluoromethoxy)-2-fluorophenyl)ethyl)-1H-pyrazol-4-yl)-2-methylpyrimidin-4(3H)-one | Calc'd 365.1, found 365.1 | Chiralpak AS-H | Schemes 17 and 22 |
| 89 | 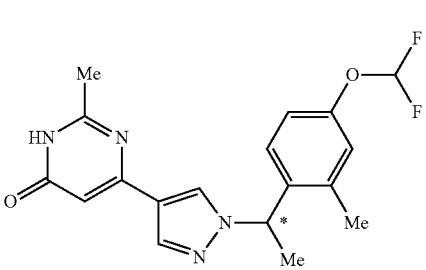 [SMILES: Cc1nc(-c2cnn(C(C)c3ccc(OC(F)F)cc3C)c2)cc(=O)[nH]1] | (R)- or (S)-6-(1-(1-(4-(difluoromethoxy)-2-methylphenyl)ethyl)-1H-pyrazol-4-yl)-2-methylpyrimidin-4(3H)-one | Calc'd 361.1, found 361.1 | Chiralpak IA | Schemes 17 and 22 |
| 90 | 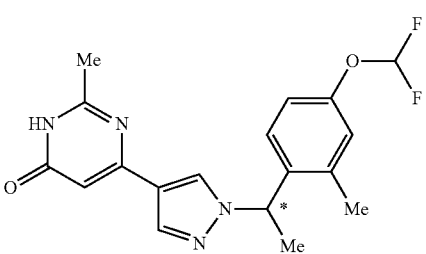 [SMILES: Cc1nc(-c2cnn(C(C)c3ccc(OC(F)F)cc3C)c2)cc(=O)[nH]1] | (S)- or (R)-6-(1-(1-(4-(difluoromethoxy)-2-methylphenyl)ethyl)-1H-pyrazol-4-yl)-2-methylpyrimidin-4(3H)-one | Calc'd 361.1, found 361.1 | Chiralpak IA | Schemes 17 and 22 |

TABLE 9-continued

| Example No. | Structure | IUPAC Name | Exact Mass [M + H]+ | Chiral column | Methods |
|---|---|---|---|---|---|
| 91 | 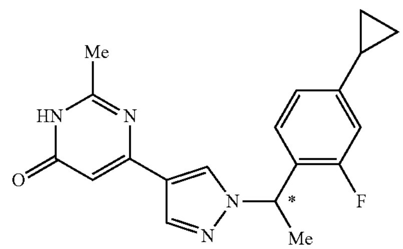 [SMILES: Cc1nc(-c2cnn(C(C)c3ccc(C4CC4)cc3F)c2)cc(=O)[nH]1] | (R)- or (S)-6-(1-(1-(4-cyclopropyl-2-fluorophenyl)ethyl)-1H-pyrazol-4-yl)-2-methylpyrimidin-4(3H)-one | Calc'd 339.2, found 339.2 | Lux Cellulose-4 | Schemes 17 and 22 |
| 92 | 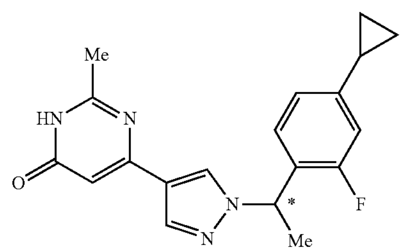 [SMILES: Cc1nc(-c2cnn(C(C)c3ccc(C4CC4)cc3F)c2)cc(=O)[nH]1] | (S)- or (R)-6-(1-(1-(4-cyclopropyl-2-fluorophenyl)ethyl)-1H-pyrazol-4-yl)-2-methylpyrimidin-4(3H)-one | Calc'd 339.2, found 339.2 | Lux Cellulose-4 | Schemes 17 and 22 |
| 93 | 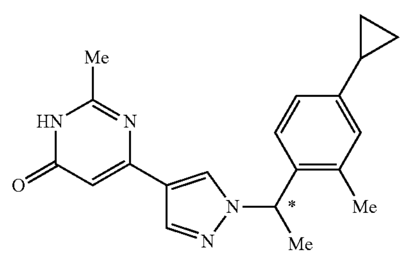 [SMILES: Cc1nc(-c2cnn(C(C)c3ccc(C4CC4)cc3C)c2)cc(=O)[nH]1] | (R)- or (S)-6-(1-(1-(4-cyclopropyl-2-methylphenyl)ethyl)-1H-pyrazol-4-yl)-2-methylpyrimidin-4(3H)-one | Calc'd 335.2, found 335.0 | Chiralpak IA | Schemes 17 and 22 |
| 94 | 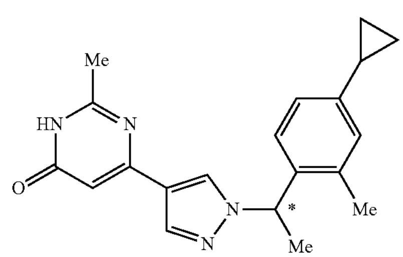 [SMILES: Cc1nc(-c2cnn(C(C)c3ccc(C4CC4)cc3C)c2)cc(=O)[nH]1] | (S)- or (R)-6-(1-(1-(4-cyclopropyl-2-methylphenyl)ethyl)-1H-pyrazol-4-yl)-2-methylpyrimidin-4(3H)-one | Calc'd 335.2, found 335.0 | Chiralpak IA | Schemes 17 and 22 |
| 95 | 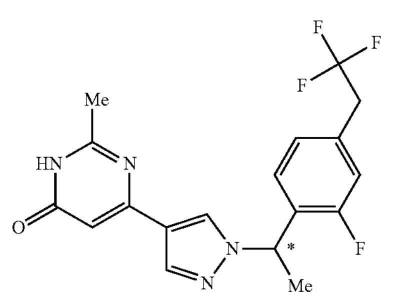 [SMILES: Cc1nc(-c2cnn(C(C)c3ccc(CC(F)(F)F)cc3F)c2)cc(=O)[nH]1] | (R)- or (S)-6-(1-(1-(2-fluoro-4-(2,2,2-trifluoroethyl)phenyl)ethyl)-1H-pyrazol-4-yl)-2-methylpyrimidin-4(3H)-one | Calc'd 381.1, found 381.1 | Chiralpak IC | Schemes 17 and 22 |

TABLE 9-continued

| Example No. | Structure | IUPAC Name | Exact Mass [M + H]⁺ | Chiral column | Methods |
|---|---|---|---|---|---|
| 96 | 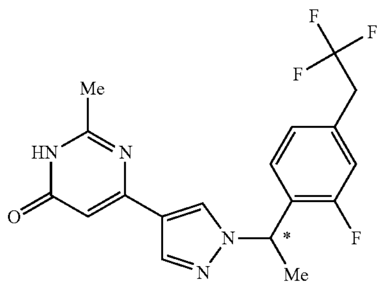 [SMILES: Cc1nc(-c2cnn(C(C)c3ccc(CC(F)(F)F)cc3F)c2)cc(=O)[nH]1] | (S)- or (R)-6-(1-(1-(2-fluoro-4-(2,2,2-trifluoroethyl)phenyl)ethyl)-1H-pyrazol-4-yl)-2-methylpyrimidin-4(3H)-one | Calc'd 381.1, found 381.1 | Chiralpak IC | Schemes 17 and 22 |
| 97 | 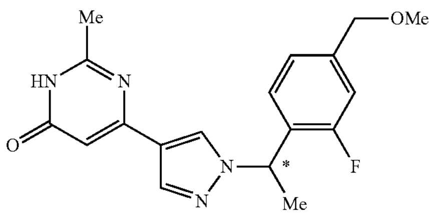 [SMILES: COCc1ccc(C(C)n2cc(-c3cc(=O)[nH]c(C)n3)cn2)c(F)c1] | (R)- or (S)-6-(1-(1-(2-fluoro-4-(methoxymethyl)phenyl)ethyl)-1H-pyrazol-4-yl)-2-methylpyrimidin-4(3H)-one | Calc'd 343.2, found 343.2 | Chiralpak IC | Schemes 17 and 22 |
| 98 | 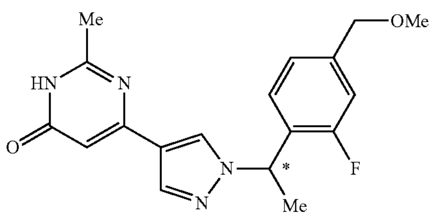 [SMILES: COCc1ccc(C(C)n2cc(-c3cc(=O)[nH]c(C)n3)cn2)c(F)c1] | (S)- or (R)-6-(1-(1-(2-fluoro-4-(methoxymethyl)phenyl)ethyl)-1H-pyrazol-4-yl)-2-methylpyrimidin-4(3H)-one | Calc'd 343.2, found 343.2 | Chiralpak IC | Schemes 17 and 22 |
| 99 | 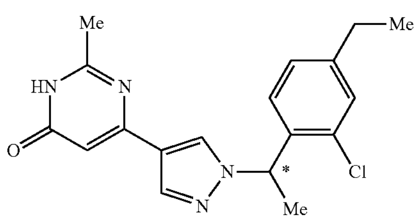 [SMILES: CCc1ccc(C(C)n2cc(-c3cc(=O)[nH]c(C)n3)cn2)c(Cl)c1] | (R)- or (S)-6-(1-(1-(2-chloro-4-ethylphenyl)ethyl)-1H-pyrazol-4-yl)-2-methylpyrimidin-4(3H)-one | Calc'd 343.1, found 343.2 | Chiralpak IC | Schemes 17 and 22 |
| 100 | 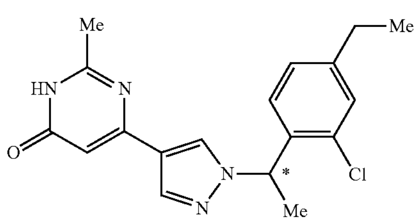 [SMILES: CCc1ccc(C(C)n2cc(-c3cc(=O)[nH]c(C)n3)cn2)c(Cl)c1] | (S)- or (R)-6-(1-(1-(2-chloro-4-ethylphenyl)ethyl)-1H-pyrazol-4-yl)-2-methylpyrimidin-4(3H)-one | Calc'd 343.1, found 343.2 | Chiralpak IC | Schemes 17 and 22 |
| 101 | 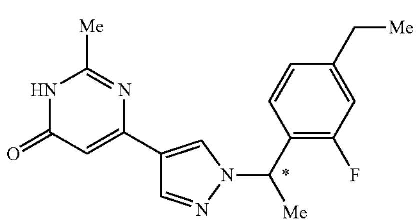 [SMILES: CCc1ccc(C(C)n2cc(-c3cc(=O)[nH]c(C)n3)cn2)c(F)c1] | (R)- or (S)-6-(1-(1-(4-ethyl-2-fluorophenyl)ethyl)-1H-pyrazol-4-yl)-2-methylpyrimidin-4(3H)-one | Calc'd 327.2, found 327.2 | Chiralpak IC | Schemes 17 and 22 |

TABLE 9-continued

| Example No. | Structure | IUPAC Name | Exact Mass [M + H]+ | Chiral column | Methods |
|---|---|---|---|---|---|
| 102 | 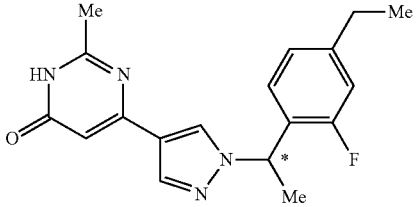 [SMILES: CCc1ccc(C(C)n2cc(-c3cc(=O)[nH]c(C)n3)cn2)c(F)c1] | (S)- or (R)-6-(1-(1-(4-ethyl-2-fluorophenyl)ethyl)-1H-pyrazol-4-yl)-2-methylpyrimidin-4(3H)-one | Calc'd 327.2, found 327.2 | Chiralpak IC | Schemes 17 and 22 |
| 103 | 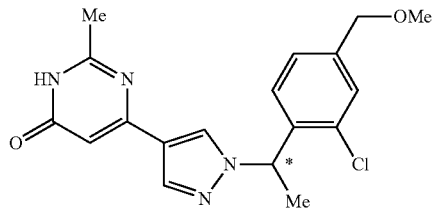 | (R)- or (S)-6-(1-(1-(2-chloro-4-(methoxymethyl)phenyl)ethyl)-1H-pyrazol-4-yl)-2-methylpyrimidin-4(3H)-one | Calc'd 359.1, found 359.2 | Lux3u Cellulose-4 | Schemes 17 and 22 |
| 104 | 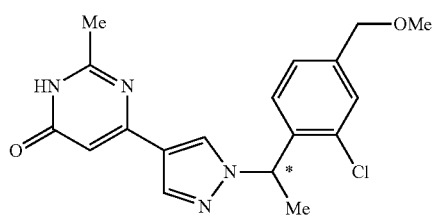 | (S)- or (R)-6-(1-(1-(2-chloro-4-(methoxymethyl)phenyl)ethyl)-1H-pyrazol-4-yl)-2-methylpyrimidin-4(3H)-one | Calc'd 359.1, found 359.2 | Lux3u Cellulose-4 | Schemes 17 and 22 |
| 105 | 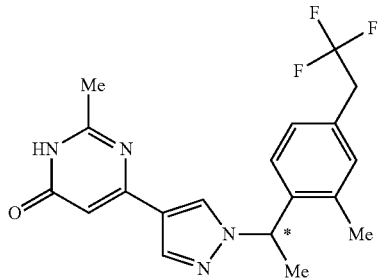 [SMILES: Cc1nc(-c2cnn(C(C)c3ccc(CC(F)(F)F)cc3C)c2)cc(=O)[nH]1] | (R)- or (S)-2-methyl-6-(1-(1-(2-methyl-4-(2,2,2-trifluoroethyl)phenyl)ethyl)-1H-pyrazol-4-yl)pyrimidin-4(3H)-one | Calc'd 377.2, found 377.3 | Chiralpak IC | Schemes 17 and 22 |
| 106 | 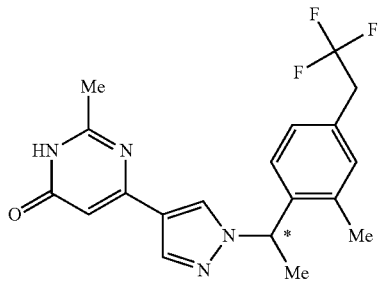 [SMILES: Cc1nc(-c2cnn(C(C)c3ccc(CC(F)(F)F)cc3C)c2)cc(=O)[nH]1] | (S)- or (R)-2-methyl-6-(1-(1-(2-methyl-4-(2,2,2-trifluoroethyl)phenyl)ethyl)-1H-pyrazol-4-yl)pyrimidin-4(3H)-one | Calc'd 377.2, found 377.3 | Chiralpak IC | Schemes 17 and 22 |
| 107 | 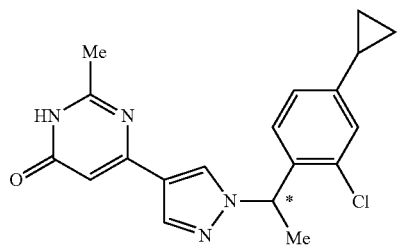 [SMILES: Cc1nc(-c2cnn(C(C)c3ccc(C4CC4)cc3Cl)c2)cc(=O)[nH]1] | (R)- or (S)-6-(1-(1-(2-chloro-4-cyclopropylphenyl)ethyl)-1H-pyrazol-4-yl)-2-methylpyrimidin-4(3H)-one | Calc'd 355.1, found 355.1 | AXIA | Schemes 17 and 22 |

TABLE 9-continued

| Example No. | Structure | IUPAC Name | Exact Mass [M + H]+ | Chiral column | Methods |
|---|---|---|---|---|---|
| 108 | 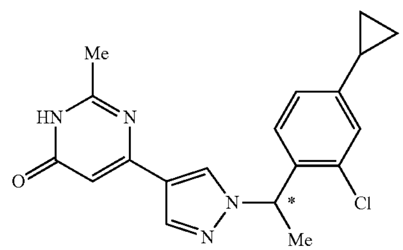 [SMILES: Cc1nc(-c2cnn(C(C)c3ccc(C4CC4)cc3Cl)c2)cc(=O)[nH]1] | (S)- or (R)-6-(1-(1-(2-chloro-4-cyclopropylphenyl)ethyl)-1H-pyrazol-4-yl)-2-methylpyrimidin-4(3H)-one | Calc'd 355.1, found 355.1 | AXIA | Schemes 17 and 22 |
| 109 | 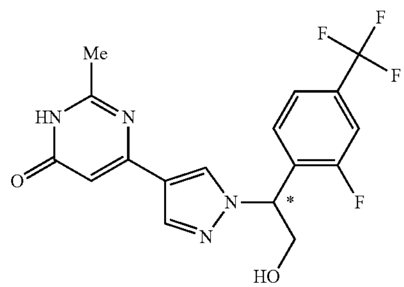 [SMILES: Cc1nc(-c2cnn(C(CO)c3ccc(C(F)(F)F)cc3F)c2)cc(=O)[nH]1] | (R)- or (S)-6-(1-(1-(2-fluoro-4-(trifluoromethyl)phenyl)-2-hydroxyethyl)-1H-pyrazol-4-yl)-2-methylpyrimidin-4(3H)-one | Calc'd 383.1, found 383.0 | Chiralpak IC | Schemes 17, 22, and 28 |
| 110 | 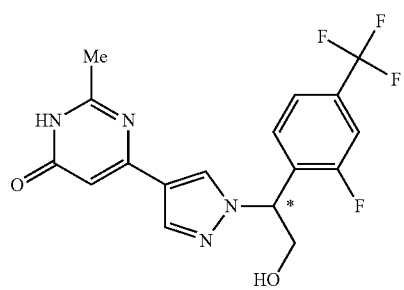 [SMILES: Cc1nc(-c2cnn(C(CO)c3ccc(C(F)(F)F)cc3F)c2)cc(=O)[nH]1] | (S)- or (R)-6-(1-(1-(2-fluoro-4-(trifluoromethyl)phenyl)-2-hydroxyethyl)-1H-pyrazol-4-yl)-2-methylpyrimidin-4(3H)-one | Calc'd 383.1, found 383.0 | Chiralpak IC | Schemes 17, 22, and 28 |
| 111 | 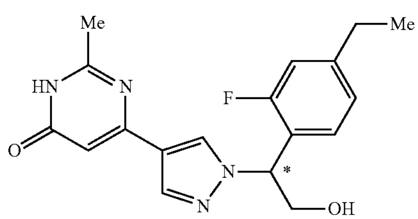 [SMILES: CCc1ccc(C(CO)n2cc(-c3cc(=O)[nH]c(C)n3)cn2)c(F)c1] | (R)- or (S)-6-(1-(1-(4-ethyl-2-fluorophenyl)-2-hydroxyethyl)-1H-pyrazol-4-yl)-2-methylpyrimidin-4(3H)-one | Calc'd 343.2, found 343.0 | Lux Cellulose-4 | Schemes 17, 22, and 28 |
| 112 | 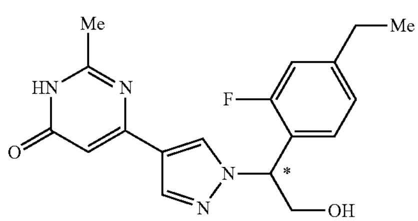 [SMILES: CCc1ccc(C(CO)n2cc(-c3cc(=O)[nH]c(C)n3)cn2)c(F)c1] | (S)- or (R)-6-(1-(1-(4-ethyl-2-fluorophenyl)-2-hydroxyethyl)-1H-pyrazol-4-yl)-2-methylpyrimidin-4(3H)-one | Calc'd 343.2, found 343.0 | Lux Cellulose-4 | Schemes 17, 22, and 28 |
| 113 | 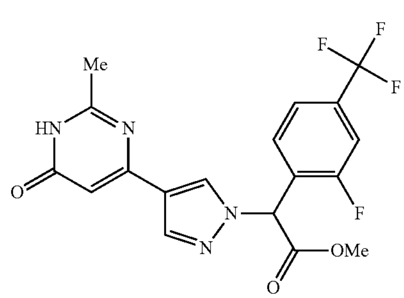 [SMILES: COC(=O)C(c1ccc(C(F)(F)F)cc1F)n1cc(-c2cc(=O)[nH]c(C)n2)cn1] | methyl 2-(2-fluoro-4-(trifluoromethyl)phenyl)-2-(4-(2-methyl-6-oxo-1,6-dihydropyrimidin-4-yl)-1H-pyrazol-1-yl)acetate | Calc'd 411.1, found 411.0 | | Schemes 17 and 22 |

TABLE 9-continued

| Example No. | Structure | IUPAC Name | Exact Mass [M + H]+ | Chiral column | Methods |
|---|---|---|---|---|---|
| 114 | 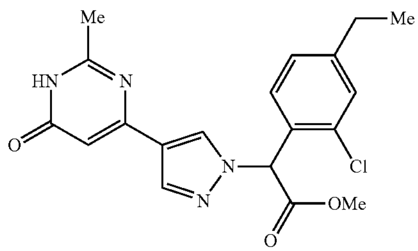 [SMILES: CCc1ccc(C(C(=O)OC)n2cc(-c3cc(=O)[nH]c(C)n3)cn2)c(Cl)c1] | methyl 2-(2-chloro-4-ethylphenyl)-2-(4-(2-methyl-6-oxo-1,6-dihydropyrimidin-4-yl)-1H-pyrazol-1-yl)acetate | Calc'd 387.1, found 387.2 | | Schemes 17 and 22 |
| 115 | 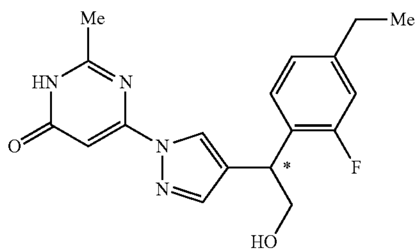 [SMILES: CCc1ccc(C(CO)c2cnn(-c3cc(=O)[nH]c(C)n3)c2)c(F)c1] | (R)- or (S)-6-(4-(1-(4-ethyl-2-fluorophenyl)-2-hydroxyethyl)-1H-pyrazol-1-yl)-2-methylpyrimidin-4(3H)-one | Calc'd 343.2, found 343.1 | Lux Cellulose-4 | Scheme 30 |
| 116 | 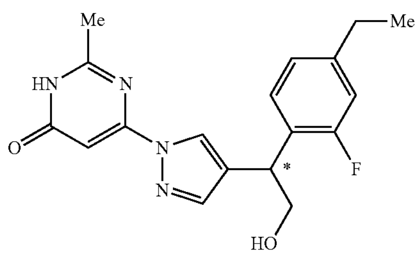 [SMILES: CCc1ccc(C(CO)c2cnn(-c3cc(=O)[nH]c(C)n3)c2)c(F)c1] | (S)- or (R)-6-(4-(1-(4-ethyl-2-fluorophenyl)-2-hydroxyethyl)-1H-pyrazol-1-yl)-2-methylpyrimidin-4(3H)-one | Calc'd 343.2, found 343.1 | Lux Cellulose-4 | Scheme 30 |
| 117 | 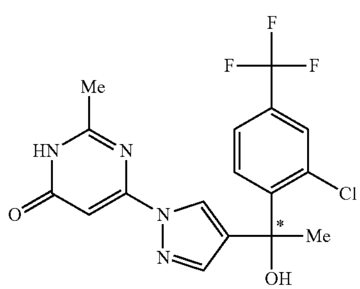 [SMILES: Cc1nc(-n2cc(C(C)(O)c3ccc(C(F)(F)F)cc3Cl)cn2)cc(=O)[nH]1] | (R)- or (S)-6-(4-(1-(2-chloro-4-(trifluoromethyl)phenyl)-1-hydroxyethyl)-1H-pyrazol-1-yl)-2-methylpyrimidin-4(3H)-one | Calc'd 399.1, found 398.9 | Lux Cellulose-4 | Schemes 18 and 25 (PMB deprotection) |
| 118 | 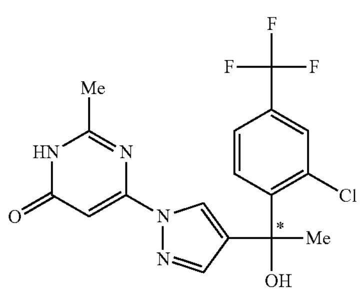 [SMILES: Cc1nc(-n2cc(C(C)(O)c3ccc(C(F)(F)F)cc3Cl)cn2)cc(=O)[nH]1] | (S)- or (R)-6-(4-(1-(2-chloro-4-(trifluoromethyl)phenyl)-1-hydroxyethyl)-1H-pyrazol-1-yl)-2-methylpyrimidin-4(3H)-one | Calc'd 399.1, found 398.9 | Lux Cellulose-4 | Schemes 18 and 25 (PMB deprotection) |

TABLE 9-continued

| Example No. | Structure | IUPAC Name | Exact Mass [M + H]+ | Chiral column | Methods |
|---|---|---|---|---|---|
| 119 | 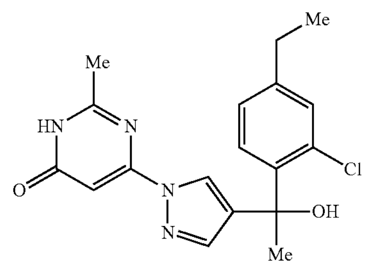 [SMILES: CCc1ccc(C(C)(O)c2cnn(-c3cc(=O)[nH]c(C)n3)c2)c(Cl)c1] | 6-(4-(1-(2-chloro-4-ethylphenyl)-1-hydroxyethyl)-1H-pyrazol-1-yl)-2-methylpyrimidin-4(3H)-one | Calc'd 359.1, found 359.2 | | Schemes 18 and 24 |
| 120 | 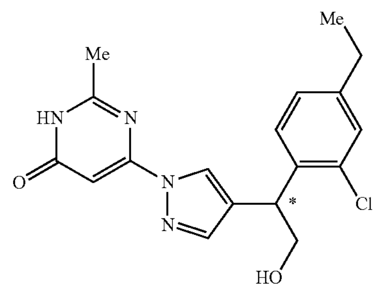 [SMILES: CCc1ccc(C(CO)c2cnn(-c3cc(=O)[nH]c(C)n3)c2)c(Cl)c1] | (R)- or (S)-6-(4-(1-(2-chloro-4-ethylphenyl)-2-hydroxyethyl)-1H-pyrazol-1-yl)-2-methylpyrimidin-4(3H)-one | Calc'd 359.1, found 359.2 | Chiralpak IA | Schemes 18, 24, and 30 |
| 121 | 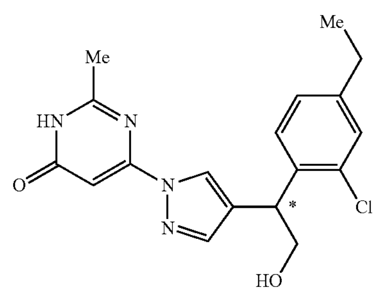 [SMILES: CCc1ccc(C(CO)c2cnn(-c3cc(=O)[nH]c(C)n3)c2)c(Cl)c1] | (S)- or (R)-6-(4-(1-(2-chloro-4-ethylphenyl)-2-hydroxyethyl)-1H-pyrazol-1-yl)-2-methylpyrimidin-4(3H)-one | Calc'd 359.1, found 359.2 | Chiralpak IA | Schemes 18, 24, and 30 |
| 122 | 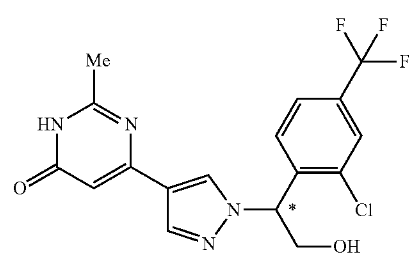 [SMILES: Cc1nc(-c2cnn(C(CO)c3ccc(C(F)(F)F)cc3Cl)c2)cc(=O)[nH]1] | (R)- or (S)-6-(1-(1-(2-chloro-4-(trifluoromethyl)phenyl)-2-hydroxyethyl)-1H-pyrazol-4-yl)-2-methylpyrimidin-4(3H)-one | Calc'd 399.1, found 399.1 | Prepphenyl OBD | Schemes 17, 22, and 28 |
| 123 | 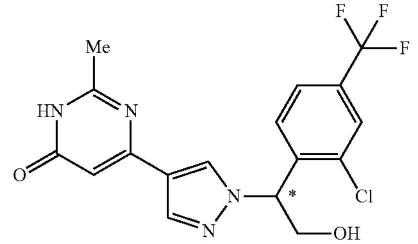 [SMILES: Cc1nc(-c2cnn(C(CO)c3ccc(C(F)(F)F)cc3Cl)c2)cc(=O)[nH]1] | (S)- or (R)-6-(1-(1-(2-chloro-4-(trifluoromethyl)phenyl)-2-hydroxyethyl)-1H-pyrazol-4-yl)-2-methylpyrimidin-4(3H)-one | Calc'd 399.1, found 399.1 | Prepphenyl OBD | Schemes 17, 22, and 28 |

TABLE 9-continued

| Example No. | Structure | IUPAC Name | Exact Mass [M + H]+ | Chiral column | Methods |
|---|---|---|---|---|---|
| 124 | 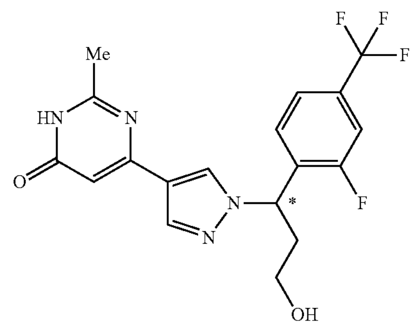 [SMILES: Cc1nc(-c2cnn(C(CCO)c3ccc(C(F)(F)F)cc3F)c2)cc(=O)[nH]1] | (R)- or (S)-6-(4-(1-(2-fluoro-4-(trifluoromethyl)phenyl)-3-hydroxypropyl)-1H-pyrazol-1-yl)-2-methylpyrimidin-4(3H)-one | Calc'd 397.1, found 397.0 | Lux Cellulose-4 | Schemes 3, 6, 24, and 29 |
| 125 | 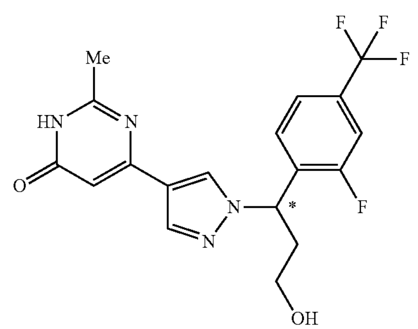 [SMILES: Cc1nc(-c2cnn(C(CCO)c3ccc(C(F)(F)F)cc3F)c2)cc(=O)[nH]1] | (S)- or (R)-6-(4-(1-(2-fluoro-4-(trifluoromethyl)phenyl)-3-hydroxypropyl)-1H-pyrazol-1-yl)-2-methylpyrimidin-4(3H)-one | Calc'd 397.1, found 397.0 | Lux Cellulose-4 | Schemes 3, 6, 24, and 29 |
| 126 | 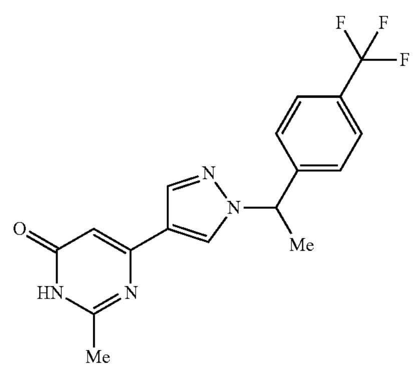 [SMILES: Cc1nc(-c2cnn(C(C)c3ccc(C(F)(F)F)cc3)c2)cc(=O)[nH]1] | 2-methyl-6-(1-(1-(4-(trifluoromethyl)phenyl)ethyl)-1H-pyrazol-4-yl)pyrimidin-4(3H)-one | Calc'd 349.1, found 349.1 | | Scheme 35 |
| 127 | 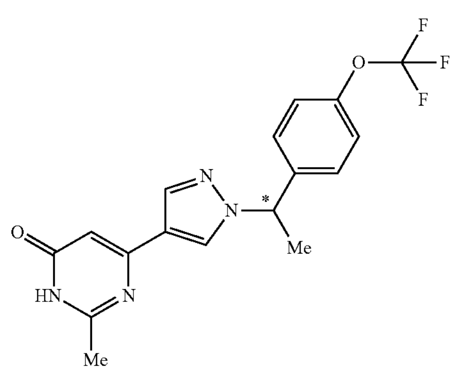 [SMILES: Cc1nc(-c2cnn(C(C)c3ccc(OC(F)(F)F)cc3)c2)cc(=O)[nH]1] | (R)- or (S)-2-methyl-6-(1-(1-(4-(trifluoromethoxy)phenyl)ethyl)-1H-pyrazol-4-yl)pyrimidin-4(3H)-one | Calc'd 365.1, found 365.0 | Chiralpak AD | Scheme 35 |

TABLE 9-continued

| Example No. | Structure | IUPAC Name | Exact Mass [M + H]+ | Chiral column | Methods |
|---|---|---|---|---|---|
| 128 | 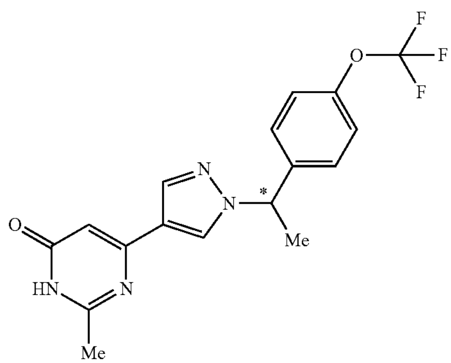 [SMILES: Cc1nc(-c2cnn(C(C)c3ccc(OC(F)(F)F)cc3)c2)cc(=O)[nH]1] | (S)- or (R)-2-methyl-6-(1-(1-(4-(trifluoromethoxy)phenyl)ethyl)-1H-pyrazol-4-yl)pyrimidin-4(3H)-one | Calc'd 365.1, found 365.0 | Chiralpak AD | Scheme 35 |
| 129 | 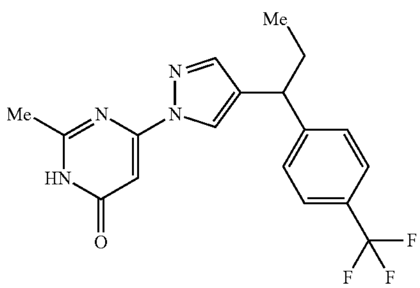 [SMILES: CCC(c1ccc(C(F)(F)F)cc1)c1cnn(-c2cc(=O)[nH]c(C)n2)c1] | 2-methyl-6-(4-(1-(4-(trifluoromethyl)phenyl)propyl)-1H-pyrazol-1-yl)pyrimidin-4(3H)-one | Calc'd 363.1, found 363.1 | | Scheme 20 |
| 130 | 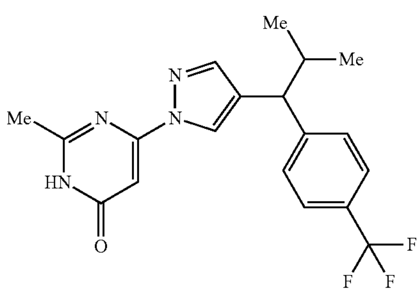 [SMILES: Cc1nc(-n2cc(C(c3ccc(C(F)(F)F)cc3)C(C)C)cn2)cc(=O)[nH]1] | 2-methyl-6-(4-(2-methyl-1-(4-phenyl)propyl)-1H-pyrazol-1-yl)pyrimidin-4(3H)-one | Calc'd 377.2, found 377.1 | | Scheme 20 |
| 131 | 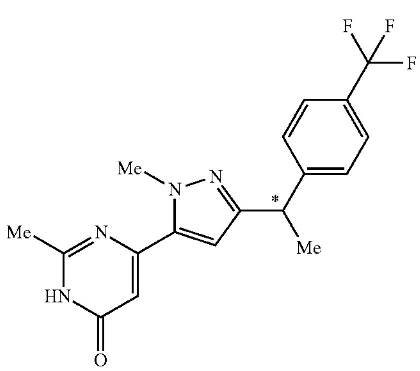 [SMILES: Cc1nc(-c2cc(C(C)c3ccc(C(F)(F)F)cc3)nn2C)cc(=O)[nH]1] | (R)- or (S)-2-methyl-6-(1-methyl-3-(1-(4-(trifluoromethyl)phenyl)ethyl)-1H-pyrazol-5-yl)pyrimidin-4(3H)-one | Calc'd 363.1, found 363.1 | Chiralpak AD | Scheme 32 |

TABLE 9-continued

| Example No. | Structure | IUPAC Name | Exact Mass [M + H]+ | Chiral column | Methods |
|---|---|---|---|---|---|
| 132 | 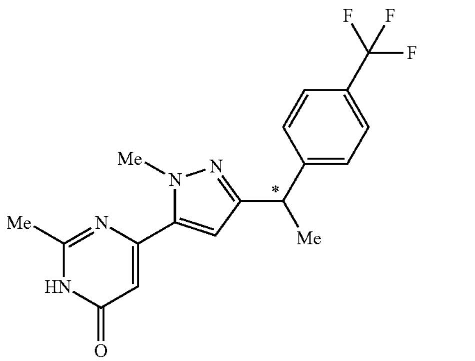 [SMILES: Cc1nc(-c2cc(C(C)c3ccc(C(F)(F)F)cc3)nn2C)cc(=O)[nH]1] | (S)- or (R)-2-methyl-6-(1-methyl-3-(1-(4-(trifluoromethyl)phenyl)ethyl)-1H-pyrazol-5-yl)pyrimidin-4(3H)-one | Calc'd 363.1, found 363.1 | Chiralpak AD | Scheme 32 |
| 133 | 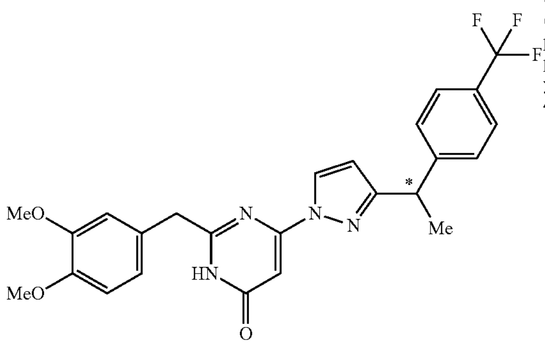 | (R)- or (S)-2-(3,4-dimethoxybenzyl)-6-(3-(1-(4-(trifluoromethyl)phenyl)ethyl)-1H-pyrazol-1-yl)pyrimidin-4(3H)-one | Calc'd 485.2, found 485.0 | Chiralpak AS | Scheme 21 |
| 134 | 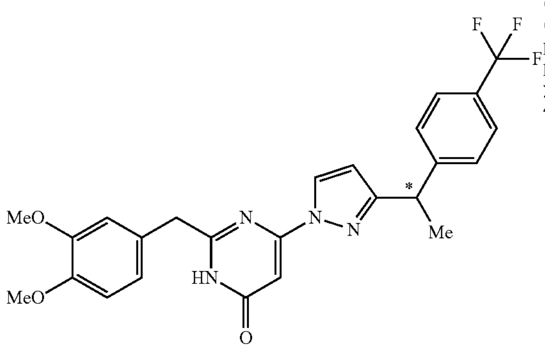 | (R)- or (S)-2-(3,4-dimethoxybenzyl)-6-(3-(1-(4-(trifluoromethyl)phenyl)ethyl)-1H-pyrazol-1-yl)pyrimidin-4(3H)-one | Calc'd 485.2, found 485.0 | Chiralpak AS | Scheme 21 |
| 135 | 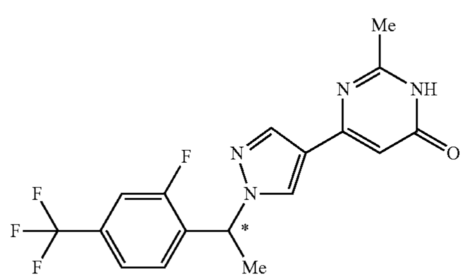 [SMILES: Cc1nc(-c2cnn(C(C)c3ccc(C(F)(F)F)cc3F)c2)cc(=O)[nH]1] | (R)- or (S)-6-(1-(1-(2-fluoro-4-(trifluoromethyl)phenyl)ethyl)-1H-pyrazol-4-yl)-2-methylpyrimidin-4(3H)-one | Calc'd 367.1, found 367.0 | Chiralpak IC | Scheme 19 |

TABLE 9-continued

| Example No. | Structure | IUPAC Name | Exact Mass [M + H]+ | Chiral column | Methods |
|---|---|---|---|---|---|
| 136 | 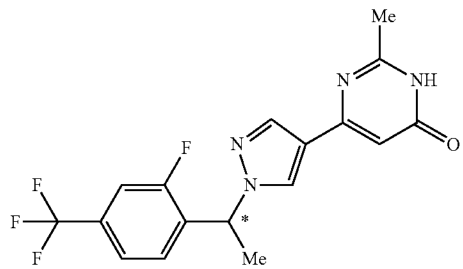 [SMILES: Cc1nc(-c2cnn(C(C)c3ccc(C(F)(F)F)cc3F)c2)cc(=O)[nH]1] | (S)- or (R)-6-(1-(1-(2-fluoro-4-(trifluoromethyl)phenyl)ethyl)-1H-pyrazol-4-yl)-2-methylpyrimidin-4(3H)-one | Calc'd 367.1, found 366.9 | Chiralpak IC | Scheme 19 |
| 137 | 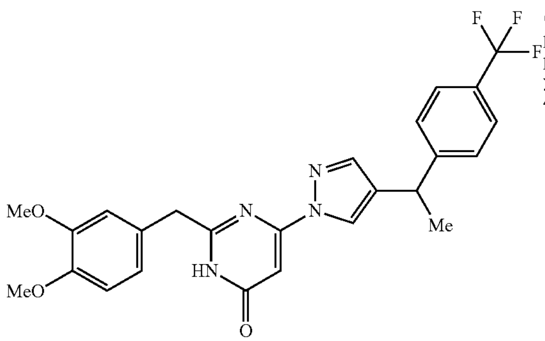 [SMILES: COc1ccc(Cc2nc(-n3cc(C(C)c4ccc(C(F)(F)F)cc4)cn3)cc(=O)[nH]2)cc1OC] | 2-(3,4-dimethoxybenzyl)-6-(4-(1-(4-(trifluoromethyl)phenyl)ethyl)-1H-pyrazol-1-yl)pyrimidin-4(3H)-one | Calc'd 485.2, found 485.1 | | Scheme 21 |
| 138 | 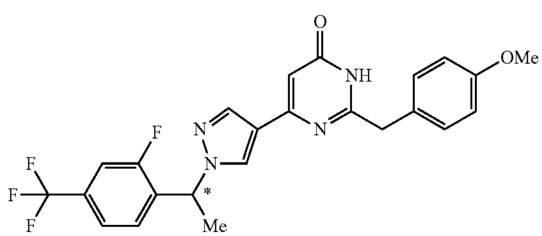 [SMILES: COc1ccc(Cc2nc(-c3cnn(C(C)c4ccc(C(F)(F)F)cc4F)c3)cc(=O)[nH]2)cc1] | (R)- or (S)-6-(1-(1-(2-fluoro-4-(trifluoromethyl)phenyl)ethyl)-1H-pyrazol-4-yl)-2-(4-methoxybenzyl)pyrimidin-4(3H)-one | Calc'd 473.2, found 473.0 | Lux Cellulose-4 | Scheme 19 |
| 139 | 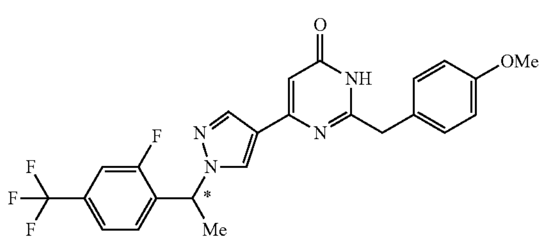 [SMILES: COc1ccc(Cc2nc(-c3cnn(C(C)c4ccc(C(F)(F)F)cc4F)c3)cc(=O)[nH]2)cc1] | (S)- or (R)-6-(1-(1-(2-fluoro-4-(trifluoromethyl)phenyl)ethyl)-1H-pyrazol-4-yl)-2-(4-methoxybenzyl)pyrimidin-4(3H)-one | Calc'd 473.2, found 473.0 | Lux Cellulose-4 | Scheme 19 |
| 140 | 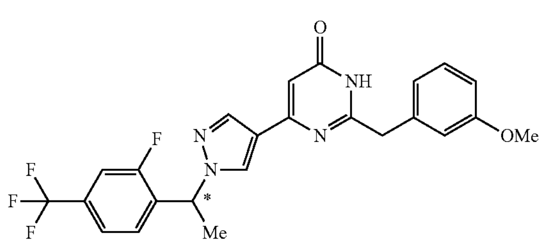 [SMILES: COc1cccc(Cc2nc(-c3cnn(C(C)c4ccc(C(F)(F)F)cc4F)c3)cc(=O)[nH]2)c1] | (R)- or (S)-6-(1-(1-(2-fluoro-4-(trifluoromethyl)phenyl)ethyl)-1H-pyrazol-4-yl)-2-(3-methoxybenzyl)pyrimidin-4(3H)-one | Calc'd 473.2, found 473.0 | Lux Cellulose-4 | Scheme 19 |

TABLE 9-continued

| Example No. | Structure | IUPAC Name | Exact Mass [M + H]+ | Chiral column | Methods |
|---|---|---|---|---|---|
| 141 | 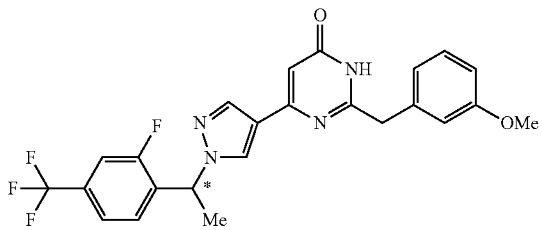 [SMILES: COc1cccc(Cc2nc(-c3cnn(C(C)c4ccc(C(F)(F)F)cc4F)c3)cc(=O)[nH]2)c1] | (S)- or (R)-6-(1-(1-(2-fluoro-4-(trifluoromethyl)phenyl)ethyl)-1H-pyrazol-4-yl)-2-(3-methoxybenzyl)pyrimidin-4(3H)-one | Calc'd 473.2, found 473.0 | Lux Cellulose-4 | Scheme 19 |
| 142 | 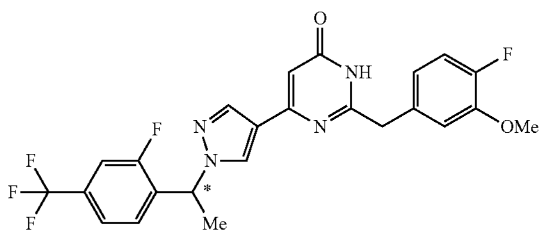 [SMILES: COc1cc(Cc2nc(-c3cnn(C(C)c4ccc(C(F)(F)F)cc4F)c3)cc(=O)[nH]2)ccc1F] | (R)- or (S)-2-(4-fluoro-3-methoxybenzyl)-6-(1-(1-(2-fluoro-4-(trifluoromethyl)phenyl)ethyl)-1H-pyrazol-4-yl)pyrimidin-4(3H)-one | Calc'd 491.2, found 491.0 | Lux Cellulose-4 | Scheme 19 |
| 143 | 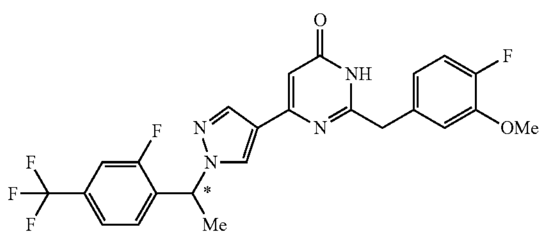 [SMILES: COc1cc(Cc2nc(-c3cnn(C(C)c4ccc(C(F)(F)F)cc4F)c3)cc(=O)[nH]2)ccc1F] | (S)- or (R)-2-(4-fluoro-3-methoxybenzyl)-6-(1-(1-(2-fluoro-4-(trifluoromethyl)phenyl)ethyl)-1H-pyrazol-4-yl)pyrimidin-4(3H)-one | Calc'd 491.2, found 491.0 | Lux Cellulose-4 | Scheme 19 |
| 144 | 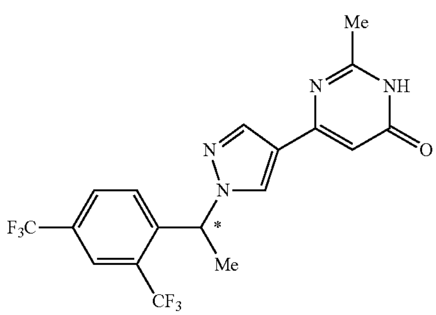 [SMILES: Cc1nc(-c2cnn(C(C)c3ccc(C(F)(F)F)cc3C(F)(F)F)c2)cc(=O)[nH]1] | (R)- or (S)-6-(1-(1-(2,4-bis(trifluoromethyl)phenyl)ethyl)-1H-pyrazol-4-yl)-2-methylpyrimidin-4(3H)-one | Calc'd 417.1, found 416.9 | Chiralpak AD-H | Scheme 19 |
| 145 | 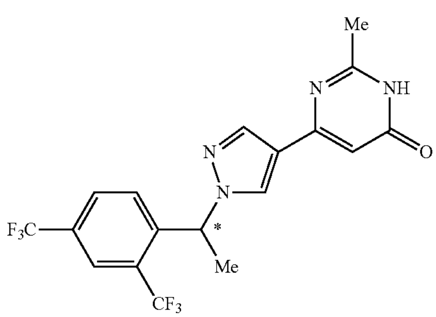 [SMILES: Cc1nc(-c2cnn(C(C)c3ccc(C(F)(F)F)cc3C(F)(F)F)c2)cc(=O)[nH]1] | (S)- or (R)-6-(1-(1-(2,4-bis(trifluoromethyl)phenyl)ethyl)-1H-pyrazol-4-yl)-2-methylpyrimidin-4(3H)-one | Calc'd 417.1, found 416.9 | Chiralpak AD-H | Scheme 19 |

TABLE 9-continued

| Example No. | Structure | IUPAC Name | Exact Mass [M + H]+ | Chiral column | Methods |
|---|---|---|---|---|---|
| 146 | 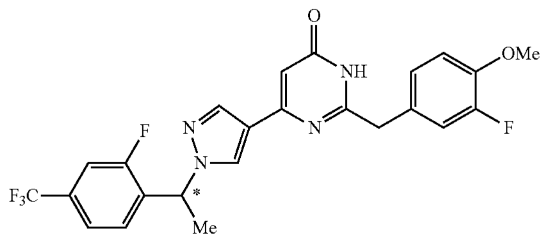 [SMILES: COc1ccc(Cc2nc(-c3cnn(C(C)c4ccc(C(F)(F)F)cc4F)c3)cc(=O)[nH]2)cc1F] | (R)- or (S)-6-(1-(1-(2-fluoro-4-(trifluoromethyl)phenyl)ethyl)-1H-pyrazol-4-yl)-2-(3-fluoro-4-methoxybenzyl)pyrimidin-4(3H)-one | Calc'd 491.2, found 490.9 | Chiralpak OJ-H | Scheme 19 |
| 147 | 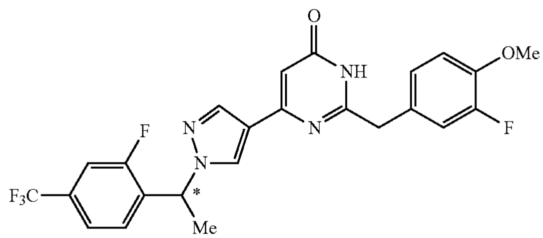 [SMILES: COc1ccc(Cc2nc(-c3cnn(C(C)c4ccc(C(F)(F)F)cc4F)c3)cc(=O)[nH]2)cc1F] | (S)- or (R)-6-(1-(1-(2-fluoro-4-(trifluoromethyl)phenyl)ethyl)-1H-pyrazol-4-yl)-2-(3-fluoro-4-methoxybenzyl)pyrimidin-4(3H)-one | Calc'd 491.2, found 490.9 | Chiralpak OJ-H | Scheme 19 |
| 148 | 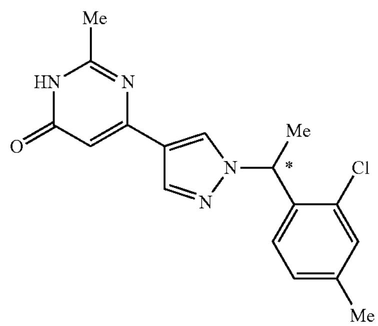 [SMILES: Cc1ccc(C(C)n2cc(-c3cc(=O)[nH]c(C)n3)cn2)c(Cl)c1] | (R)- or (S)-6-(1-(1-(2-chloro-4-methylphenyl)ethyl)-1H-pyrazol-4-yl)-2-methylpyrimidin-4(3H)-one | Calc'd 329.1, found 329.1 | Lux Cellulose-4 | Scheme 19 |
| 149 | 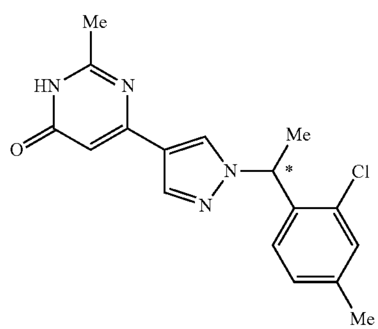 [SMILES: Cc1ccc(C(C)n2cc(-c3cc(=O)[nH]c(C)n3)cn2)c(Cl)c1] | (S)- or (R)-6-(1-(1-(2-chloro-4-methylphenyl)ethyl)-1H-pyrazol-4-yl)-2-methylpyrimidin-4(3H)-one | Calc'd 329.1, found 329.1 | Lux Cellulose-4 | Scheme 19 |
| 150 | 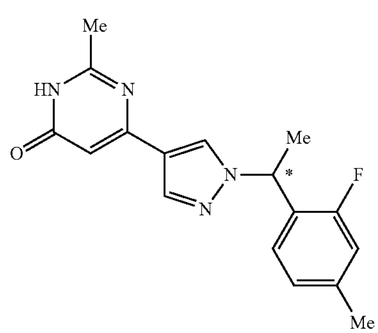 [SMILES: Cc1ccc(C(C)n2cc(-c3cc(=O)[nH]c(C)n3)cn2)c(F)c1] | (R)- or (S)-6-(1-(1-(2-fluoro-4-methylphenyl)ethyl)-1H-pyrazol-4-yl)-2-methylpyrimidin-4(3H)-one | Calc'd 313.1, found 313.1 | Chiralpak AD | Scheme 19 |

TABLE 9-continued

| Example No. | Structure | IUPAC Name | Exact Mass [M + H]+ | Chiral column | Methods |
|---|---|---|---|---|---|
| 151 | 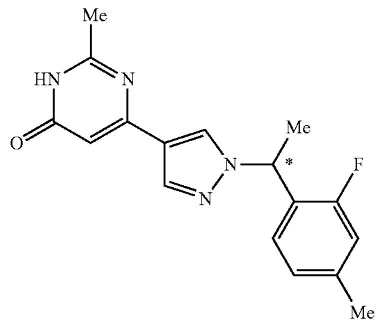 [SMILES: Cc1ccc(C(C)n2cc(-c3cc(=O)[nH]c(C)n3)cn2)c(F)c1] | (S)- or (R)-6-(1-(1-(2-fluoro-4-methylphenyl)ethyl)-1H-pyrazol-4-yl)-2-methylpyrimidin-4(3H)-one | Calc'd 313.1, found 313.1 | Chiralpak AD | Scheme 19 |
| 152 | 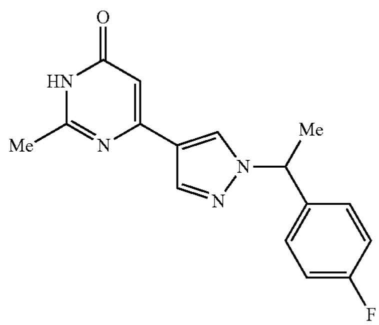 [SMILES: Cc1nc(-c2cnn(C(C)c3ccc(F)cc3)c2)cc(=O)[nH]1] | 6-(1-(1-(4-fluorophenyl)ethyl)-1H-pyrazol-4-yl)-2-methylpyrimidin-4(3H)-one | Calc'd 299.1, found 299.2 | | Scheme 19 |
| 153 | 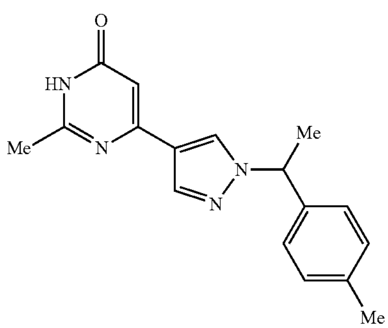 [SMILES: Cc1ccc(C(C)n2cc(-c3cc(=O)[nH]c(C)n3)cn2)cc1] | 2-methyl-6-(1-(1-(p-tolyl)ethyl)-1H-pyrazol-4-yl)pyrimidin-4(3H)-one | Calc'd 295.2 found 295.1 | | Scheme 19 |
| 154 | 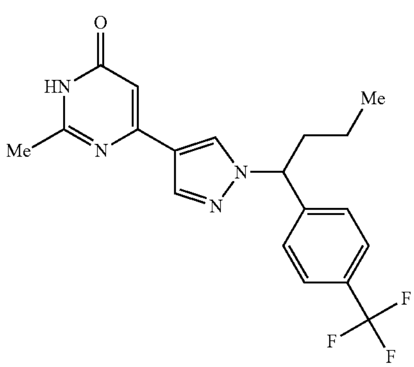 [SMILES: CCCC(c1ccc(C(F)(F)F)cc1)n1cc(-c2cc(=O)[nH]c(C)n2)cn1] | 2-methyl-6-(1-(1-(4-(trifluoromethyl)phenyl)butyl)-1H-pyrazol-4-yl)pyrimidin-4(3H)-one | Calc'd 377.2, found 377.3 | | Scheme 19 |

TABLE 9-continued

| Example No. | Structure | IUPAC Name | Exact Mass [M + H]+ | Chiral column | Methods |
|---|---|---|---|---|---|
| 155 | 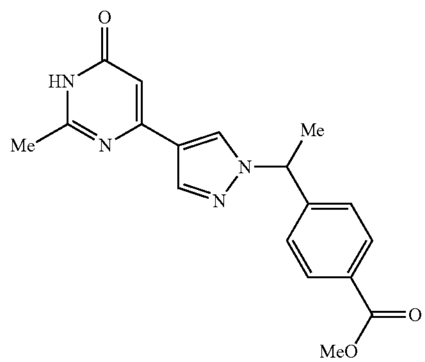 [SMILES: COC(=O)c1ccc(C(C)n2cc(-c3cc(=O)[nH]c(C)n3)cn2)cc1] | methyl 4-(1-(4-(2-methyl-6-oxo-1,6-dihydropyrimidin-4-yl)-1H-pyrazol-1-yl)ethyl)benzoate | Calc'd 339.1, found 339.1 | | Scheme 19 |
| 156 | 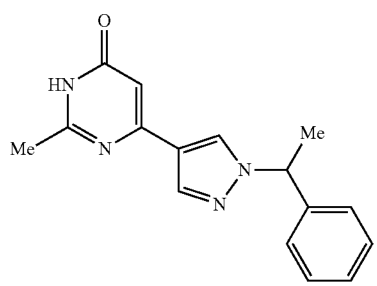 [SMILES: Cc1nc(-c2cnn(C(C)c3ccccc3)c2)cc(=O)[nH]1] | 2-methyl-6-(1-(1-phenylethyl)-1H-pyrazol-4-yl)pyrimidin-4(3H)-one | Calc'd 281.1, found 281.2 | | Scheme 19 |
| 157 | 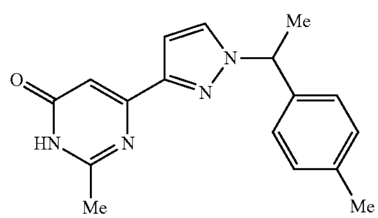 [SMILES: Cc1ccc(C(C)n2ccc(-c3cc(=O)[nH]c(C)n3)n2)cc1] | 2-methyl-6-(1-(1-(p-tolyl)ethyl)-1H-pyrazol-3-yl)pyrimidin-4(3H)-one | Calc'd 295.2, found 295.2 | | Scheme 19 |
| 158 | 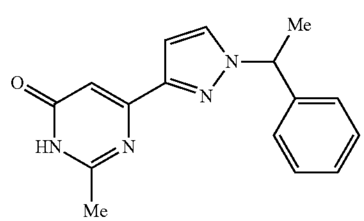 [SMILES: Cc1nc(-c2ccn(C(C)c3ccccc3)n2)cc(=O)[nH]1] | 2-methyl-6-(1-(1-phenylethyl)-1H-pyrazol-3-yl)pyrimidin-4(3H)-one | Calc'd 281.1, found 281.1 | | Scheme 19 |
| 159 | 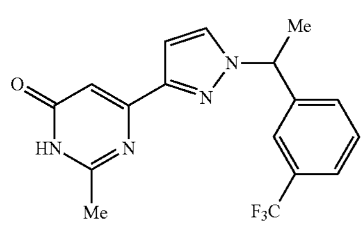 [SMILES: Cc1nc(-c2ccn(C(C)c3cccc(C(F)(F)F)c3)n2)cc(=O)[nH]1] | 2-methyl-6-(1-(1-(3-(trifluoromethyl)phenyl)ethyl)-1H-pyrazol-3-yl)pyrimidin-4(3H)-one | Calc'd 349.1, found 349.2 | | Scheme 19 |

TABLE 9-continued

| Example No. | Structure | IUPAC Name | Exact Mass [M + H]+ | Chiral column | Methods |
|---|---|---|---|---|---|
| 160 | 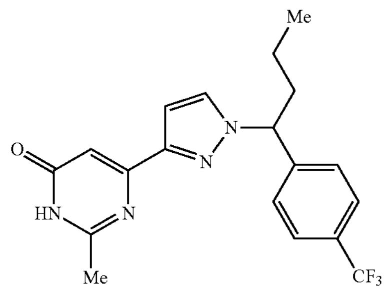 [SMILES: CCCC(c1ccc(C(F)(F)F)cc1)n1ccc(-c2cc(=O)[nH]c(C)n2)n1] | 2-methyl-6-(1-(1-(4-(trifluoromethyl)phenyl)butyl)-1H-pyrazol-3-yl)pyrimidin-4(3H)-one | Calc'd 377.2, found 377.2 | | Scheme 19 |
| 161 | 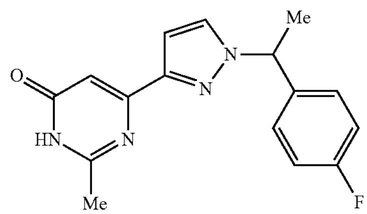 [SMILES: Cc1nc(-c2ccn(C(C)c3ccc(F)cc3)n2)cc(=O)[nH]1] | 6-(1-(1-(4-fluorophenyl)ethyl)-1H-pyrazol-3-yl)-2-methylpyrimidin-4(3H)-one | Calc'd 299.1, found 299.2 | | Scheme 19 |
| 162 | 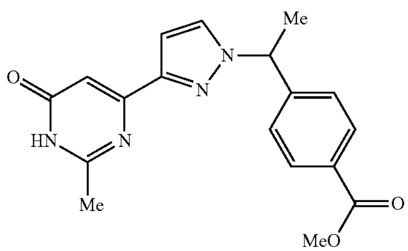 [SMILES: COC(=O)c1ccc(C(C)n2ccc(-c3cc(=O)[nH]c(C)n3)n2)cc1] | methyl 4-(1-(3-(2-methyl-6-oxo-1,6-dihydropyrimidin-4-yl)-1H-pyrazol-1-yl)ethyl)benzoate | Calc'd 339.1, found 339.1 | | Scheme 19 |

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 10 μM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki—~0.2 nM) at 1 μM concentration for 100% inhibition. Bay 60-7550 was obtained from Axxora via Fisher Scientific (cat# ALX-270-421-M025/cat# NC9314773). Put another way, any compound with Ki of ~0.2 to about 2 nM could be used at 1 to 10 μM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM $MgCl_2$, 0.05% $NaN_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µl, of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization $(mP) = 1000*(S/So-P/Po)/(S/So+P/Po)$.

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \ mP - 100\% \ mP)(Imax - Imin)}{1 + \left[\frac{[Drug]}{\left(10^{-pk_I}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme.

TABLE 10

PDE2 Ki's

| Example No. | Rhesus PDE2 Ki (nM) Lab A | Human PDE2 Ki (nM) Lab A | Human PDE2 Ki (nM) Lab B | Rhesus PDE2 Ki (nM) Lab B |
|---|---|---|---|---|
| 1 | ND | ND | ND | 300.5 |
| 2 | 43.9 | 41.5 | 17.1 | 35.3 |
| 3 | ND | ND | 40.3 | 93.0 |
| 4 | ND | 18.2 | 14.4 | 29.5 |
| 5 | ND | ND | 173.6 | 285.1 |
| 6 | ND | ND | 241.4 | 465.6 |
| 7 | ND | 126.5 | ND | ND |
| 8 | ND | 106.9 | ND | ND |
| 9 | 58.8 | 104 | ND | 30.7 |
| 10 | 25.0 | 19.5 | ND | ND |
| 11 | ND | 42.5 | ND | ND |
| 12 | ND | 244.4 | ND | ND |
| 13 | ND | 287.3 | ND | ND |
| 14 | ND | 1400 | ND | ND |
| 15 | ND | ND | 11.7 | 15.6 |
| 16 | ND | ND | 47.1 | 75.8 |
| 17 | ND | 682.7 | ND | ND |
| 18 | ND | 10.7 | ND | ND |
| 19 | ND | ND | 85.0 | 104.8 |
| 20 | ND | 32.3 | 16.8 | 18.2 |
| 21 | ND | ND | 199 | 213.3 |
| 22 | ND | ND | 31.5 | 41.9 |
| 23 | ND | ND | 19.4 | 29.3 |
| 24 | ND | ND | 81.0 | 153.7 |
| 25 | ND | ND | ND | 3681 |
| 26 | ND | ND | ND | 1145 |
| 27 | ND | ND | 66.6 | 98.0 |
| 28 | ND | ND | 72.0 | 94.5 |
| 29 | ND | ND | 829.2 | 1207 |
| 30 | ND | ND | 1108 | 2944 |
| 31 | ND | ND | ND | 487.7 |
| 32 | 19310 | ND | ND | 49260 |
| 33 | 36.6 | 32.0 | ND | 19.7 |
| 34 | 54.6 | 44.6 | ND | 26.9 |
| 35 | 38.3 | 60.4 | ND | 17.3 |
| 36 | 25.7 | 17.2 | ND | ND |
| 37 | 13.1 | 7.9 | ND | ND |
| 38 | ND | ND | ND | 302.6 |
| 39 | ND | ND | 35.3 | 99.9 |
| 40 | ND | ND | 197 | 211.2 |
| 41 | ND | ND | ND | 7297 |
| 42 | ND | ND | ND | 2620 |
| 43 | ND | ND | ND | 313.3 |
| 44 | ND | ND | ND | ND |
| 45 | ND | ND | ND | 411.5 |
| 46 | ND | ND | ND | 2484 |
| 47 | ND | ND | ND | 1235 |
| 48 | ND | ND | 218.7 | 333.3 |
| 49 | ND | ND | ND | ND |
| 50 | ND | ND | ND | >1000 |
| 51 | ND | ND | ND | >1000 |
| 52 | ND | 12.3 | 4.9 | 7.2 |
| 53 | ND | ND | 33.2 | 64.5 |
| 54 | ND | ND | ND | 18230 |
| 55 | ND | ND | ND | 466.5 |
| 56 | ND | ND | ND | 314.4 |
| 57 | 13.1 | 16.4 | 6.8 | 13.0 |
| 58 | ND | ND | ND | 256 |
| 59 | ND | ND | ND | 469.1 |
| 60 | 3.6 | 3.7 | 1.1 | 2.4 |
| 61 | 2.0 | 2.4 | 0.9 | 1.8 |
| 62 | ND | ND | 86.5 | 142.6 |
| 63 | ND | ND | 46.5 | 99.3 |
| 64 | 7.2 | 7.2 | 3.3 | 3.5 |
| 65 | 22.0 | 22.0 | 8.5 | 9.9 |
| 66 | ND | ND | 0.5 | 0.8 |
| 67 | 0.2 | 0.2 | 0.1 | 0.1 |
| 68 | 30070 | ND | ND | 40140 |
| 69 | ND | 32.6 | ND | ND |
| 70 | ND | 311.5 | ND | ND |
| 71 | ND | 16.5 | ND | ND |
| 72 | ND | 412.4 | ND | ND |
| 73 | ND | ND | ND | 6375 |
| 74 | ND | ND | ND | 10970 |
| 75 | ND | ND | ND | 3248 |
| 76 | ND | ND | ND | 15870 |
| 77 | ND | ND | 441.4 | 542.1 |
| 78 | ND | ND | 255.4 | 318.4 |
| 79 | ND | ND | ND | 727.4 |
| 80 | ND | ND | 140.5 | 194.2 |
| 81 | ND | ND | 194.1 | 232.4 |
| 82 | ND | ND | 184.4 | 191.8 |
| 83 | 6.2 | 5.1 | ND | ND |
| 84 | 179 | ND | ND | ND |
| 85 | 14.4 | 10.4 | ND | ND |
| 86 | 145.5 | ND | ND | ND |
| 87 | 480 | ND | ND | ND |
| 88 | 161.8 | ND | ND | ND |
| 89 | 1844 | ND | ND | ND |
| 90 | 149.9 | ND | ND | ND |
| 91 | 60.0 | 48.4 | ND | ND |
| 92 | 212.3 | ND | ND | ND |
| 93 | 706.4 | ND | ND | ND |
| 94 | 40.8 | 52.5 | ND | ND |
| 95 | 1143 | ND | ND | ND |
| 96 | 1259 | ND | ND | ND |
| 97 | 464.5 | ND | ND | ND |
| 98 | >2970 | ND | ND | ND |
| 99 | 10.7 | 10.4 | ND | ND |
| 100 | 383.9 | ND | ND | ND |
| 101 | 25.4 | 38.5 | ND | ND |
| 102 | 211.6 | ND | ND | ND |
| 103 | 106.5 | ND | ND | ND |
| 104 | >2970 | ND | ND | ND |
| 105 | ND | >2955 | ND | ND |
| 106 | ND | 709.7 | ND | ND |
| 107 | ND | 9.4 | ND | ND |
| 108 | ND | 357.9 | ND | ND |
| 109 | ND | 27.5 | ND | ND |
| 110 | ND | 299.4 | ND | ND |
| 111 | ND | 42.5 | ND | ND |
| 112 | ND | 438.3 | ND | ND |
| 113 | ND | 1970 | ND | ND |
| 114 | ND | 1823 | ND | ND |
| 115 | ND | 163 | ND | ND |
| 116 | ND | 537.5 | ND | ND |
| 117 | ND | 4.4 | ND | ND |
| 118 | ND | 47.8 | ND | ND |
| 119 | ND | 16.7 | ND | ND |
| 120 | ND | 321 | ND | ND |
| 121 | ND | 8.4 | ND | ND |
| 122 | ND | 615.8 | ND | ND |
| 123 | ND | 6.5 | ND | ND |
| 124 | ND | 11.9 | ND | ND |
| 125 | ND | 40.4 | ND | ND |
| 126 | ND | ND | 232.6 | 306.1 |
| 127 | ND | ND | 102.8 | 129.5 |
| 128 | ND | ND | ND | 588 |
| 129 | ND | ND | 141.5 | 183.7 |
| 130 | ND | ND | 87.6 | 138 |
| 131 | ND | ND | ND | >1000 |
| 132 | ND | ND | ND | >1000 |
| 133 | ND | ND | 38.5 | 64.8 |
| 134 | ND | ND | 66.6 | 110 |
| 135 | ND | ND | 91.9 | 109.4 |
| 136 | 18.3 | 19.1 | 7.6 | 11.1 |
| 137 | 1.3 | 1.0 | 0.4 | 0.6 |
| 138 | 5.6 | 7.1 | 5.1 | 1.6 |
| 139 | 52.1 | 41.6 | 24.5 | 19.1 |
| 140 | 3.0 | 2.6 | ND | 0.8 |
| 141 | 25.6 | 17.3 | ND | 8.7 |
| 142 | 3.3 | 3.5 | ND | 1.4 |

TABLE 10-continued

| | PDE2 Ki's | | | |
|---|---|---|---|---|
| Example No. | Rhesus PDE2 Ki (nM) Lab A | Human PDE2 Ki (nM) Lab A | Human PDE2 Ki (nM) Lab B | Rhesus PDE2 Ki (nM) Lab B |
| 143 | 21.3 | 27.9 | ND | 10.9 |
| 144 | 396.7 | ND | ND | ND |
| 145 | 6809 | ND | ND | ND |
| 146 | 31.5 | 31.2 | ND | ND |
| 147 | 3.6 | 3.3 | ND | ND |
| 148 | 47.9 | 61.0 | ND | ND |
| 149 | 953.6 | ND | ND | ND |
| 150 | 695 | ND | ND | ND |
| 151 | 218.5 | ND | ND | ND |
| 152 | ND | ND | ND | 4131 |
| 153 | ND | 1244 | ND | 824.7 |
| 154 | ND | ND | 264.9 | 244.5 |
| 155 | ND | ND | ND | 3830 |
| 156 | ND | ND | ND | 4888 |
| 157 | ND | ND | ND | 48710 |
| 158 | ND | ND | ND | 18450 |
| 159 | ND | ND | ND | 25680 |
| 160 | ND | ND | ND | 2298 |
| 161 | ND | ND | ND | 13920 |
| 162 | ND | ND | ND | 29840 |

(ND = Not determined)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound represented by structural formula I:

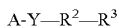

A-Y—R²—R³     I or a pharmaceutically acceptable salt or solvate thereof, wherein:
A is a pyrimidinone optionally substituted with 1 to 2 groups of R¹;
Y is pyrazolyl optionally substituted with 1 to 2 groups of R$^b$;
R¹ is selected from the group consisting of hydrogen, $C_{1-6}$alkyl, $C_{3-10}$cycloalkyl, and $(CH_2)_nC_{6-10}$aryl, said alkyl and aryl optionally substituted with one to three groups of R$^a$;
R² is selected from the group consisting of —C(=O)—, and CR$^X$R$^Y$;
R$^X$ and R$^Y$ are independently selected from the group consisting of H, $(CH_2)_n$OR, $C_{1-6}$alkyl, C(O)OR and $N(R)_2$, said alkyl optionally substituted with one to three groups of R$^a$;
or R$^X$ and R$^Y$ can combine with the carbon atom to which they are attached to form a group selected from —O—, $C_{2-6}$ alkenyl, $C_{3-6}$ cycloalkyl and $C_{3-6}$ heterocyclyl;
R represents H, or $C_{1-6}$alkyl,
R³ is $C_{4-10}$heterocyclyl or $C_{6-10}$ aryl, said heterocyclyl and aryl optionally substituted with one to three groups of R$^a$;
or R² and R³ can combine to form a $C_{3-10}$ heterocyclyl, said heterocyclyl optionally substituted with one to three groups of R$^a$;
R$^a$ is selected from the group consisting of H, halo, CN, $C_{1-6}$alkyl, $(CH_2)_n$OR, (O)p $C_{1-4}$haloalkyl, C(O)OR, —O$(CH_2)_n$N(R)$_2$, (CHR)$_n$N(R)$_2$, NO$_2$, SCF$_3$, S(O)$_s$CF$_3$, S(O)$_s$R, SF$_5$, $C_{3-10}$cycloalkyl, $C_{5-10}$heterocyclyl, and $C_{6-10}$aryl, said alkyl, cycloalkyl, heterocyclyl and aryl optionally substituted with one to three groups of R$^b$;
R$^b$ is selected from the group consisting of H, halo, $C_{1-6}$alkyl, $(CH_2)_n$OR, and (O)$_p$$C_{1-4}$haloalkyl;
n represents 0, 1, 2, 3, or 4;
s represents 0, 1, or 2; and
p represents 0 or 1.

2. The compound according to claim 1 wherein A is represented by A1:

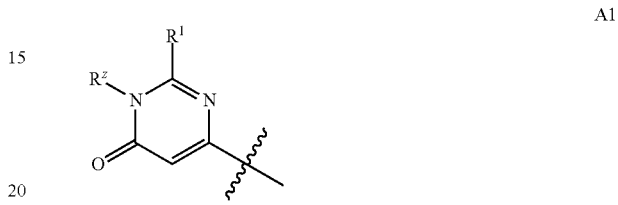

wherein R¹ is as originally described and R$^z$ is hydrogen or, $C_{1-6}$alkyl.

3. The compound according to claim 1 wherein R² is CR$^X$R$^Y$.

4. The compound according to claim 1 wherein R² is selected from the group consisting of optionally substituted methyl, ethyl isopropyl, propyl, butyl, isobutyl, pentyl, cyclopropyl, cyclobutyl, cyclopentyl, cyclohexyl, and $(CH_2)_n$phenyl.

5. The compound according to claim 2 wherein R¹ is methyl and Rz is hydrogen.

6. The compound according to claim 3 wherein R$^x$ and R$^Y$ are independently selected from the group consisting of H, $(CH_2)_n$OR, $C_{1-6}$alkyl, C(O)OR and $N(R)_2$, said alkyl optionally substituted with one to three groups of R$^a$.

7. The compound according to claim 6 wherein one of R$^x$ and R$^Y$ is hydrogen and the other is selected from selected from the group consisting of H, methyl, ethyl, propyl, isopropyl, butyl, isobutyl, pentyl, $(CH_2)_n$OH, C(O)OR, NHCH$_3$, NH$_2$, NHCH$_2$CH$_3$, OCH$_3$, O$(CH_2)_n$CH$_3$, said methyl, ethyl, propyl, isopropyl, butyl, isobutyl, and pentyl said methyl, ethyl, propyl, isopropyl, butyl, isobutyl, and pentyl optionally substituted with 1 to 3 groups of OH.

8. The compound according to claim 1 wherein R$^x$ and R$^Y$ together with the carbon atom to which they are attached combined to form a group selected from —C(=O)—, $C_{2-6}$ alkenyl, cyclopropyl, cyclobutyl, cyclopentyl, tetrahydrofuranyl.

9. The compound according to claim 1 wherein R³ is optionally substituted $C_{4-10}$heterocyclyl.

10. The compound according to claim 9 wherein R³ is selected from the group consisting of optionally substituted dihydroisochromenyl, dihydrobenzofuranyl, pyridyl, tetrahydrofuranyl, tetrahydropyranyl, and piperidinyl.

11. The compound according to claim 1 wherein R³ is optionally substituted $C_{6-10}$ aryl.

12. The compound according to claim 11 wherein R³ is optionally substituted phenyl.

13. The compound according to claim 1 wherein R² and R³ combine to form a $C_{3-10}$ heterocyclyl selected from the group consisting of tetrahydrofuranyl and tetrahydrobenzfuranyl.

14. The compound according to claim 1 represented by structural formula Ia:

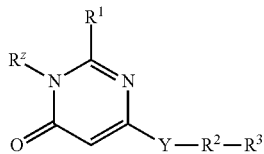

Ia or a pharmaceutically acceptable salt or hydrate thereof wherein $R^1$ is selected from the group consisting of optionally substituted hydrogen, $C_{1-6}$alkyl, cyclopropyl, cyclobutyl, and phenyl and $R^2$ is $CR^X R^Y$ wherein one of $R^X$ and $R^Y$ is hydrogen and the other is selected from the group consisting of H, methyl, ethyl, propyl, isopropyl, butyl, isobutyl, pentyl, $(CH_2)_n OH$, $C(O)OR$, $NHCH_3$, $NH_2$, $NHCH_2CH_3$, $OCH_3$, $O(CH2)_n Ch_3$, said methyl, ethyl, propyl, isopropyl, butyl, isobutyl, and pentyl optionally substituted with 1 to 3 groups of OH.

15. The compound according to claim 14 wherein $R^3$ is optionally substituted methyl, ethyl, propyl, isopropyl, butyl, isobutyl, dihydroisochromenyl, dihydrobenzofuranyl, pyridyl, tetrahydrofuranyl, tetrahydropyranyl, piperidinyl, naphthyl, and phenyl.

16. The compound according to claim 15 wherein $R^3$ is optionally substituted phenyl.

17. The compound according to claim 14 wherein $R^2$ and $R^3$ combine to form a $C_{3-10}$ heterocyclyl selected from the group consisting of tetrahydrofuranyl and tetrahydrobenzfuranyl.

18. A compound which is:
6-(1-{1-[2-fluoro-4-(trifluoromethyl)phenyl]propyl}-1H-pyrazol-4-yl)-2-methylpyrimidin-4(3H)-one,
6-(1-{1-[2-fluoro-4-(trifluoromethyl)phenyl]-2-methylpropyl}-1H-pyrazol-4-yl)-2-methylpyrimidin-4(3H)-one,
2-benzyl-6-(1-{1-[2-fluoro-4-(trifluoromethyl)phenyl]ethyl}-1H-pyrazol-4-yl)pyrimidin-4(3H)-one,
6-(1-{1-[2-fluoro-4-(trifluoromethyl)phenyl]ethyl}-1H-pyrazol-4-yl)-2-(1-methylethyl)pyrimidin-4(3H)-one,
6-(1-{1-[2-fluoro-4-(trifluoromethyl)phenyl]ethyl}-1H-pyrazol-4-yl)-2-(1-methylethyl)pyrimidin-4(3H)-one,
2-ethyl-6-(1-{1-[2-fluoro-4-(trifluoromethyl)phenyl]ethyl}-1H-pyrazol-4-yl)pyrimidin-4(3H)-one,
6-(1-{1-[2-fluoro-4-(trifluoromethyl)phenyl]cyclobutyl}-1H-pyrazol-4-yl)-2-methylpyrimidin-4(3H)-one,
6-{4-[1-(4-cyclobutylphenyl)ethyl]-1H-pyrazol- 1-yl}-2-methylpyrimidin-4(3H)-one,
6-{4-[1-(4-cyclopropylphenyl)ethyl]-1H-pyrazol- 1-yl}-2-methylpyrimidin-4(3H)-one,
2-methyl-6-(4-{1-[4-(1-methylcyclopropyl)phenyl]ethyl}-1H-pyrazol-1-yl)pyrimidin-4(3H)-one,
6-(4-{1-[4-(2-methoxyethyl)phenyl]ethyl}-1H-pyrazol-1-yl)-2-methylpyrimidin-4(3H)-one,
6-{4-[1-(3,4-dihydro-1H-isochromen-6-yl)ethyl]-1H-pyrazol-1-yl}-2-methylpyrimidin-4(3H)-one,
2-methyl-6-{4-[1-(4-propylphenyl)ethyl]-1H-pyrazol-1-yl}pyrimidin-4(3H)-one,
6-(4-{1-[4-(1-ethylcyclopropyl)phenyl]ethyl}-1H-pyrazol-1-yl)-2-methylpyrimidin-4(3H)-one,
6-{4-[1-(4-tert-butylphenyl)ethyl]-1H-pyrazol-1-yl}-2-methylpyrimidin-4(3H)-one,
6-{4-[1-(3,4-dihydro-1H-isochromen-7-yl)ethyl]-1H-pyrazol-1-yl}-2-methylpyrimidin-4(3H)-one,
6-{4-[1-(3,3-dimethyl-2,3 -dihydro-1-benzofuran-6-yl)ethyl]-1H-pyrazol-1-yl}-2-methylpyrimidin-4(3H)-one,
2-methyl-6-{4-[4-(trifluoromethoxy)benzyl]-1H-pyrazol-1-yl}pyrimidin-4(3H)-one,
2-methyl-6-{1-methyl-5-[4-(trifluoromethoxy)phenyl]-1H-pyrazol-4-yl}pyrimidin-4(3H)-one,
2-methyl-6-{1-[4-(trifluoromethoxy)benzyl]-1H-pyrazol-4-yl}pyrimidin-4(3H)-one,
2-methyl-6-(4-{[4-(trifluoromethyl)phenyl]carbonyl}-1H-pyrazol-1-yl)pyrimidin-4(3H)-one,
2-methyl-6-(4-{1-[4-(trifluoromethyl)phenyl]ethyl}-1H-pyrazol-1-yl)pyrimidin-4(3H)-one,
2-methyl-6-{4-[4-(trifluoromethyl)benzyl]-1H-pyrazol-1-yl}pyrimidin-4(3H)-one,
2-phenyl-6-{1-[4-(trifluoromethoxy)benzyl]-1H-pyrazol-4-yl}pyrimidin-4(3H)-one,
2-phenyl-6-{4-[4-(trifluoromethyl)benzyl]-1H-pyrazol-1-yl}pyrimidin-4(3H)-one,
2-phenyl-6-(4-{1-[4-(trifluoromethyl)phenyl]ethyl}-1H-pyrazol- 1-yl)pyrimidin-4(3H)-one,
2-methyl-6-(4-{(1R)-1-[4-(trifluoromethyl)phenyl]ethyl}-1H-pyrazol- 1-yl)pyrimidin-4(3H)-one,
2-methyl-6-(4-{(1S)-1-[4-(trifluoromethyl)phenyl]ethyl}-1H-pyrazol-1-yl)pyrimidin-4(3H)-one,
2-methyl-6-(3 -{1-[4-(trifluoromethyl)phenyl]ethyl}-1H-pyrazol-1-yl)pyrimidin-4(3H)-one,
2-methyl-6-(3-{1-[4-(trifluoromethyl)phenyl]ethyl}-1H-pyrazol-5-yl)pyrimidin-4(3H)-one,
2-methyl-6-(3-{(1R)-1-[4-(trifluoromethyl)phenyl]ethyl}-1H-pyrazol-5-yl)pyrimidin-4(3H)-one,
2-methyl-6-(3-{(1S)-1-[4-(trifluoromethyl)phenyl]ethyl}-1H-pyrazol-5-yl)pyrimidin-4(3H)-one,
6-(4-ethyl-1H-pyrazol-1-yl)-2-methylpyrimidin-4(3H)-one,
6-(4-{1-[3-fluoro-4-(trifluoromethyl)phenyl]ethyl}-1H-pyrazol-1-yl)-2-methylpyrimidin-4(3H)-one,
2-methyl-6-(3-{(1R)-1-[4-(trifluoromethyl)phenyl]ethyl}-1H-pyrazol-1-yl)pyrimidin-4(3H)-one,
2-methyl-6-(3-{(1S)-1-[4-(trifluoromethyl)phenyl]ethyl}-1H-pyrazol-1-yl)pyrimidin-4(3H)-one,
6-(4-{(1R)-1-[3-fluoro-4-(trifluoromethyl)phenyl]ethyl}-1H-pyrazol-1-yl)-2-methylpyrimidin-4(3H)-one,
6-(4-{(1S)-1-[3-fluoro-4-(trifluoromethyl)phenyl]ethyl}-1H-pyrazol-1-yl)-2-methylpyrimidin-4(3H)-one,
6-(4-{(1R)-1-[2-fluoro-4-(trifluoromethyl)phenyl]ethyl}-1H-pyrazol-1-yl)-2-methylpyrimidin-4(3H)-one,
6(4-{(1S)-1-[2-fluoro-4-(trifluoromethyl)phenyl]ethyl}-1H-pyrazol-1-yl)-2-methylpyrimidin-4(3H)-one,
2-methyl-6-[4-(1-pyridin-4-ylethyl)-1H-pyrazol-1-yl]pyrimidin-4(3H)-one,
2-methyl-6-(4-{2-[4-(trifluoromethyl)phenyl]tetrahydrofuran-2-yl}-1H-pyrazol-1-yl)pyrimidin-4(3H)-one,
2-methyl-6-(4-{(2R)-2-[4-(trifluoromethyl)phenyl]tetrahydrofuran-2-yl}-1H-pyrazol-1-yl)pyrimidin-4(3H)-one,
2-methyl-6-(4-{(2S)-2-[4-(trifluoromethyl)phenyl]tetrahydrofuran-2-yl}-1H-pyrazol-1-yl)pyrimidin-4(3H)-one,
2-methyl-6-(4-{1-[2-methyl-4-(trifluoromethyl)phenyl]ethenyl}-1H-pyrazol-1-yl)pyrimidin-4(3H)-one,
2-methyl-6-{4-[1-methyl-5-(trifluoromethyl)-1,3-dihydro-2-benzofuran-1-yl]-1H-pyrazol-1-yl}pyrimidin-4(3H)-one,
2-methyl-6-(4-{1-[2-methyl-4-(trifluoromethoxy)phenyl]ethyl}-1H-pyrazol-1-yl)pyrimidin-4(3H)-one,
6-(4-{4-hydroxy-4-methyl-2-]4-(trifluoromethyl)phenyl]tetrahydrofuran-2-yl}-1H-pyrazol-1-yl)-2-methylpyrimidin-4(3H)-one, 2-methyl-6-{4-[(1S)-1-methyl-5-(trifluoromethyl)-1,3-dihydro-2-benzofuran-1-yl]-1H-pyrazol-1-yl}pyrimidin-4(3H)-one,
2-methyl-6-{4-[(1R)-1-methyl-5-(trifluoromethyl)-1,3-dihydro-2-benzofuran-1-yl]-1H-pyrazol-1-yl}pyrimidin-4(3H)-one,
6-(4-{1-[2-fluoro-4-(trifluoromethyl)phenyl]-2-hydroxyethyl}-1H-pyrazol-1-yl)-2-methylpyrimidin-4(3H)-one,
6-(4-{1-[2-fluoro-4-(trifluoromethyl)phenyl]-1-hydroxyethyl}-1H-pyrazol-1-yl)-2-methylpyrimidin-4(3H)-one,
6-(4-{(1S)-1-[2-fluoro-4-(trifluoromethyl)phenyl]-2-hydroxyethyl}-1H-pyrazol-1-yl)-2-methylpyrimidin-4(3H)-one,
6-(4-{(1R)-1-[2-fluoro-4-(trifluoromethyl)phenyl]-2-hydroxyethyl}-1H-pyrazol-1-yl)-2-methylpyrimidin-4(3H)-one,
6-(4-{(1S)-1-[2-fluoro-4-(trifluoromethyl)phenyl]-1-hydroxyethyl}-1H-pyrazol-1-yl)-2-methylpyrimidin-4(3H)-one,
6-(4-{(1R)-1-[2-fluoro-4-(trifluoromethyl)phenyl]-1-hydroxyethyl}-1H-pyrazol-1-yl)-2-methylpyrimidin-4(3H)-one,
2-methyl-6-(1-{(1R)-1-[2-methyl-4-(trifluoromethyl)phenyl]ethyl}-1H-pyrazol-4-yl)pyrimidin-4(3H)-one,
2-methyl-6-(1-{(1S)-1-[2-methyl-4-(trifluoromethyl)phenyl]ethyl}-1H-pyrazol-4-yl)pyrimidin-4(3H)-one,
6-(1-{(1R)-1-[2-methoxy-4-(trifluoromethyl)phenyl]ethyl}-1H-pyrazol-4-yl)-2-methylpyrimidin-4(3H)-one,
6-(1-{(1S)-1-[2-methoxy-4-(trifluoromethyl)phenyl]ethyl}-1H-pyrazol-4-yl)-2-methylpyrimidin-4(3H)-one,
6-(1-{(1R)-1-[2-fluoro-4-(trifluoromethoxy)phenyl]ethyl}-1H-pyrazol-4-yl)-2-methylpyrimidin-4(3H)-one,
6-(1-{(1S)-1-[2-fluoro-4-(trifluoromethoxy)phenyl]ethyl}-1H-pyrazol-4-yl)-2-methylpyrimidin-4(3H)-one,
2-(3,4-dimethoxybenzyl)-6-(1-{(1R)-1-[4-(trifluoromethyl)phenyl]ethyl}-1H-pyrazol-4-yl)pyrimidin-4(3H)-one,
2-(3,4-dimethoxybenzyl)-6-(1-{(1S)-1-[4-(trifluoromethyl)phenyl]ethyl}-1H-pyrazol-4-yl)pyrimidin-4(3H)-one,
2-methyl-6-(1-{(1R)-1-[4-(pentafluoro-lambda~6~-sulfanyl)phenyl]ethyl}1-1H-pyrazol-4-yl)pyrimidin-4(3H)-one,
2-methyl-6-(1-{(1S)-1-[4-(pentafluoro-lambda~6~-sulfanyl)phenyl]ethyl}-1H-pyrazol-4-yl)pyrimidin-4(3H)-one,
2-(3,4-dimethoxybenzyl)-6-(1-{(1R)-1-[4-(pentafluoro-lambda~6~-sulfanyl)phenyl]ethyl}-1H-pyrazol-4-yl)pyrimidin-4(3H)-one,
2-(3,4-dimethoxybenzyl)-6-(1-{(1S)-1-(pentafluoro-lambda~6~-sulfanyl)phenyl]ethyl}-1H-pyrazol-4-yl)pyrimidin-4(3H)-one,
2-(3,4-dimethoxybenzyl)-6-(1-{(1R)-1-[2-fluoro-4-(trifluoromethyl)phenyl]ethyl}-1H-pyrazol-4-yl)pyrimidin-4(3H)-one,
2-(3,4-dimethoxybenzyl)-6-(1-{(1S)-1-[2fluoro-4-(trifluoromethyl)phenyl]ethyl}-1H-pyrazol-4-yl)pyrimidin-4(3H)-one,
2-(1-{1-[4-(trifluoromethyl)phenyl]ethyl}-1H-pyrazol-4-yl)-4H-pyrido[1,2-a]pyrimidin-4-one,
2-methyl-6-{1-[1-(tetrahydro-2H-pyran-4-yl)ethyl]-1H-pyrazol-4-yl}pyrimidin-4(3H)-one,
2-methyl-6-(4-{[4-(trifluoromethyl)piperidin-1-yl]methyl}-1H-pyrazol-1-yl)pyrimidin-4(3H)-one,
2-cyclopropyl-6-(1-{1-[2-fluoro-4-(trifluoromethyl)phenyl]ethyl}-1H-pyrazol-4-yl)pyrimidin-4(3H)-one,
2-cyclopropyl-6-(1-{1-[2-fluoro-4-(trifluoromethyl)phenyl]ethyl}-1H-pyrazol-4-yl)pyrimidin-4(3H)-one,
2,3-dimethyl-6-(4-{1-[4-(trifluoromethyl)phenyl]ethyl}-1H-pyrazol-1-yl)pyrimidin-4(3H)-one,
2-methyl-6-(1-{1-[3-(trifluoromethyl)phenyl]ethyl}-1H-pyrazol-4-yl)pyrimidin-4(3H)-one,
2-methyl-6-(1-{1-[4-(trifluoromethyl)phenyl]ethyl}-1H-pyrazol-3-yl)pyrimidin-4(3H)-one,
2-methyl-6-(1-{1-[4-(trifluoromethyl)phenyl]ethyl}-1H-pyrazol-5-yl)pyrimidin-4(3H)-one,
2-methyl-6-(1-{1-[4-(trifluoromethoxy)phenyl]ethyl}-1H-pyrazol-3-yl)pyrimidin-4(3H)-one,
2-methyl-6-(1-{1-[4-(trifluoromethoxy)phenyl]ethyl}-1H-pyrazol-5-yl)pyrimidin-4(3H)-one,
2-methyl-6-(1-{(1S)-1-[4-(trifluoromethyl)phenyl]ethyl}-1H-pyrazol-3 -yl)pyrimidin-4(3H)-one,
2-methyl-6-(1-{(1R)-1-[4-(trifluoromethyl)phenyl]ethyl}-1H-pyrazol-3-yl)pyrimidin-4(3H)-one,
6-(3,5-dimethyl-1-{1-[4-(trifluoromethyl)phenyl]ethyl}-1H-pyrazol-4-yl)-2-methylpyrimidin-4(3H)-one,
2-methyl-6-(3-methyl-1-{1-[4-(trifluoromethyl)phenyl]ethyl}-1H-pyrazol-4-yl)pyrimidin-4(3H)-one,
2-methyl-6-(5-methyl-1-{(1S)-1-[4-(trifluoromethyl)phenyl]ethyl}-1H-pyrazol-4-yl)pyrimidin-4(3H)-one,
2-methyl-6-(5-methyl-1-{(1R)-1-[4-(trifluoromethyl)phenyl]ethyl}-1H-pyrazol-4-yl)pyrimidin-4(3H)-one,
2-cyclopropyl-6-(1-{1-[2-fluoro-4-(trifluoromethyl)phenyl]ethyl}-1H-pyrazol-4-yl)pyrimidin-4(3H)-one,
6-(1-{(1S)-1-[2-chloro-4-(trifluoromethyl)phenyl]ethyl}-1H-pyrazol-4-yl)-2-methylpyrimidin-4(3H)-one,
6-(1-{(1S)-1-[2-chloro-4-(trifluoromethyl)phenyl]ethyl}-1H-pyrazol-4-yl)-2-methylpyrimidin-4(3H)-one,
2-ethyl-6-(1-{(1R)-1-[2-fluoro-4-(trifluoromethyl)phenyl]ethyl}-1H-pyrazol-4-yl)pyrimidin-4(3H)-one,
2-ethyl-6-(1-{(1S)-1-[2-fluoro-4-(trifluoromethyl)phenyl]ethyl}-1H-pyrazol-4-yl)pyrimidin-4(3H)-one,
6-(1-{(1R)-1-[4-(difluoromethoxy)-2-fluorophenyl]ethyl}-1H-pyrazol-4-yl)-2-methylpyrimidin-4(3H)-one,
6-(1-{(1S)-1-[4-(difluoromethoxy)-2-fluorophenyl]ethyl}-1H-pyrazol-4-yl)-2-methylpyrimidin-4(3H)-one,
6-(1-{(1R)-1-[4-(difluoromethoxy)-2-methylphenyl]ethyl}-1H-pyrazol-4-yl)-2-methylpyrimidin-4(3H)-one,
6-(1-{(1S)-1-[4-(difluoromethoxy)-2-methylphenyl]ethyl}-1H-pyrazol-4-yl)-2-methylpyrimidin-4(3H)-one,
6-{1-[(1R)-1-(4-cyclopropyl-2-fluorophenyl)ethyl]-1H-pyrazol-4-yl}-2-methylpyrimidin-4(3H)-one,
6-{1-[(1S)-1-(4-cyclopropyl-2-fluorophenyl)ethyl]-1H-pyrazol-4-yl}-2-methylpyrimidin-4(3H)-one,
6-{1-[(1R)-1-(4-cyclopropyl-2-methylphenyl)ethyl]-1H-pyrazol-4-yl}-2-methylpyrimidin-4(3H)-one,
6-{1-[(1S)-1-(4-cyclopropyl-2-methylphenyl)ethyl]-1H-pyrazol-4-yl}-2-methylpyrimidin-4(3H)-one,
6-(1-{(1R)-1-[2-fluoro-4-(2,2,2-trifluoroethyl)phenyl]ethyl}-1H-pyrazol-4-yl)-2-methylpyrimidin-4(3H)-one, 6-(1-{(1S)-1-[2-fluoro-4-(2,2,2-trifluoroethyl)phenyl]ethyl}-1H-pyrazol-4-yl)-2-methylpyrimidin-4(3H)-one,
6-(1-{(1R)-1-[2-fluoro-4-(methoxymethyl)phenyl]ethyl}-1H-pyrazol-4-yl)-2-methylpyrimidin-4(3H)-one,
6-(1-{(1S)-1-fluoro-4-(methoxymethyl)phenyl]ethyl}-1H-pyrazol-4-yl)-2-methylpyrimidin-4(3H)-one,
6-{1-[(1R)-1-(2-chloro-4-ethylphenyl)ethyl]-1H-pyrazol-4-yl}-2-methylpyrimidin-4(3H)-one,
6-{1-[(1S)-1-(2-chloro-4-ethylphenyl)ethyl]-1H-pyrazol-4-yl}-2-methylpyrimidin-4(3H)-one,
6-{1-[(1R)-1-(4-ethyl-2-fluorophenyl)ethyl]-1H-pyrazol-4-yl}-2-methylpyrimidin-4(3H)-one,
6-{1-[(1S)-1-(4-ethyl-2-fluorophenyl)ethyl]-1H-pyrazol-4-yl}-2-methylpyrimidin-4(3H)-one,
6-(1-{(1R)-1-[2-chloro-4-(methoxymethyl)phenyl]ethyl}-1H-pyrazol-4-yl)-2-methylpyrimidin-4(3H)-one,
6-(1-{(1S)-1-[2-chloro-4-(methoxymethyl)phenyl]ethyl}-1H-pyrazol-4-yl)-2-methylpyrimidin-4(3H)-one,
2-methyl-6-(1-{(1R)-1-[2-methyl-4-(2,2,2-trifluoroethyl)phenyl]ethyl}-1H-pyrazol-4-yl)pyrimidin-4(3H)-one
2-methyl-6-(1-{(1S)-1-[2-methyl-4-(2,2,2-trifluoroethyl)phenyl]ethyl}-1H-pyrazol-4-yl)pyrimidin-4(3H)-one,
6-{1-[(1R)-1-(2-chloro-4-cyclopropylphenyl)ethyl]-1H-pyrazol-4-yl}-2-methylpyrimidin-4(3H)-one,
6-{1-[(1S)-1-(2-chloro-4-cyclopropylphenyl)ethyl]-1H-pyrazol-4-yl}-2-methylpyrimidin-4(3H)-one,
6-(1-{(1S)-1-[2,6-difluoro-4-(trifluoromethyl)phenyl]ethyl}-1H-pyrazol-4-yl)-2-methylpyrimidin-4(3H)-one,
6-(1-{(1S)-1-[2-fluoro-4-(trifluoromethyl)phenyl]-2-hydroxyethyl}-1H-pyrazol-4-yl)-2-methylpyrimidin-4(3H)-one,
6-(1-{(1R)-1-[2-fluoro-4-(trifluoromethyl)phenyl]-2-hydroxyethyl}-1H-pyrazol-4-yl)-2-methylpyrimidin-4(3H)-one,
6-{4-[(1R)-1-(2-fluoro-4-propylphenyl)-1-hydroxyethyl]-1H-pyrazol-1-yl}-2-methylpyrimidin-4(3H)-one,
6-{4-[(1S)-1-(2-fluoro-4-propylphenyl)-1-hydroxyethyl]-1H-pyrazol-1-yl}-2-methylpyrimidin-4(3H)-one,
6-{1-[(1S)-1-(4-ethyl-2-fluorophenyl)-2-hydroxyethyl]-1H-pyrazol-4-yl}-2-methylpyrimidin-4(3H)-one,
6-{1-[(1R)-1-(4-ethyl-2-fluorophenyl)-2-hydroxyethyl]-1H-pyrazol-4-yl}-2-methylpyrimidin-4(3H)-one,
methyl [2-fluoro-4-(trifluoromethyl)phenyl][4-(2-methyl-6-oxo-1,6-dihydropyrimidin-4-yl)-1H-pyrazol-1-yl]acetate,
methyl (2-chloro-4-ethylphenyl)[4-(2-methyl-6-oxo-1,6-dihydropyrimidin-4-yl)-1H-pyrazol-1-yl]acetate,
6-{4-[(1S)-1-(4-ethyl-2-fluorophenyl)-2-hydroxyethyl]-1H-pyrazol-1-yl}-2-methylpyrimidin-4(3H)-one,
6-{4-[(1R)-1-(4-ethyl-2-fluorophenyl)-2-hydroxyethyl]-1H-pyrazol-1-yl}-2-methylpyrimidin-4(3H)-one,
6-{1-[(1S)-1-(2-chloro-4-ethylphenyl)-2-hydroxyethyl]-1H-pyrazol-4-yl}-2-methylpyrimidin-4(3H)-one,
6-{1-[(1R)-1-(2-chloro-4-ethylphenyl)-2-hydroxyethyl]-1H-pyrazol-4-yl}-2-methylpyrimidin-4(3H)-one,
6-(4-{(1R)-1-[2-chloro-4-(trifluoromethyl)phenyl]-1-hydroxyethyl}-1H-pyrazol-1-yl)-2-methylpyrimidin-4(3H)-one,
6-(4-{(1S)-1-[2-chloro-4-(trifluoromethyl)phenyl]-1-hydroxyethyl}-1H-pyrazol-1-yl)-2-methylpyrimidin-4(3H)-one,
6-{4-[(1R)-1-(4-ethyl-2-fluorophenyl)-1-hydroxyethyl]-1H-pyrazol-1-yl 1-2-methylpyrimidin-4(3H)-one,
6-{4-[(1S)-1-(4-ethyl-2-fluorophenyl)-1-hydroxyethyl]-1H-pyrazol-1-yl}-2-methylpyrimidin-4(3H)-one,
6-{4-[1-(2-chloro-4-ethylphenyl)-1-hydroxyethyl]-1H-pyrazol-1-yl}-2-methylpyrimidin-4(3H)-one,
6-{4-[(1S)-1-(2-chloro-4-ethylphenyl)-2-hydroxyethyl]-1H-pyrazol-1-yl}-2-methylpyrimidin-4(3H)-one,
6-{4-[(1R)-1-(2-chloro-4-ethylphenyl)-2-hydroxyethyl]-1H-pyrazol-1-yl}-2-methylpyrimidin-4(3H)-one,
6-(1-{(1S)-1-[2-chloro-4-(trifluoromethyl)phenyl]-2-hydroxyethyl}-1H-pyrazol-4-yl)-2-methylpyrimidin-4(3H)-one,
6-(1-{(1R)-1-[2-chloro-4-(trifluoromethyl)phenyl]-2-hydroxyethyl}-1H-pyrazol-4-yl)-2-methylpyrimidin-4(3H)-one,
6-(4-{(1S)-1-[2-fluoro-4-(trifluoromethyl)phenyl]-3-hydroxypropyl}-1H-pyrazol-1-yl)-2-methylpyrimidin-4(3H)-one,
6-(4-{(1R)-1-[2-fluoro-4-(trifluoromethyl)phenyl]-3-hydroxypropyl}-1H-pyrazol-1-yl)-2-methylpyrimidin-4(3H)-one,
2-methyl-6-(1-{1-[4-(trifluoromethoxy)phenyl]ethyl}-1H-pyrazol-4-yl)pyrimidin-4(3H)-one,
2-methyl-6-(1-{1-[4-(trifluoromethyl)phenyl]ethyl}-1H-pyrazol-4-yl)pyrimidin-4(3H)-one,
2-methyl-6-(1-{(1S)-1-[4-(trifluoromethoxy)phenyl]ethyl}-1H-pyrazol-4-yl)pyrimidin-4(3H)-one,
2-methyl-6-(1-{(1R)-1-[4-(trifluoromethoxy)phenyl]ethyl}-1H-pyrazol-4-yl)pyrimidin-4(3H)-one,
2-methyl-6-(4-{1-[4-(trifluoromethyl)phenyl]propyl}-1-1H-pyrazol-1-yl)pyrimidin-4(3H)-one,
2-methyl-6-(4-{2-methyl-1-[4-(trifluoromethyl)phenyl]propyl}-1H-pyrazol-1-yl)pyrimidin-4(3H)-one,
2-methyl-6-(1-methyl-3-{1-[4-(trifluoromethyl)phenyl]ethyl}-1-1H-pyrazol-5-yl)pyrimidin-4(3H)-one,
2-methyl-6-(4-{(methylamino)[4-(trifluoromethyl)phenyl]methyl}-1-1H-pyrazol-1-yl)pyrimidin-4(3H)-one,
2-methyl-6-(4-{(methylamino)[4-(trifluoromethyl)phenyl]methyl}-1H-pyrazol-1-yl)pyrimidin-4(3H)-one,
6-(4-{methoxy [4-(trifluoromethyl)phenyl]methyl}-1H-pyrazol-1-yl)-2-methylpyrimidin-4(3H)-one,
2-methyl-6-(1-methyl-3-{(1S)-1-[4-(trifluoromethyl)phenyl]ethyl}-1H-pyrazol-5-yl)pyrimidin-4(3H)-one,
2-methyl-6-(1-methyl-3-{(1R)-1-[4-(trifluoromethyl)phenyl]ethyl}-1H-pyrazol-5-yl)pyrimidin-4(3H)-one,
2-methyl-6-(1-methyl-5-{1-[4-(trifluoromethyl)phenyl]ethyl}-1H-pyrazol-3-yl)pyrimidin-4(3H)-one,
2-methyl-6-(1-methyl-5-{(1S)-1-[4-(trifluoromethyl)phenyl]ethyl}-1H-pyrazol-3-yl)pyrimidin-4(3H)-one,
2-methyl-6-(1-methyl-5-{(1R)-1-[4-(trifluoromethyl)phenyl]ethyl}-1H-pyrazol-3-yl)pyrimidin-4(3H)-one,
2-(3,4-dimethoxybenzyl)-6-(3-{1-[4-(trifluoromethyl)phenyl]ethyl}-1H-pyrazol-1-yl)pyrimidin-4(3H)-one,
2-(3,4-dimethoxybenzyl)-6-(1-{1-[4-(trifluoromethyl)phenyl]ethyl}-1H-pyrazol-4-yl)pyrimidin-4(3H)-one,
2-(3,4-dimethoxybenzyl)-6-(3-{(1S)-1-[4-(trifluoromethyl)phenyl]ethyl}-1H-pyrazol-1-yl)pyrimidin-4(3H)-one,
2-(3,4-dimethoxybenzyl)-6-(3-{(1R)-1-[4-(trifluoromethyl)phenyl]ethyl}-1H-pyrazol-1-yl)pyrimidin-4(3H)-one,
6-(1-{1-[2-fluoro-4-(trifluoromethyl)phenyl]ethyl}-1H-pyrazol-4-yl)-2-methylpyrimidin-4(3H)-one,
6-(1-{(1S)-1-[2-fluoro-4-(trifluoromethyl)phenyl]ethyl}-1H-pyrazol-4-yl)-2-methylpyrimidin-4(3H)-one, 6-(1-{(1R)-1-[2-fluoro-4-(trifluoromethyl)phenyl]ethyl}-1-1H-pyrazol-4-yl)-2-methylpyrimidin-4(3H)-one, 2-(3,4-dimethoxybenzyl)-6-(4-{1-[4-(trifluoromethyl)phenyl]ethyl}-1H-pyrazol-1-yl)pyrimidin-4(3H)-one, 2-(3,4-dimethoxybenzyl)-6-(4-{1-[4-(trifluoromethyl)phenyl]ethyl}-1H-pyrazol-1-yl)pyrimidin-4(3H)-one, 6-(1{(1S)-1-[2-fluoro-4-(trifluoromethyl)phenyl]ethyl}-1H-pyrazol-4-yl)-2-(4-methoxybenzyl)pyrimidin-4(3H)-one, 6-(1-{(1R)-1-[2-fluoro-4-(trifluoromethyl)phenyl]ethyl}-1H-pyrazol-4-yl)-2-(4-methoxybenzyl)pyrimidin-4(3H)-one, 6-(1-{(1S)-1-[2-fluoro-4-(trifluoromethyl)phenyl]ethyl}-1H-pyrazol-4-yl)-2-(3-methoxybenzyl)pyrimidin-4(3H)-one, 6-(1-{(1R)-1-[2-fluoro-4-(trifluoromethyl)phenyl]ethyl}-1H-pyrazol-4-yl)-2-(3-methoxybenzyl)pyrimidin-4(3H)-one, 2-(4-fluoro-3-methoxybenzyl)-6-(1-{(1S)-1-[2-fluoro-4-(trifluoromethyl)phenyl]ethyl}-1H-pyrazol-4-yl)pyrimidin-4(3H)-one, 2-(4-fluoro-3-methoxybenzyl)-6-(1-{(1R)-1-[2-fluoro-4-(trifluoromethyl)phenyl]ethyl}-1H-pyrazol-4-yl)pyrimidin-4(3H)-one, 6-(1-{(1S)-1-[2,4-bis(trifluoromethyl)phenyl]ethyl}-1H-pyrazol-4-yl)-2-methylpyrimidin-4(3H)-one, 6-(1-{(1R)-1-[2,4-bis(trifluoromethyl)phenyl]ethyl}-1H-pyrazol-4-yl)-2-methylpyrimidin-4(3H)-one, 2-(3-fluoro-4-methoxybenzyl)-6-(1-{(1S)-1-[2-fluoro-4-(trifluoromethyl)phenyl]ethyl}-1H-pyrazol-4-yl)pyrimidin-4(3H)-one, 2-(3-fluoro-4-methoxybenzyl)-6-(1-{(1R)-1-fluoro-4-(trifluoromethyl)phenyl]ethyl}-1H-pyrazol-4-yl)pyrimidin-4(3H)-one, 6-{1-[(1S)-1-(2-chloro-4-methylphenyl)ethyl]-1H-pyrazol-4-yl}-2-methylpyrimidin-4(3H)-one, 6-{1-[(1R)-1-(2-chloro-4-methylphenyl)ethyl]-1H-pyrazol-4-yl}-2-methylpyrimidin-4(3H)-one, 6-{1-[(1S)-1-(2-fluoro-4-methylphenyl)ethyl]-1H-pyrazol-4-yl}-2-methylpyrimidin-4(3H)-one, 6-{1-[(1R)-1-(2-fluoro-4-methylphenyl)ethyl]-1H-pyrazol-4-yl}-2-methylpyrimidin-4(3H)-one, 6-{1-[1-(4-fluorophenyl)ethyl]-1H-pyrazol-4-yl}-2-methylpyrimidin-4(3H)-one, 2-methyl-6-{1-[(4-methylphenyl)ethyl]-1H-pyrazol-4-pyrimidin-4(3H)-one, 2-methyl-6-(1-{1-(trifluoromethyl)phenyl]butyl}-1H-pyrazol-4-yl)pyrimidin-4(3H)-one, methyl 4-{1-[4-(2-methyl-6-oxo-1,6-dihydropyrimidin-4-yl)-1H-pyrazol-1-yl]ethyl}benzoate, 2-methyl-6-[1-(1-phenylethyl)-1H-pyrazol-4-yl]pyrimidin-4(3H)-one, 2-methyl-6-{1-[1-(4-methylphenyl)ethyl]-1H-pyrazol-3-yl}pyrimidin-4(3H)-one, 2-methyl-6-[1-(1-phenylethyl)-1H-pyrazol-3-yl]pyrimidin-4(3H)-one, 2-methyl-6-(1-{1-[3-(trifluoromethyl)phenyl]ethyl}-1H-pyrazol-3-yl)pyrimidin-4(3H)-one, 2-methyl-6-(1-{1-[4-(trifluoromethyl)phenyl]butyl}-1H-pyrazol-3-yl)pyrimidin-4(3H)-one, 6-{1-[1-(4-fluorophenyl)ethyl]-1H-pyrazol-3-yl}-2-methylpyrimidin-4(3H)-one, methyl 4-{1-[3-(2-methyl-6-oxo-1,6-dihydropyrimidin-4-yl)-1H-pyrazol-1-yl]ethyl}benzoate, 6-(1-{(1R)-1-[2,6-difluoro-4-(trifluoromethyl)phenyl]ethyl}-1H-pyrazol-4-yl)-2-methylpyrimidin-4(3H)-one, or a pharmaceutically acceptable salt and hydrate thereof.

19. A pharmaceutical composition which comprises a pharmaceutically acceptable carrier and a compound of claim 1 or a pharmaceutically acceptable salt thereof.

\* \* \* \* \*